(12) United States Patent
Xu et al.

(10) Patent No.: US 11,466,003 B2
(45) Date of Patent: Oct. 11, 2022

(54) NITROGENOUS HETEROCYCLIC AROMATIC COMPOUND, PREPARATION METHOD THEREFOR, PHARMACEUTICAL COMPOSITION THEREOF, AND APPLICATION THEREOF

(71) Applicant: SHANGHAI YINGLI PHARMACEUTICAL CO., LTD, Shanghai (CN)

(72) Inventors: Zusheng Xu, Shanghai (CN); Yangtong Lou, Shanghai (CN); Li Chen, Shanghai (CN)

(73) Assignee: SHANGHAI YINGLI PHARMACEUTICAL CO., LTD, Shanghai (CN)

( * ) Notice: Subject to any disclaimer, the term of this patent is extended or adjusted under 35 U.S.C. 154(b) by 673 days.

(21) Appl. No.: 16/321,457

(22) PCT Filed: Jul. 6, 2017

(86) PCT No.: PCT/CN2017/091940
§ 371 (c)(1),
(2) Date: Mar. 19, 2019

(87) PCT Pub. No.: WO2018/019106
PCT Pub. Date: Feb. 1, 2018

(65) Prior Publication Data
US 2021/0300916 A1   Sep. 30, 2021

(30) Foreign Application Priority Data
Jul. 29, 2016 (CN) .......................... 201610613592.3

(51) Int. Cl.
| C07D 471/04 | (2006.01) |
| C07D 401/10 | (2006.01) |
| C07D 405/10 | (2006.01) |
| C07D 487/04 | (2006.01) |
| C07D 519/00 | (2006.01) |

(52) U.S. Cl.
CPC ......... *C07D 471/04* (2013.01); *C07D 401/10* (2013.01); *C07D 405/10* (2013.01); *C07D 487/04* (2013.01); *C07D 519/00* (2013.01); *C07B 2200/05* (2013.01)

(58) Field of Classification Search
CPC .. C07D 471/04; C07D 401/10; C07D 405/10; C07D 487/04; C07D 519/00
See application file for complete search history.

(56) References Cited

U.S. PATENT DOCUMENTS

| 5,612,360 | A | * | 3/1997 | Boyd ............... A61P 43/00 514/381 |
| 7,470,807 | B2 | | 12/2008 | Shoda et al. |
| 8,080,568 | B1 | | 12/2011 | Kim et al. |
| 2007/0142376 | A1 | | 6/2007 | Fleenor et al. |
| 2007/0213333 | A1 | | 9/2007 | Shoda et al. |
| 2010/0267731 | A1 | | 10/2010 | Nakamura |
| 2011/0319406 | A1 | | 12/2011 | Kim et al. |
| 2013/0102603 | A1 | | 4/2013 | Dorsch et al. |

FOREIGN PATENT DOCUMENTS

| CN | 1956979 | A | 5/2007 |
| CN | 102695511 | A | 9/2012 |
| CN | 102958930 | A | 3/2013 |
| CN | 103025731 | A | 4/2013 |
| CN | 103764655 | A | 4/2014 |
| EP | 0574174 | A2 | 12/1993 |
| JP | 2006527722 | A | 12/2006 |
| JP | 2007528362 | A | 10/2007 |
| JP | 2012193123 | A | 10/2012 |
| JP | 2012524073 | A | 10/2012 |
| JP | 2013533252 | A | 8/2013 |
| KR | 20060079190 | A | 7/2006 |
| WO | 2002094833 | A1 | 11/2002 |
| WO | 2004013135 | A1 | 2/2004 |
| WO | 2004048383 | A1 | 6/2004 |

(Continued)

OTHER PUBLICATIONS

Chemical Abstracts STN Registry Database, record for RN 860631-34-1, "3-(1-methyl-1H-indazol-5-yl)-4-(2-pyridinyl)-benzenepropanoic acid"; Entered STN on Aug. 17, 2005. (Year: 2005).*
Gellibert; J. Med. Chem. 2004, 47, 18, 4494-4506. DOI: 10.1021/jm0400247 (Year: 2004).*
Chemical Abstracts STN Registry Database, record for RN 1185447-31-7, "5-[5-Fluoro-2-(1H-pyrazol-1-yl)phenyl]-1,6-dihydro-3-methyl-1-(1-methylethyl)imidazo[4,5-c]pyrazole", Entered into STN on Sep. 17, 2009. (Year: 2009).*
National Center for Biotechnology Information. PubChem Substance Record for SID 316945036, SID 316945036, Source: ChemBridge. https://pubchem.ncbi.nlm.nih.gov/substance/316945036. Available Sep. 1, 2016. (Year: 2016).*

(Continued)

*Primary Examiner* — Daniel R Carcanague
(74) *Attorney, Agent, or Firm* — Foley & Lardner LLP

(57) ABSTRACT

Provided are a nitrogenous heterocyclic aromatic compound, a preparation method therefor, a pharmaceutical composition thereof, and an application thereof. The nitrogenous heterocyclic aromatic compound can be used for treating and/or preventing various diseases mediated by ALK5.

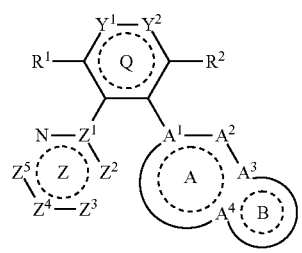

14 Claims, No Drawings

(56) References Cited

FOREIGN PATENT DOCUMENTS

| WO | 2004111036 | A1 | | 12/2004 | |
|---|---|---|---|---|---|
| WO | WO-2005016862 | A1 | * | 2/2005 | .............. A61P 43/00 |
| WO | 2009022171 | A1 | | 2/2009 | |
| WO | 2009133070 | A1 | | 11/2009 | |
| WO | 2010121162 | A1 | | 10/2010 | |
| WO | 2012002680 | A2 | | 1/2012 | |
| WO | 2014055955 | A1 | | 4/2014 | |

OTHER PUBLICATIONS

National Center for Biotechnology Information. PubChem Substance Record for SID 316937786, SID 316937786, Source: ChemBridge. https://pubchem.ncbi.nlm.nih.gov/substance/316937786. Available Sep. 1, 2016. (Year: 2016).*
Chemical Abstracts STN Registry Database Record for RN 159749-81-2, Entered STN on Dec. 23, 1994. (Year: 1994).*
Chemical Abstracts STN Registry Database Record for RN 1269048-57-8, Entered STN on Mar. 21, 2011. (Year: 2011).*
Chemical Abstracts STN Registry Database, record for RN 477703-12-1, entered into STN Dec. 24, 2002. (Year: 2002).*
Kubiczkova; J Transl Med 10, 183 (2012). https://doi.org/10.1186/1479-5876-10-183 (Year: 2012).*
Chemical Abstracts STN Registry Database, record for RN 1350283-76-9, entered STN: Dec. 7, 2011. (Year: 2011).*
Chemical Abstracts STN Registry Database, record for RN 1350133-65-1, entered STN: Dec. 7, 2011. (Year: 2011).*
Chemical Abstracts STN Registry Database, record for RN 1347592-57-7, entered STN: Dec. 2, 2011. (Year: 2011).*
Notification of Reason for Refusal dated Jun. 18, 2021 issued in counterpart Korean Application No. 10-2019-7005815, with English translation, 11 pages.
Office Action dated May 27, 2021 issued in counterpart Mexican Application No. MX/a/2019/001225, with English translation, 13 pages.
Communication pursuant to Article 94(3) EPC dated Jun. 17, 2021 issued in counterpart European Application No. 17 833 409.0, 4 pages.
Notice of Reasons for Refusal dated Mar. 16, 2021 issued in corresponding Japanese Patent Application No. 2019-504925, with English translation, 6 pages.
Rik Derynck et al., "Smad-dependent and smad-independent pathways in TGF-β family signalling", Nature, 2003, vol. 425,No. 9, pp. 577-584.
Rosemary J. Akhurst et al., "Targeting the TGF-β signalling pathway in disease", Nat Rev Drug Discov., 2012, vol. 11, No. 10, pp. 790-811.
Neuzillet et al., "Targeting the TGFβ pathway for cancer therapy", Pharmacology & Therapeutics, 2015, vol. 147, pp. 22-31.
You-Gui Li et al.,"Bulky Phosphane ligand for monoselective ruthenium-catalayzed, directed o-C—H arylation with challenging aryl chlorides", Synlett, 2016, vol. 28, No. 4, pp. 499-503.
International Search Report and Written Opinion of PCT/CN2017/091940 dated Sep. 30, 2017.
Extended European Search Report issued in the counterpart European application No. 17833409.0 dated Jan. 13, 2020.
Second Office Action issued in counterpart Russian application No. 2019105829 dated Feb. 27, 2020.
First Examination Report issued in the counterpart Australian application No. 2017302959 dated Apr. 2, 2020.
Ya-Ling Zou et al., "Solvent and base in one: tetra-n-butylammonium acetate as a multi-purpose Ionic liquid medium for ru-catalyzed directed mono- and Di-o-C—H arylation reactions", Eur. J. Org. Chem., 2017, pp. 6274-6282.

Reznickova Eva et al., "ALK5 kinase inhibitory activity and synthesis of 2,3,4-substituted 5,5-dimethyl-5,6-dihydro-4H-pyrrolo[1,2-b]pyrazoles", European Journal of Medicinal Chemistry, vol. 127, 2017, pp. 632-642.
Mark L Boys et al., "Discovery of a series of 2-(1H-pyrazol-1-yl)pyridines as ALK5 inhibitors with potential utility in the prevention of dermal scarring", Bioorganic & Medicinal Chemistry Letters, vol. 22, No. 10, 2012, pp. 3392-3397.
Marike Marjolijn Van Beuge et al., "Enhanced effectivity of an ALK5-inhibitor after cell-specific delivery to hepatic stellate cells in mice with liver injury", PLOS One, vol. 8, No. 2, 2013, pp. 1-9.
Malihe Ebrahimi et al., "Interactions between activin-like kinase (ALK5) receptor and its inhibitors and the construction of a docking descriptor-based QSAR model", Journal of the Brazilian Chemical Society, vol. 23, No. 11, 2012, pp. 2043-2053.
Gellibert F et al., "Design of novel quinazoline derivatives and related analogues as potent and selective ALK5 inhibitors", Bioorganic & Medicinal Chemistry Letters, vol. 19, No. 8, 2009, pp. 2277-2281.
Ren Ji-Xia et al., "Pharmacophore modeling and virtual screening for the discovery of new transforming growth factor-beta type I receptor (ALK5) inhibitors", European Journal of Medicinal Chemistry, vol. 44, No. 11, pp. 4259-4265.
First Office Action issued in counterpart Canadian application No. 3,035,115 dated Apr. 14, 2020, 5 pages.
First Office Action issued in counterpart Indian application No. 201927007816 dated Apr. 23, 2020, 6 pages.
Written opinion issued in counterpart Singaporean application No. 112019017730 dated Jun. 4, 2020, 8 pages.
Notice of Reasons for Refusal issued in counterpart Japanese application No. 2019-504925 dated Jun. 23, 2020, 9 pages.
Second Office Action issued in counterpart Chinese application No. 201710547913.9 dated Jul. 7, 2020, 12 pages.
First Office Action issued in counterpart New Zealand application No. 751116 dated Jul. 24, 2020, 6 pages.
First Office Action issued in the counterpart Russian application No. 2019105829 dated Oct. 10, 2019.
Data base Registry[online]RN 1350283-76-9, Jul. 12, 2011, STN.
Data base Registry[online]RN 1350133-65-1, Jul. 12, 2011, STN.
Data base Registry[online]RN 1349073-33-1, May 12, 2011, STN.
Data base Registry[online]RN 1349029-63-5, May 12, 2011, STN.
Data base Registry[online]RN 1349009-24-0, May 12, 2011, STN.
Data base Registry[online]RN 1349001-52-0, May 12, 2011, STN.
Data base Registry[online]RN 1348415-89-3, Apr. 12, 2011, STN.
Data base Registry[online]RN 1348313-73-4, Apr. 12, 2011, STN.
Data base Registry[online]RN 1348108-96-2, Apr. 12, 2011, STN.
Data base Registry[online]RN 1347861-72-6, Apr. 12, 2011, STN.
Data base Registry[online]RN 1347592-57-7, Feb. 12, 2011, STN.
Data base Registry[online]RN 1347343-36-5, Feb. 12, 2011, STN.
Data base Registry[online]RN 1347096-42-7, Jan. 12, 2011, STN.
Data base Registry[online]RN 13486928-30-0, Jan. 12, 2011, STN.
First Office Action and First Search Report issued in the counterpart Chinese application No. 201710547913.9 dated Dec. 24, 2019.
First Office Action issued in the counterpart Israeli application No. 264511 dated Oct. 25, 2020, with English translation, 11 pages.
First Office Action issued in the counterpart Korean application No. 10-2019-7005815 dated Nov. 30, 2020, with English translation, 13 pages.
Second Office Action dated Oct. 19, 2021 issued in counterpart IL application No. 264511, with English translation, 8 pages.
Second Office Action dated Oct. 28, 2021 issued in counterpart MX application No. MX/a/2019/001225, with English translation, 15 pages.
Second Written Opinion issued in the counterpart Singaporean Application No. 11201901773Q dated Dec. 6, 2021, 8 pages.
Office Action dated Apr. 22, 2022 issued in MX Patent Application MX/a/2019/001225, with English translation, 10 pages.

* cited by examiner

NITROGENOUS HETEROCYCLIC AROMATIC COMPOUND, PREPARATION METHOD THEREFOR, PHARMACEUTICAL COMPOSITION THEREOF, AND APPLICATION THEREOF

The present application claims the benefit of the Chinese Patent Application No. CN201610613592.3 filed on Jul. 29, 2016. The content of the above Chinese Patent Application is incorporated herein by reference in its entirety.

FIELD OF INVENTION

The present invention relates to a nitrogenous aromatic heterocyclic compound, a preparation method, a composition and a use thereof.

PRIOR ARTS

Transforming growth factor-β (TGF-β) is a multifunctional cytokine that participates in the regulation of cell proliferation, differentiation and apoptosis through the complex receptor signaling pathway on the cell surface in an autocrine, paracrine and endocrine manner. TGF-β and various related proteins such as activins, inhibins, bone morphogenetic proteins and Mullerian-inhibiting substances belong to TGF-β superfamily (TGF-β s).

TGF-β has three major cellular receptors which are type I, type II, and type III receptors. Type I and type II receptors are transmembrane serine/threonine kinases, which transmit signals at the same time. Type III receptor does not transmit signal and plays a role of transferring TGF-β to type II receptor indirectly affecting signal transduction.

The TGF-β signaling pathway mainly involves TGF-β-Smad signaling pathway. The Smad protein family is an intracellular signal transduction protein discovered in recent years, and there are eight Smad protein molecules known in humans. After activation of TGF-β in the form of an inactive protein complex, TGF-β forms a bis-dimeric receptor complex with the type II receptor (TGFβR II) and the type I receptor (TGFβR I, also known as ALK5 (activin-like kinase 5)). The type II receptor is phosphorylated and activates the type I receptor. The type I receptor phosphorylates the Smad protein molecule (Smad2/3) which is then released into the cytosol and forms a complex with Smad4 protein. The complex is transferred into the nucleus and regulates the transcription of the TGF-β target gene to produce biological effects by binding to different transcription factors and transcriptional coactivators or transcriptional co-inhibitors. The TGF-β-Smad signaling pathway plays an important role in the regulation of cell proliferation, differentiation, apoptosis, adhesion, migration, extracellular matrix synthesis, wound repair, and immune function (Nature 2003, 425, 577). Studies have shown that abnormal TGF-β signaling is associated with many diseases, e.g., cancer, renal fibrosis, liver fibrosis, pulmonary fibrosis, viral infection, chronic nephritis, acute nephritis, diabetic nephropathy, osteoporosis, arthritis, wound healing, ulceration, corneal trauma, heart valve stenosis, congestive cardiac necrosis, neurological impairment, Alzheimer's syndrome, peritoneal or subcutaneous adhesions, atherosclerosis and tumor metastasis. The important node TGFβR I (ALK5) of the TGF-β signaling pathway is an ideal target for the treatment of these diseases. Inhibiting the phosphorylation of its downstream signal Smad2 or Smad3 by ALK5 can block or partially block the transmission of TGF-β signals into cells and correct the abnormalities of the TGF-β signals, thereby treating and preventing various ALK5-mediated diseases (*Nat Rev Drug Discov.* 2012 October, 11(10): 790-811; *Pharmacology & Therapeutics* 147 (2015) 22-31).

Some compounds which can be used as ALK5 inhibitors have been disclosed in the prior art, e.g., WO2012002680, WO2009022171, WO2009133070, WO2004048383, WO2004013135, WO2002094833.

The present inventors have unexpectedly discovered that a new class of nitrogenous aromatic heterocyclic compounds can be used as ALK5 inhibitors, and thus they can be used to treat and prevent various diseases mediated by ALK5.

Content of the Present Invention

The technical problem to be solved in the present invention is to provide a novel ALK5 inhibitor which is completely different from that of the prior art for treating and/or preventing various ALK5-mediated diseases.

The present invention provides a nitrogenous aromatic heterocyclic compound represented by formula I or a pharmaceutically acceptable salt thereof:

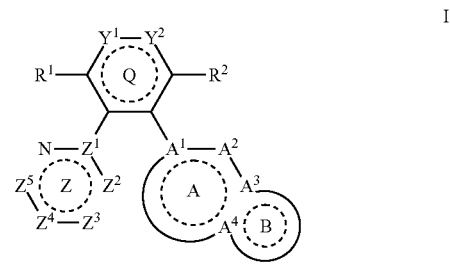

wherein, ring Z is a 5-6 membered heteroaromatic ring having at least one N;

ring Q is a benzene ring or a 5-6 membered heteroaromatic ring;

ring A is a substituted or unsubstituted benzene ring or a substituted or unsubstituted 5-6 membered heteroaromatic ring;

ring B is a substituted or unsubstituted 5-6 membered heteroaromatic ring;

$Z^1$ is N or C;
$Z^2$ is S, O, N, $NR^{a1}$ or $CR^{2'}$;
$Z^3$ is S, O, N, $NR^{a2}$ or $CR^{3'}$;
$Z^4$ is S, O, N, $NR^{a3}$ or $CR^{4'}$;
$Z^5$ is N, $CR^{5'}$ or a single bond;
when $Z^1$ is N, $Z^5$ is a single bond;
when $Z^2$ is S, O or $NR^{a1}$, or $Z^3$ is S, O or $NR^{a2}$, or $Z^4$ is S, O or $NR^{a3}$, $Z^1$ is C and $Z^5$ is a single bond;
when $Z^2$ is S or O, $Z^3$ is N or $CR^{3'}$, $Z^4$ is N or $CR^{4'}$, $Z^3$ and $Z^4$ are not N simultaneously;
when $Z^3$ is S or O, $Z^2$ is N or $CR^{2'}$, $Z^4$ is N or $CR^{4'}$, $Z^2$ and $Z^4$ are not N simultaneously;
when $Z^4$ is S or O, $Z^2$ is N or $CR^{2'}$, $Z^3$ is N or $CR^{3'}$, $Z^2$ and $Z^3$ are not N simultaneously;
when $Z^5$ is not a single bond, $Z^1$ is C, at most one of $Z^2$, $Z^3$, $Z^4$ and $Z^5$ is N;

$Y^1$ is S, O, N, $NR^3$ or $CR^4$;
$Y^2$ is N, $CR^5$ or a single bond;
when $Y^1$ is S, O or $NR^3$, $Y^2$ is a single bond;
when $Y^1$ is N or $CR^4$, $Y^2$ is N or $CR^5$;
$A^1$ is C; each of $A^3$ and $A^4$ is independently N or C, $A^2$ is N, O, S, $CR^{a4}$, $CR^{10}$ or $CR^{13}$, $R^{13}$ is halogen, deuterium or cyano;

each of $R^1$ and $R^2$ is independently hydrogen, deuterium, halogen, cyano, nitro, substituted or unsubstituted $C_{1-6}$ alkyl, $C_{2-8}$ alkenyl, $C_{2-8}$ alkynyl, $C_{3-8}$ cycloalkyl, 3-10 membered heterocyclyl, or —$R^9$, the substituent in the substituted $C_{1-6}$ alkyl is selected from the group consisting of deuterium, halogen, $C_{3-8}$ cycloalkyl, 3-10 membered heterocyclyl and $R^{10}$ (the number of the substituent is preferably 1 to 3), when there are more substituents than one, the substituents are the same or different; $R^9$ is —$OR^{b1}$, —$NR^{b2}R^{b3}$, —$SR^{b4}$, —$C(O)OR^{b5}$, —$C(O)NR^{b6}R^{b7}$, —$C(O)N(R^{b8})OR^{b9}$, —$C(O)R^{b10}$, —$S(O)R^{b11}$, —$S(O)OR^{b12}$, —$S(O)_2R^{b13}$, —$S(O)_2OR^{b14}$, —$OC(O)R^{b15}$, —$OC(O)OR^{b16}$, —$OC(O)NR^{b17}R^{b18}$, —$N(R^{b19})C(O)R^{b20}$, —$N(R^{b21})C(O)OR^{b22}$, —$N(R^{b23})C(O)NR^{b24}R^{b25}$, —$N(R^{b26})S(O)_2R^{b27}$, —$N(R^{b28})S(O)_2NR^{b29}R^{b30}$, —$P(O)(OR^{b31})(NR^{b32}R^{b33})$ or —$OP(O)(OR^{b34})_2$; or, $R^{b2}$ and $R^{b3}$, $R^{b6}$ and $R^{b7}$, $R^{b17}$ and $R^{b18}$, $R^{b24}$ and $R^{b25}$, $R^{b29}$ and $R^{b30}$, $R^{b32}$ and $R^{b33}$ together with the N to which they are attached form a substituted or unsubstituted 3-10 membered heterocyclyl, the substituent in the substituted heterocyclyl is one or more than one $R^{a6}$ (the number of the substituent is preferably 1 to 4), when there are more substituents than one, the substituents are the same or different; the substituted or unsubstituted 3-10 membered heterocyclyl refers to be a substituted or unsubstituted 3-10 membered heterocyclyl having 1-5 heteroatoms selected from the group consisting of O, N and S;

each of $R^4$ and $R^5$ is independently hydrogen, deuterium, halogen, cyano, nitro, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-8}$ cycloalkyl, substituted or unsubstituted $C_{3-8}$ cycloalkenyl, substituted or unsubstituted 3-10 membered heterocyclyl, substituted or unsubstituted aryl, substituted or unsubstituted heteroaryl or —$R^{100}$; the substituent in the substituted $C_{1-6}$ alkyl is selected from the group consisting of deuterium, halogen, $C_{3-8}$ cycloalkyl, $C_{3-8}$ cycloalkyl substituted by 1 to 3 $R^{101}$ and/or $R^{121}$, $C_{3-8}$ cycloalkenyl, $C_{3-8}$ cycloalkenyl substituted by 1 to 3 $R^{102}$ and/or $R^{122}$, 3-10 membered heterocyclyl, 3-10 membered heterocyclyl substituted by 1 to 3 $R^{103}$ and/or $R^{123}$, aryl, aryl substituted by 1 to 3 $R^{104}$ and/or $R^{124}$, heteroaryl, heteroaryl substituted by 1 to 3 $R^{105}$ and/or $R^{125}$, $R^{106}$ and $R^{126}$; the substituent in the substituted $C_{2-8}$ alkenyl, the substituted $C_{2-8}$ alkynyl, the substituted $C_{3-8}$ cycloalkyl, the substituted $C_{3-8}$ cycloalkenyl, the substituted 3-10 membered heterocyclyl, the substituted aryl or the substituted heteroaryl is selected from the group consisting of $R^{107}$ and $R^{127}$ (the number of the substituent is preferably 1 to 3), when there are more substituents than one, the substituents are the same or different;

or, when $Y^1$ is $NR^3$ or $CR^4$ and $Y^2$ is $CR^5$, $R^1$ and $R^3$, $R^1$ and $R^4$, $R^4$ and $R^5$, $R^2$ and $R^3$, or $R^2$ and $R^5$ together with the atom to which they are attached form a substituted or unsubstituted 5-6 membered aromatic ring or a substituted or unsubstituted 5-6 membered heteroaromatic ring, the substituent in the substituted 5-6 membered aromatic ring or the substituted 5-6 membered heteroaromatic ring is selected from the group consisting of $R^{a5}$, $R^{108}$ and $R^{128}$ (the number of the substituent is preferably 1 to 4), when there are more substituents than one, the substituents are the same or different; the substituted or unsubstituted 5-6 membered heteroaromatic ring refers to be a substituted or unsubstituted 5-6 membered heteroaromatic ring having 1 to 3 heteroatoms selected from the group consisting of O, S and N;

each of $R^{2'}$, $R^{3'}$, $R^{4'}$ and $R^{5'}$ is independently hydrogen, deuterium, halogen, cyano, nitro, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-8}$ cycloalkyl, substituted or unsubstituted $C_{3-8}$ cycloalkenyl, substituted or unsubstituted 3-10 membered heterocyclyl, substituted or unsubstituted heteroaryl, and —$R^{11}$; the substituent in the substituted $C_{1-6}$ alkyl is selected from the group consisting of deuterium, halogen, $C_{3-8}$ cycloalkyl, $C_{3-8}$ cycloalkyl substituted by 1 to 3 $R^{109}$ and/or $R^{129}$, $C_{3-8}$ cycloalkenyl, $C_{3-8}$ cycloalkenyl substituted by 1 to 3 $R^{1010}$ or $R^{1210}$, 3-10 membered heterocyclyl, 3-10 membered heterocyclyl substituted by 1 to 3 $R^{1011}$ and/or $R^{1211}$, aryl, aryl substituted by 1 to 3 $R^{1012}$ and/or $R^{1212}$, heteroaryl, heteroaryl substituted by 1 to 3 $R^{1013}$ and/or $R^{1213}$, $R^{1014}$ and $R^{1214}$; the substituent in the substituted $C_{2-8}$ alkenyl, the substituted $C_{2-8}$ alkynyl, the substituted $C_{3-8}$ cycloalkyl, the substituted $C_{3-8}$ cycloalkenyl, the substituted 3-10 membered heterocyclyl, the substituted aryl or the substituted heteroaryl is selected from the group consisting of $R^{1015}$ and $R^{1215}$ (the number of the substituent is preferably 1 to 3);

each of $R^3$, $R^{a1-a7}$, $R^{b1-b34}$ and $R^{c1-c38}$ is independently hydrogen, $C_{1-4}$ acyl, substituted or unsubstituted $C_{1-6}$ alkyl, substituted or unsubstituted $C_{6-10}$ aryl, substituted or unsubstituted heteroaryl, substituted or unsubstituted $C_{3-8}$ cycloalkyl, substituted or unsubstituted $C_{3-8}$ cycloalkenyl or substituted or unsubstituted 3-10 membered heterocyclyl; the substituent in the substituted $C_{1-6}$ alkyl, the substituted $C_{6-10}$ aryl, the substituted heteroaryl, the substituted $C_{3-8}$ cycloalkyl, the substituted $C_{3-8}$ cycloalkenyl or the substituted 3-10 membered heterocyclyl is selected from the group consisting of halogen, deuterium, cyano, oxo

$C_{1-6}$ alkyl, $C_{1-6}$ alkyl substituted by halogen, aryl, heteroaryl, $C_{3-8}$ cycloalkyl, $C_{3-8}$ cycloalkenyl, 3-10 membered heterocyclyl, —$OR^{d1}$, —$NR^{d2}R^{d3}$, —$SR^{d4}$, —$C(O)OR^{d5}$, —$C(O)NR^{d6}R^{d7}$, —$C(O)N(R^{d8})OR^{d9}$, —$C(O)R^{d10}$, —$S(O)R^{d11}$, —$S(O)OR^{d12}$, —$S(O)NR^{d13}R^{d14}$, —$S(O)_2R^{d15}$, —$S(O)_2OR^{d16}$, —$S(O)_2NR^{d17}R^{d18}$, —$OC(O)R^{d19}$, —$OC(O)OR^{d20}$, —$OC(O)NR^{d21}R^{d22}$, —$N(R^{d23})C(O)R^{d24}$, —$N(R^{d25})C(O)OR^{d26}$, —$N(R^{d27})C(O)NR^{d28}R^{d29}$, —$N(R^{d30})S(O)_2R^{d31}$, $N(R^{d32})C(=NR^{d33})NR^{d34}$ and —$OP(O)(OR^{d35})_2$; each of $R^{d1-d35}$ is independently hydrogen, substituted or unsubstituted $C_{1-6}$ alkyl or substituted or unsubstituted $C_{3-8}$ cycloalkyl; the substituent in the substituted $C_{1-6}$ alkyl or the substituted $C_{3-8}$ cycloalkyl is selected from the group consisting of halogen, deuterium, cyano, oxo, $C_{1-6}$ alkyl and $C_{1-6}$ alkyl substituted by halogen (the number of the substituent is preferably 1 to 3); or, $R^{d2}$ and $R^{d3}$, $R^{d6}$ and $R^{d7}$, $R^{d13}$ and $R^{d14}$, $R^{d17}$ and $R^{d18}$, $R^{d21}$ and $R^{d22}$ or $R^{d28}$ and $R^{d29}$ together with the N to which they are attached form a substituted or unsubstituted 3-10 membered heterocyclyl, the substituent in the substituted 3-10 membered heterocyclyl is selected from the group consisting of $R^{a7}$ and $R^{1216}$ (the number of the substituent is preferably 1 to 4);

in the definition of ring A and ring B, the substituent in the substituted benzene ring or the substituted 5-6 membered heteroaromatic ring is selected from the group consisting of deuterium, halogen, cyano, nitro, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-8}$ cycloalkyl, substituted or unsubstituted $C_{3-8}$ cycloalkenyl, substituted or unsubstituted 3-10 membered heterocyclyl, substituted or unsubstituted aryl, substituted or unsubstituted heteroaryl and $—R^{1016}$; the substituent in the substituted $C_{1-6}$ alkyl is selected from the group consisting of deuterium, halogen, $C_{3-8}$ cycloalkyl, $C_{3-8}$ cycloalkyl substituted by 1 to 3 $R^{1017}$ and/or $R^{1217}$, $C_{3-8}$ cycloalkenyl, $C_{3-8}$ cycloalkenyl substituted by 1 to 3 $R^{1018}$ and/or $R^{1218}$, 3-10 membered heterocyclyl, 3-10 membered heterocyclyl substituted by 1 to 3 $R^{1019}$ and/or $R^{1219}$, aryl, aryl substituted by 1 to 3 $R^{1020}$ and/or $R^{1220}$, heteroaryl, heteroaryl substituted by 1 to 3 $R^{1021}$ and/or $R^{1221}$, $R^{1022}$ and $R^{1222}$; the substituent in the substituted $C_{2-8}$ alkenyl, the substituted $C_{2-8}$ alkynyl, the substituted $C_{3-8}$ cycloalkyl, the substituted $C_{3-8}$ cycloalkenyl, the substituted 3-10 membered heterocyclyl, the substituted aryl or the substituted heteroaryl is selected from the group consisting of $R^{1023}$ and $R^{1223}$ (the number of the substituent is preferably 1 to 3);

each of $R^{10}$ to $R^{1023}$ and $R^{11}$ is independently $—OR^{c1}$, $—NR^{c2}R^{c3}$, $—SR^{c4}$, $—C(O)OR^{c5}$, $—C(O)NR^{c6}R^{c7}$, $—C(O)N(R^{c8})OR^{c9}$, $—C(O)R^{c10}$, $—S(O)R^{c11}$, $—S(O)OR^{c12}$, $—S(O)NR^{c13}R^{c14}$, $—S(O)_2R^{c15}$, $—S(O)_2OR^{c16}$, $—S(O)_2NR^{c17}R^{c18}$, $—OC(O)R^{c19}$, $—OC(O)OR^{c20}$, $—OC(O)NR^{c21}R^{c22}$, $—N(R^{c23})C(O)R^{c24}$, $—N(R^{c25})C(O)OR^{c26}$, $—N(R^{c27})C(O)NR^{c28}R^{c29}$, $—N(R^{c30})S(O)_2R^{c31}$, $—N(R^{c32})S(O)_2NR^{c33}R^{c34}$, $—P(O)(OR^{c35})(NR^{c36}R^{c37})$ or $—OP(O)(OR^{c38})_2$; or, $R^{c2}$ and $R^{c3}$, $R^{c6}$ and $R^{c7}$, $R^{c13}$ and $R^{c14}$, $R^{c17}$ and $R^{c18}$, $R^{c21}$ and $R^{c22}$, $R^{c28}$ and $R^{c29}$, $R^{c33}$ and $R^{c34}$, or $R^{c36}$ and $R^{c37}$ together with the N to which they are attached form a substituted or unsubstituted 3-10 membered heterocyclyl, the substituent in the substituted 3-10 membered heterocyclyl is one or more than one $R^{a6}$ (the number of the substituent is preferably 1 to 4); when there are more substituents than one, the substituents are the same or different; the substituted or unsubstituted 3-10 membered heterocyclyl refers to be a substituted or unsubstituted 3-10 membered heterocyclyl having 1-5 heteroatoms selected from the group consisting of O, N and S;

each of $R^{12}$ to $R^{1223}$ is independently halogen, deuterium, cyano, oxo, $C_{1-6}$ alkyl or $C_{1-6}$ alkyl substituted by halogen;

when ring Z is pyridine ring, $R^2$, $R^4$ and $R^5$ are hydrogen, $R^3$ is hydrogen or methyl. $R^1$, $R^2$ and $R^4$ are hydrogen, and $R^5$ is hydrogen or $—CH_2CH_2COOH$, the moiety

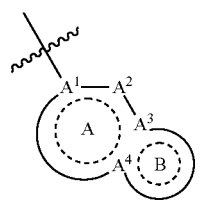

is not

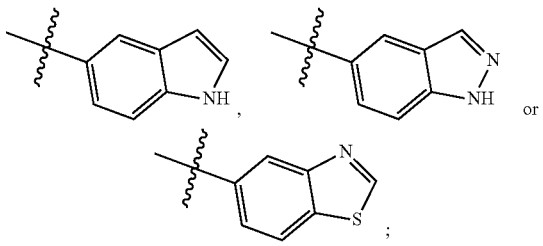

when ring Z is pyrimidine ring, $Z^4$ is N, ring B is a 5-6 membered heteroaromatic ring having one N, and $R^1$ is hydrogen, $R^4$ is not $—NR^{c2}R^{c3}$;

when $Z^3$ is S, $Z^2$ is $CR^{2'}$, $Z^4$ is $CR^{4'}$, and ring Q is benzene ring, $R^{4'}$ is not $—NR^{c2}R^{c3}$ or $—N(R^{c23})C(O)R^{c24}$;

when ring Q is benzene ring, $R^2$ is not $—CH(CO_2H)OC(CH_3)_3$;

when ring Q is benzene ring, and ring Z is tetrazole ring, ring B is not substituted by $—CF_3$ or the moiety

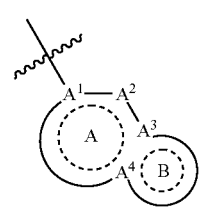

is not

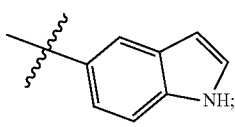 [SMILES: *c1ccc2[nH]ccc2c1]

when $Z^2$ is S, $Z^4$ is N, and ring Q is benzene ring, the moiety when $Z^2$ is O, $Z^4$ is N, ring Q is benzene ring, and ring A is a 5-membered heteroaromatic ring, ring A is not substituted by $—NR^{c2}R^{c3}$;

when $Z^1$ is N, $Z^2$ is $CR^{2'}$, $Z^3$ is $CR^{3'}$, $Z^4$ is $CR^{4'}$, and ring Q is benzene ring, the moiety is not

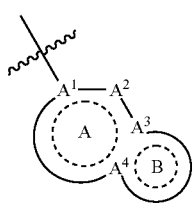

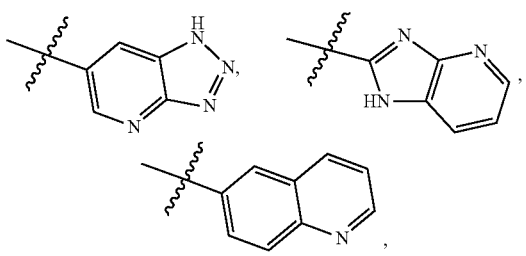

when $Z^1$ is C, $Z^2$ is NR, $Z^3$ is $CR^{3'}$, $Z^4$ is $CR^{4'}$, and ring Q is benzene ring, the moiety

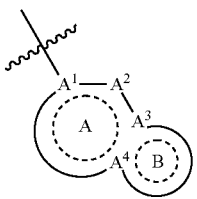

is not

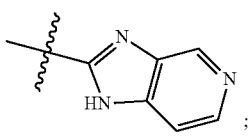 [SMILES: *c1nc2cnccc2[nH]1]

when $Z^2$ is O, $Z^3$ is $CR^{3'}$, $Z^4$ is $CR^{4'}$, and ring Q is benzene ring, the moiety

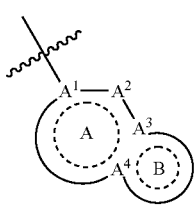 is not 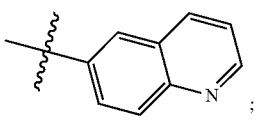;

when $Z^2$ is S, $Z^3$ is $CR^{3'}$, $Z^4$ is $CR^{4'}$, ring Q is benzene ring, and ring B is a 6-membered nitrogenous heteroaromatic ring, ring B is not substituted by —$NR^{c2}R^{c3}$;

when $Z^2$ is S, $Z^3$ is $CR^{3'}$, $Z^4$ is $CR^{4'}$, $R^1$ is hydrogen, and $Y^2$ is N, $R^4$ is not —$NR^{c2}R^{c3}$ or —$N(R^{c27})C(O)NR^{c28}R^{c29}$.

In a preferred embodiment of the present invention, in the definition of $R^3$, $R^{a1-a7}$, $R^{b1-b34}$, $R^{c1-c38}$, the substituent in the substituted $C_{1-6}$ alkyl, the substituted $C_{6-10}$ aryl, the substituted heteroaryl, the substituted $C_{3-8}$ cycloalkyl, the substituted $C_{3-8}$ cycloalkenyl or the substituted 3-10 membered heterocyclyl can also be aryl substituted by halogen.

In a preferred embodiment of the present invention, each of $R^{10}$ to $R^{1023}$ and $R^{11}$ is independently oxo

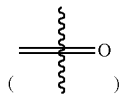

or —$C(NH)NR^{c2}R^{c3}$, wherein $R^{c2}$ and $R^{c3}$ are defined as above.

In the definition of the above groups or letters:

the 3-10 membered heterocyclyl, the 3-10 membered heterocyclyl contained in the substituted or unsubstituted 3-10 membered heterocyclyl and the 3-10 membered heterocyclyl contained in the 3-10 membered heterocyclyl substituted by 1 to 3 $R^{10x1}$ and/or $R^{12x1}$ are each independently preferably a 3-10 membered heterocyclyl having 1-4 heteroatoms independently selected from the group consisting of N, O and S; x1 is 3, 11 or 19; the 3-10 membered heterocyclyl is preferably morpholinyl

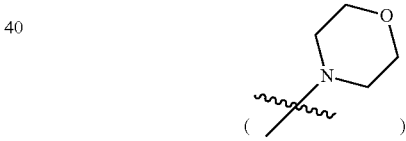

or tetrahydro-2H-pyranyl);

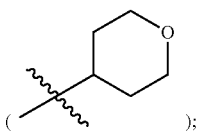

the aryl, the aryl contained in the substituted or unsubstituted aryl and the aryl contained in the aryl substituted by 1 to 3 $R^{10x2}$ and/or $R^{12x2}$ are each independently preferably $C_6$-$C_{10}$ aryl; x2 is 4, 12 or 20; the $C_6$-$C_{10}$ aryl is preferably phenyl or naphthyl;

the heteroaryl, the heteroaryl contained in the substituted or unsubstituted heteroaryl and the heteroaryl contained in the heteroaryl substituted by 1 to 3 $R^{10x3}$ and/or $R^{12x3}$ are each independently preferably a $C_1$-$C_{10}$ heteroaryl having 1-4 heteroatoms selected from the group consisting of N, O and S; x3 is 5, 13 or 21; the heteroaryl is preferably

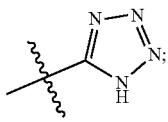 [SMILES: *c1nnn[nH]1]

the halogen is preferably F, Cl, Br or I;

the $C_{1-4}$ acyl is preferably formyl (—CHO), acetyl (—COCH$_2$), propionyl (—COCH$_2$CH$_3$) or butyryl (—COCH$_2$CH$_2$CH$_3$);

the $C_{1-6}$ alkyl contained in the substituted or unsubstituted $C_{1-6}$ alkyl and the $C_{1-6}$ alkyl are each independently preferably methyl, ethyl, n-propyl, isopropyl, n-butyl, isobutyl, tert-butyl, n-pentyl, isopentyl, neopentyl, n-hexyl, 2-methylpentyl, 3-methylpentyl, 2,2-dimethylbutyl or 2,3-dimethylbutyl;

the $C_{3-8}$ cycloalkyl, the $C_{3-8}$ cycloalkyl contained in the substituted or unsubstituted $C_{3-8}$ cycloalkyl, and the $C_{3-8}$ cycloalkyl contained in the $C_{3-8}$ cycloalkyl substituted by 1 to 3 $R^{10x4}$ and/or $R^{12x4}$ are independently preferably cyclopropyl, cyclobutyl, cyclopentyl or cyclohexyl; x4 is 1, 9, or 17;

the $C_{2-8}$ alkenyl and the $C_{2-8}$ alkenyl contained in the substituted or unsubstituted $C_{2-8}$ alkenyl are each independently preferably $C_2$-$C_4$ alkenyl; the $C_2$-$C_4$ alkenyl is preferably vinyl, allyl, propenyl, 1-butenyl, 2-butenyl or 2-methylpropenyl;

the $C_{2-8}$ alkynyl and the $C_{2-8}$ alkynyl contained in the substituted or unsubstituted $C_{2-8}$ alkynyl are each independently preferably $C_2$-$C_4$ alkynyl; the $C_2$-$C_4$ alkynyl is preferably ethynyl, propynyl, 1-butynyl, 2-butynyl or 3-methylpropynyl;

the $C_{3-8}$ cycloalkenyl and the $C_{3-8}$ cycloalkenyl contained in the substituted or unsubstituted $C_{3-8}$ cycloalkenyl are each independently preferably cyclopropenyl, cyclobutenyl, cyclopentenyl, and cyclohexenyl, cycloheptenyl, 1,3-cyclohexadienyl or 1,4-cyclohexadienyl; x5 is 2, 10 or 18.

In the definition of ring Z, the 5-6 membered heteroaromatic ring having at least one N is preferably a 5-6 membered heteroaromatic ring having 1-3 heteroatoms wherein the heteroatom is N, or selected from the group consisting of N and O, the group consisting of N and S, or the group consisting of N, O and S.

In a preferred embodiment of the present invention, in the moiety

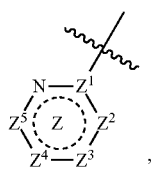

$Z^1$ is N or C; $Z^2$ is S, O, N or $CR^{2'}$; $R^{2'}$ is H or halogen; $Z^3$ is S, N or $CR^{3'}$, $R^{3'}$ is H; $Z^4$ is S, N, $NR^{a3}$ or $CR^{4'}$, $R^{a3}$ is hydrogen or $C_{1-6}$ alkyl, $R^{4'}$ is hydrogen, $C_{1-6}$ alkyl or halogen; $Z^5$ is $CR^{5'}$ or a single bond, $R^{5'}$ is hydrogen, substituted or unsubstituted $C_{1-6}$ alkyl or —$R^{11}$, wherein the substituent in the substituted $C_{1-6}$ alkyl is selected from the group consisting of deuterium and halogen; $R^{11}$ is —$OR^{c1}$, $R^{c1}$ is $C_{1-6}$ alkyl. In the definition of $R^5$, the substituted $C_{1-6}$ alkyl is preferably

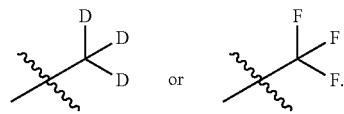 [SMILES: *C([2H])([2H])[2H] ; "or" ; *C(F)(F)F]

In a preferred embodiment of the present invention, in the definition of ring Z, the 5-6 membered heteroaromatic ring having at least one N is preferably pyridine ring, pyrazole ring or thiazole ring.

In a preferred embodiment of the present invention, the moiety

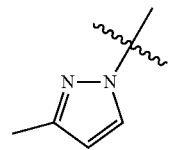

is preferably

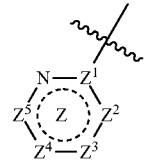

In a preferred embodiment of the present invention, the 5-6 membered heteroaromatic ring having at least one N is preferably pyridine ring, pyrazine ring, oxazole ring or 1,2,4-oxadiazole ring.

In a preferred embodiment of the present invention, the moiety

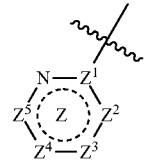

is preferably

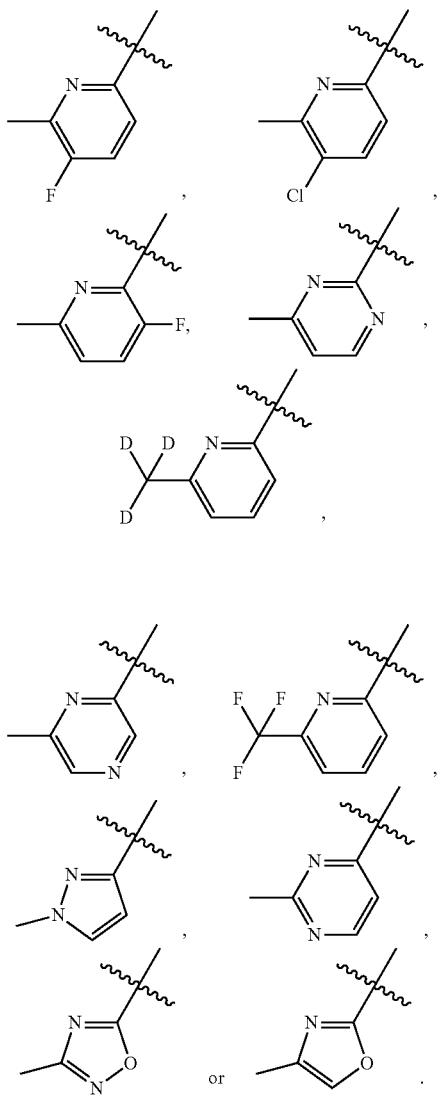

In the definition of ring Q, the 5-6 membered heteroaromatic ring is preferably 5-6 membered heteroaromatic ring having 1 to 3 heteroatoms selected from the group consisting of N, O and S.

In a preferred embodiment of the present invention, in the moiety

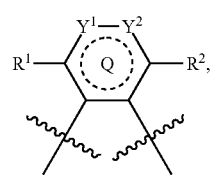

$Y^2$ can also be $NR^{5y1}$; wherein $R^{5y1}$ is defined as $R^5$. When $Y^1$ is $CR^4$ and $Y^2$ is $NR^{5y1}$, $R^4$ and $R^{5y1}$ together the atom to which they are attached form a substituted or unsubstituted 5-6 membered heteroaromatic ring, the substituent attached to the 5-6 membered heteroaromatic ring is selected from the group consisting of $R^{a5}$, $R^{108}$ and $R^{128}$ (the number of the substituent is preferably 1 to 4); when there are more substituents than one, the substituents are the same or different; the substituted or unsubstituted 5-6 membered heteroaromatic ring refers to be a substituted or unsubstituted 5-6 membered heteroaromatic ring having 1-3 heteroatoms selected from the group consisting of O, S and N. When $Y^1$ is $CR^4$ and $Y^2$ is $NR^{5y1}$, $R^4$ and $R^{5y1}$ together with the atom to which they are attached form imidazole ring.

In a preferred embodiment of the present invention, in the moiety

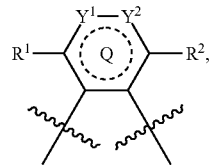

$Y^1$ is S or $CR^4$; $R^4$ is hydrogen or halogen; $Y^2$ is N, $CR^5$ or a single bond, $R^5$ is hydrogen, halogen, cyano or $-R^{100}$; $-R^{100}$ is $-OR^{c1}$, $-C(O)OR^{c5}$, $-C(O)NR^{c6}R^{c7}$ or $-C(O)R^{c10}$, $R^{c1}$ is substituted or unsubstituted $C_{1-6}$ alkyl, or substituted or unsubstituted $C_{6-10}$ aryl; $R^{c5}$ is $C_{1-6}$ alkyl; $R^{c6}$ and $R^{c7}$ are hydrogen; $R^{c10}$ is $C_{1-6}$ alkyl; the substituent in the substituted $C_{1-6}$ alkyl is selected from the group consisting of aryl or aryl substituted by halogen; the substituent in the substituted $C_{6-10}$ is one or more than one halogen; $R^1$ is hydrogen or halogen; $R^2$ is hydrogen.

In a preferred embodiment of the present invention, in the moiety

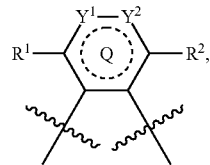

when $R^5$ is $-R^{100}$ and $-R^{100}$ is $-OR^{c1}$, in the definition of $R^{c1}$, the substituted $C_{1-6}$ alkyl is preferably

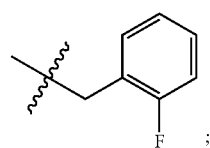 [SMILES: *Cc1ccccc1F]

the substituted $C_{6-10}$ aryl is preferably

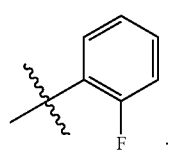 [SMILES: *c1ccccc1F]

In the definition of ring Q, the 5-6 membered heteroaromatic ring is preferably pyridine ring.

In a preferred embodiment of the present invention, the moiety

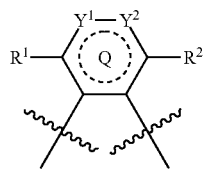

is preferably

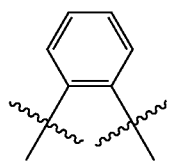 [SMILES: *c1ccccc1*]

($R^1$ and $R^2$ are hydrogen, $Y^1$ and $Y^2$ is CH),

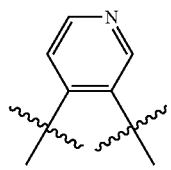 [SMILES: *c1ccncc1*]

($R^1$ and $R^2$ is hydrogen, $Y^1$ is CH, $Y^2$ is N),

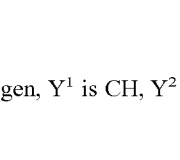

($R^1$ and $R^2$ is hydrogen, $Y^1$ is CH, $Y^2$ is $CR^5$, $R^5$ is cyano) or

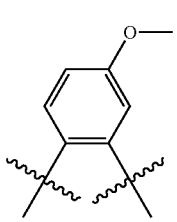 [SMILES: *c1ccc(OC)cc1*]

($R^1$ and $R^2$ is hydrogen, $Y^1$ is CH, $Y^2$ is $CR^5$, $R^5$ is —$R^{100}$, —$R^{100}$ is —$OR^{c1}$, $R^{c1}$ is methyl).

In a preferred embodiment of the present invention, the moiety

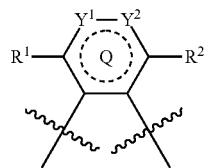

is more preferably

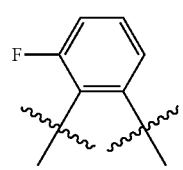 [SMILES: *c1cccc(F)c1*]

($R^1$ is F, $R^2$ is hydrogen; $Y^1$ and $Y^2$ are CH),

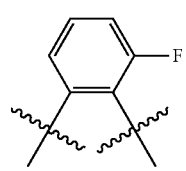 [SMILES: *c1cccc(F)c1*]

($R^1$ is hydrogen, $R^2$ is F; $Y^1$ and $Y^2$ are CH),

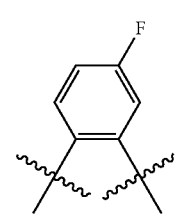 [SMILES: *c1ccc(F)cc1*]

($R^1$ and $R^2$ are hydrogen, $Y^1$ is CH, $Y^2$ is $CR^5$, $R^5$ is F),

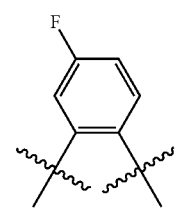 [SMILES: *c1ccc(F)cc1*]

($R^1$ and $R^2$ are hydrogen, $Y^2$ is CH, $Y^1$ is $CR^4$, $R^4$ is F),

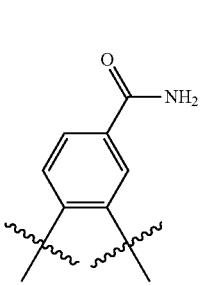 [SMILES: *c1ccc(C(N)=O)cc1*]

($R^1$ and $R^2$ are hydrogen, $Y^1$ is CH, $Y^2$ is $CR^5$, $R^5$ is —$R^{100}$, —$R^{100}$ is —C(O)$NR^{c6}R^{c7}$, $R^{c6}$ and $R^{c7}$ are hydrogen),

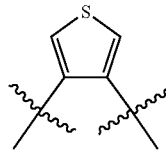 [SMILES: *c1cscc1*]

($R^1$ and $R^2$ are hydrogen, $Y^1$ is S, $Y^2$ is a single bond),

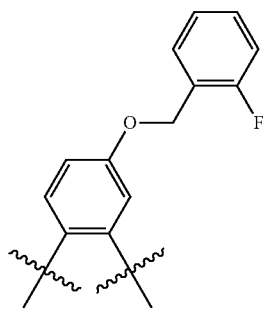 [SMILES: *c1ccc(OCc2ccccc2F)cc1*]

($R^1$ and $R^2$ are hydrogen, $Y^1$ is CH, $Y^2$ is $CR^5$, $R^5$ is —$R^{100}$, —$R^{100}$ is —$OR^{c1}$, $R^{c1}$ is

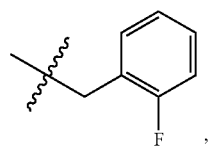

which is $C_{1-6}$ alkyl substituted by "aryl substituted by halogen"),

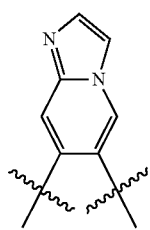 [SMILES: *c1cc2nccn2cc1*]

—N($R^1$ and $R^2$ are hydrogen; $Y^1$ is $CR^4$, $Y^2$ is $NR^{5y1}$, $R^4$ and $R^{5y1}$ together with the atom to which they are attached form imidazole ring),

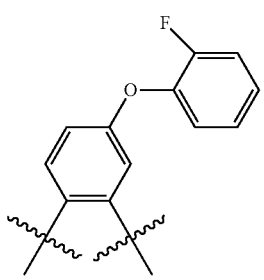 [SMILES: *c1ccc(Oc2ccccc2F)cc1*]

($R^1$ and $R^2$ are hydrogen, $Y^1$ is CH, $Y^2$ is $CR^5$, $R^5$ is —$R^{100}$, —$R^{100}$ is —$OR^{c1}$, $R^{c1}$ is

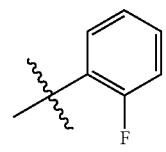 [SMILES: *c1ccccc1F]

which is aryl substituted by halogen),

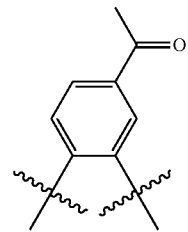 [SMILES: *c1ccc(C(C)=O)cc1*]

($R^1$ and $R^2$ are hydrogen, $Y^1$ is CH, $Y^2$ is $CR^5$, $R^5$ is —$R^{100}$, —$R^{100}$ is —C(O)$R^{c10}$, $R^{c10}$ is methyl) or

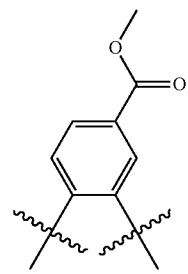 [SMILES: *c1ccc(C(=O)OC)cc1*]

($R^1$ and $R^2$ are hydrogen, $Y^1$ is CH, $Y^2$ is $CR^5$, $R^5$ is —$R^{100}$, —$R^{100}$ is —C(O)$OR^{c5}$, $R^{c5}$ is methyl).

In a preferred embodiment of the present invention, in the definition of ring A or ring B, the substituent in the substituted benzene ring or the substituted 5-6 membered heteroaromatic ring is selected from the group consisting of cyano, $C_{1-6}$ alkyl, heteroaryl and $R^{1016}$; $R^{1016}$ is —$NR^{c2}R^{c3}$, —C(O)$OR^{c5}$, —C(O)$NR^{c6}R^{c7}$, —C(O)N($R^{c8}$)$OR^{c9}$ or —S(O)$NR^{c13}R^{c14}$, wherein each of $R^{c2}$, $R^{c3}$, $R^{c5}$, $R^{c6}$, $R^{c7}$, $R^{c8}$, $R^{c9}$, $R^{c13}$ and $R^{c14}$ is independently hydrogen, $C_{1-4}$ acyl, substituted or unsubstituted $C_{1-6}$ alkyl, $C_{3-8}$ cycloalkyl or 3-10 membered heterocyclyl; the substituent in the substituted $C_{1-6}$ alkyl is selected from the group consisting of deuterium and 3-10 membered heterocyclyl, when there are more substituents than one, the substituents are the same or different. The substituted $C_{1-6}$ alkyl is preferably

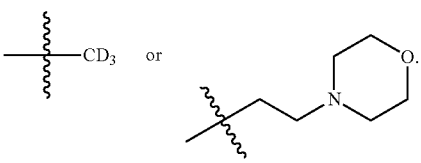 [SMILES: *C([2H])([2H])[2H] ; "or" ; *CCN1CCOCC1]

In a preferred embodiment of the present invention, in the definition of ring A or ring B, the substituent in the substituted benzene ring or the substituted 5-6 membered heteroaromatic ring is selected from the group consisting of —NR$^{c2}$R$^{c3}$, —C(O)OR$^{c5}$, —C(O)NR$^{c6}$R$^{c7}$, —C(O)N(R$^{c8}$)OR$^{c9}$ and —S(O)NR$^{c13}$R$^{c14}$, wherein, each of R$^{c2}$ and R$^{c3}$ is independently hydrogen or C$_{1-4}$ acyl; R$^{c5}$ is hydrogen or C$_{1-6}$ alkyl; each of R$^{c6}$ and R$^{c7}$ is independently hydrogen, C$_{1-4}$ acyl, substituted or unsubstituted C$_{1-6}$ alkyl, C$_{3-8}$ cycloalkyl or 3-10 membered heterocyclyl, R$^{c8}$ and R$^{c9}$ are hydrogen; R$^{c13}$ and R$^{c14}$ are hydrogen. The —NR$^{c2}$R$^{c3}$ is preferably

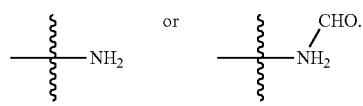

The —C(O)OR$^{c5}$ is preferably

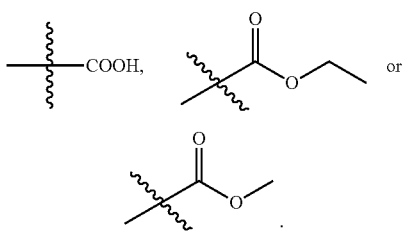

The —C(O)NR$^{c6}$R$^{c7}$ is preferably

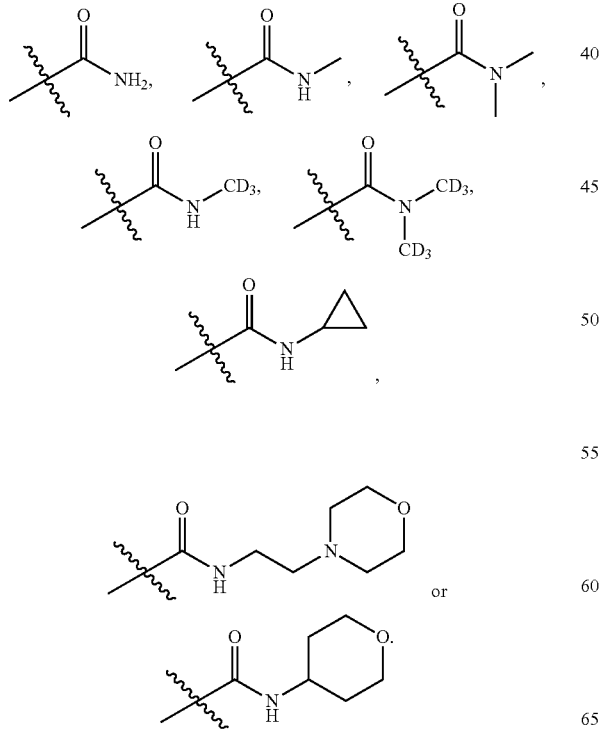

The —C(O)N(R$^{c8}$)OR$^{c}$ is preferably

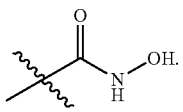 [SMILES: *C(=O)NO]

The —S(O)NR$^{c13}$R$^{c14}$ is preferably

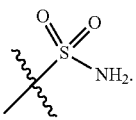

In the definition of ring A or ring B, the substituted or unsubstituted 5-6 membered heteroaromatic ring is preferably a substituted or unsubstituted 5-6 membered heteroaromatic ring having 1-4 heteroatoms selected from the group consisting of N, O and S.

In a preferred embodiment of the present invention, in the definition of ring A or ring B, the substituted or unsubstituted 5-6 membered heteroaromatic ring is preferably substituted or unsubstituted pyridine ring, substituted or unsubstituted pyrimidine ring, substituted or unsubstituted imidazole ring, substituted or unsubstituted pyrazole ring, substituted or unsubstituted triazole ring or substituted or unsubstituted furan ring.

In the definition of ring A or ring B, the substituted 5-6 membered heteroaromatic ring is preferably

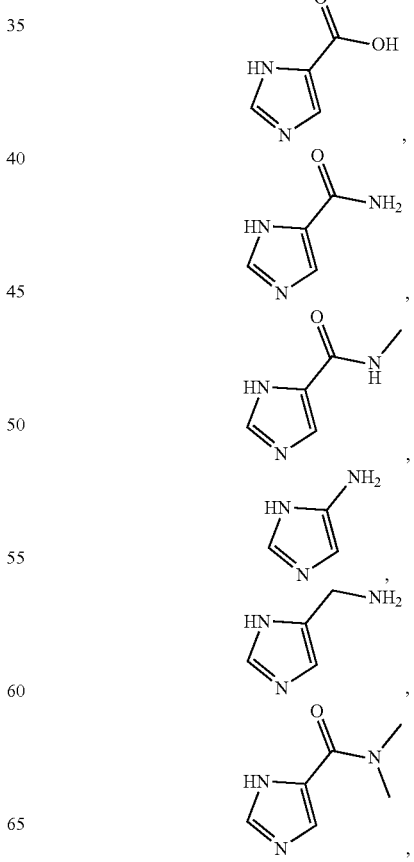

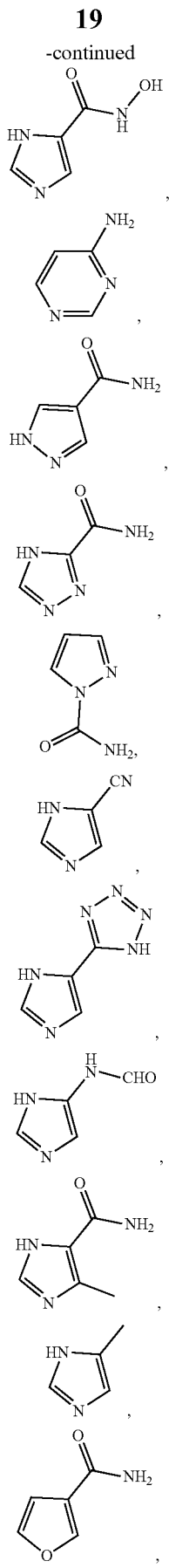
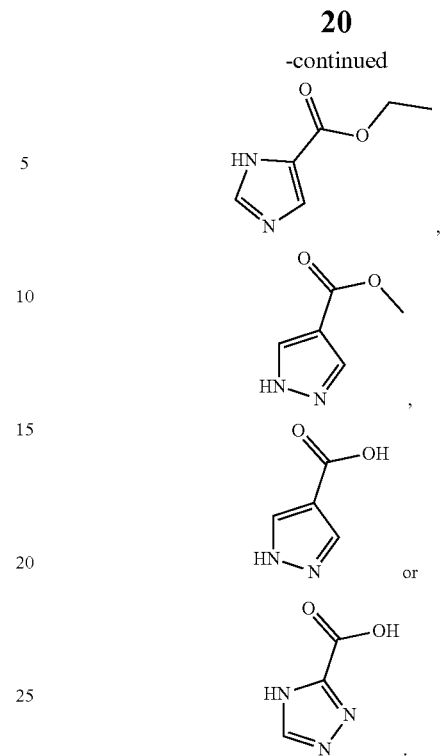
In the definition of ring A or ring B, the substituted or unsubstituted 5-6 membered heteroaromatic ring is more preferably substituted or unsubstituted pyrazine ring or substituted or unsubstituted pyridazine ring.
In the definition of ring A or ring B, the substituted 5-6 membered heteroaromatic ring is more preferably, -continued

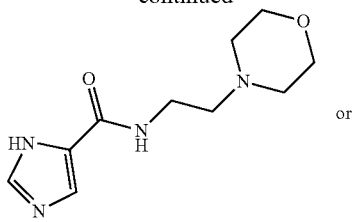 or

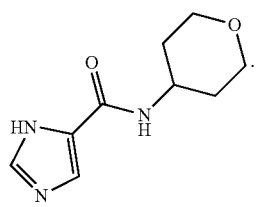

In a preferred embodiment of the present invention, in the definition of ring A, $A^1$ is C; $A^2$ is C; each of $A^3$ and $A^4$ is independently N or C, and, $A^3$ and $A^4$ are not N simultaneously.

In a preferred embodiment of the present invention, ring A is preferably pyridine ring, pyridazine ring or benzene ring; ring B is preferably substituted or unsubstituted imidazole ring, substituted or unsubstituted pyrimidine ring, substituted or unsubstituted pyridine ring, substituted or unsubstituted pyridazine ring, substituted or unsubstituted pyrazine ring, substituted or unsubstituted pyrazole ring, substituted or unsubstituted triazole ring, or, substituted or unsubstituted furan ring.

In formula I, the moiety

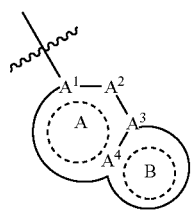

is preferably

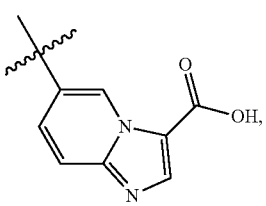 [SMILES: *c1ccc2ncc(C(=O)O)n2c1]

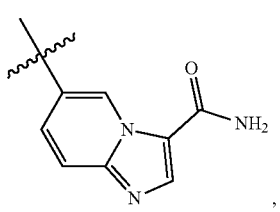

-continued

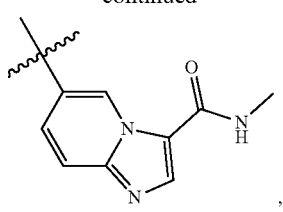

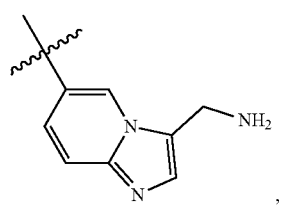

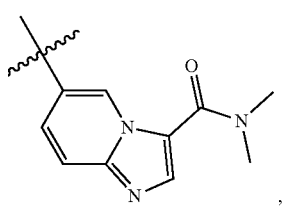

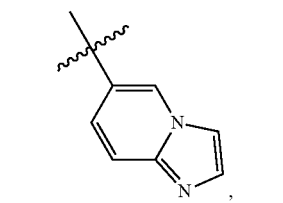

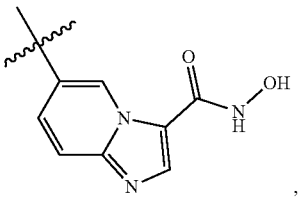

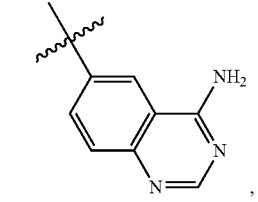

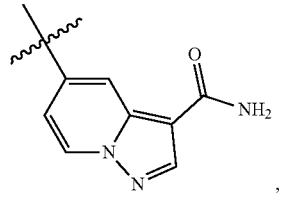

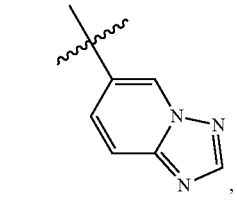

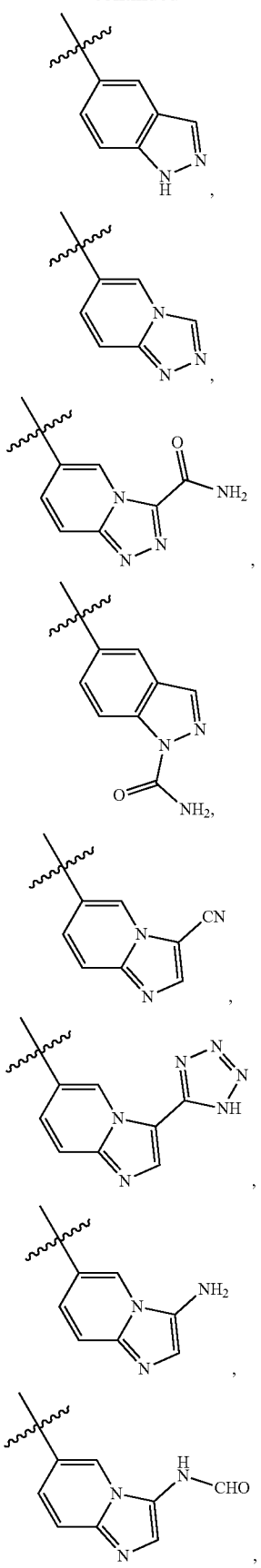
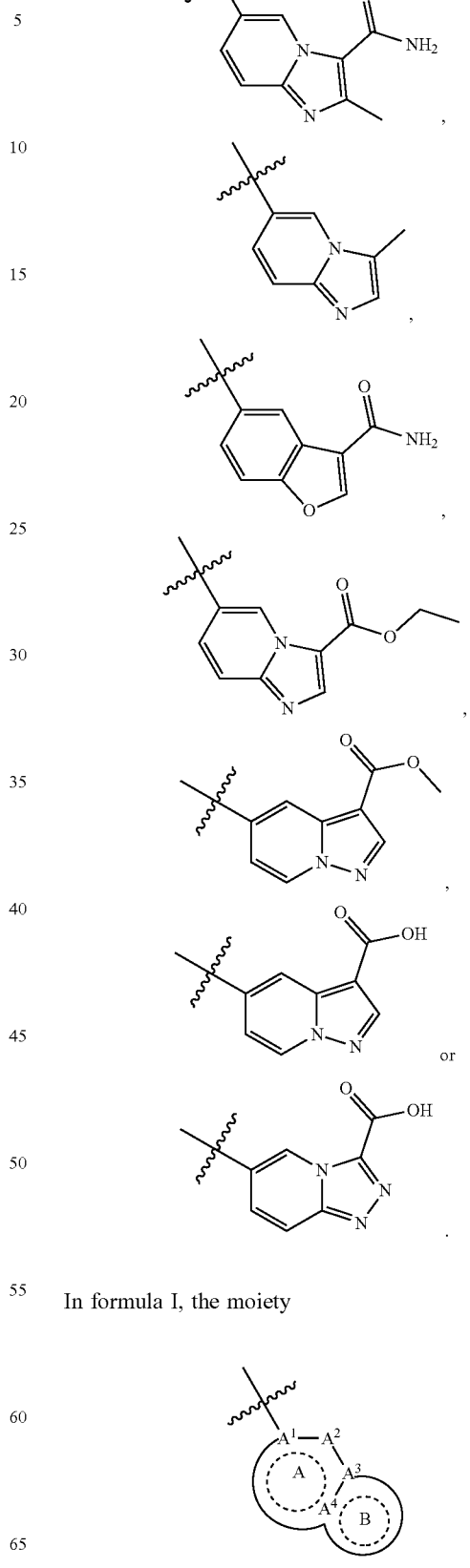
In formula I, the moiety is more preferably

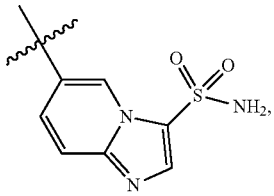 [SMILES: *c1ccc2ncc(S(N)(=O)=O)n2c1]

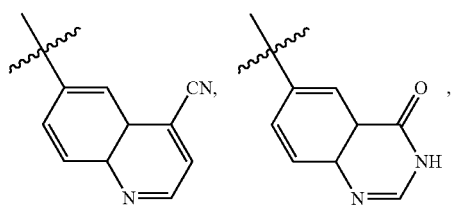

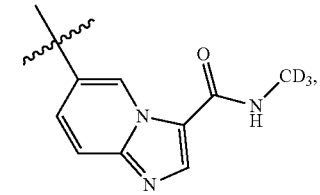

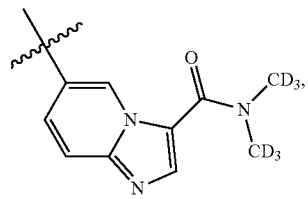

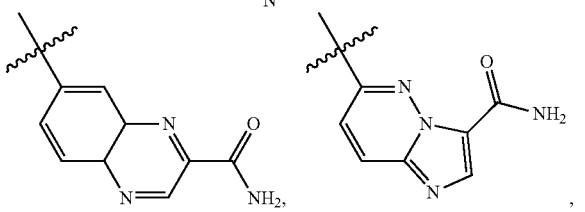

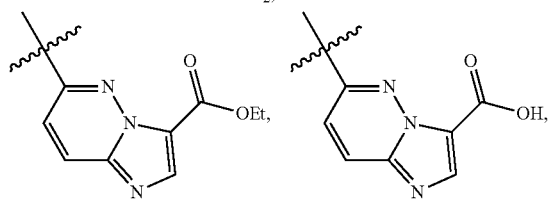

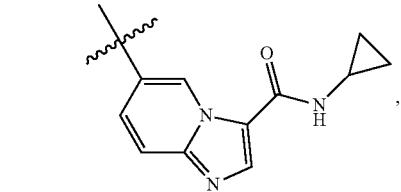

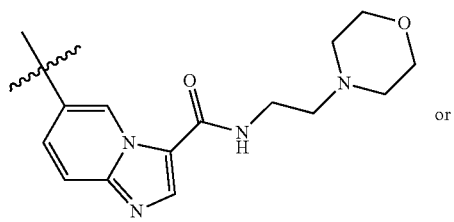

or

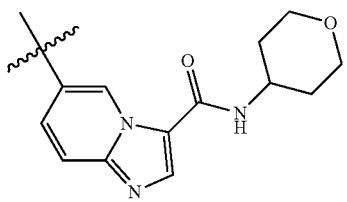

In a preferred embodiment of the present invention, in the definition of ring B, when the substituent in the substituted 5-6 membered heteroaromatic ring is substituted $C_{1-6}$ alkyl, the substituent in the substituted $C_{1-6}$ alkyl is not —NH$_2$.

In a preferred embodiment of the present invention, when ring B is a 5-6 membered heteroaromatic ring, the 5-6 membered heteroaromatic ring is not pyrazole ring.

In a preferred embodiment of the present invention, when ring B is a 5-6 membered heteroaromatic ring, the 5-6 membered heteroaromatic ring is not triazole ring (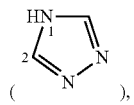), wherein, the 1-position N and 2-position C link to ring A.

In a preferred embodiment of the present invention, when ring B is a substituted 5-6 membered heteroaromatic ring, the substituted 5-6 membered heteroaromatic ring is not

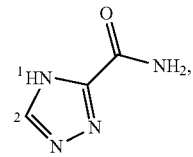

wherein, the 1-position N and 2-position C link to ring A.

In a preferred embodiment of the present invention, in the moiety

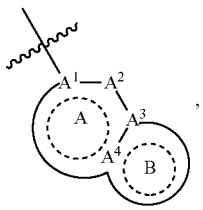

in the definition of ring B, the atoms attached to $A^3$ are carbon atoms.

In a preferred embodiment of the present invention, ring B is preferably a substituted 5-6 membered heteroaromatic ring, the substituent in the substituted 5-6 membered heteroaromatic ring is preferably located at a carbon atom (more preferably located at the carbon atom attached to $A^3$ in the moiety

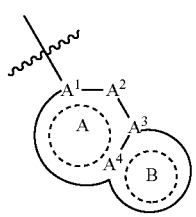

); the number of the substituent is preferably 1.

In a preferred embodiment of the present invention, $Z^1$ is preferably C; $Z^2$ is preferably S or $CR^{2'}$; $Z^3$ is preferably $CR^{3'}$; $Z^4$ is preferably $CR^{4'}$; $Z^5$ is preferably $CR^{5'}$ or a single bond; any of $R^{2'}$, $R^{3'}$, $R^{4'}$ and $R^{5'}$ is independently preferably hydrogen, substituted or unsubstituted $C_{1-6}$ alkyl or —$R^{10}$; $A^1$ is preferably C; any of $A^3$ and $A^4$ is independently preferably N or C, $A^2$ is preferably $CR^{a4}$, $CR^{10}$ or $CR^{13}$; $Y^1$ is preferably $CR^4$; $Y^2$ is preferably N or $CR^5$.

In the present invention, the nitrogenous aromatic heterocyclic compound represented by formula I is preferably selected from the group consisting of

1

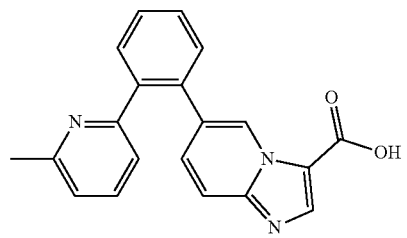

2

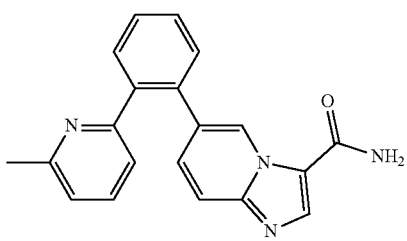

3

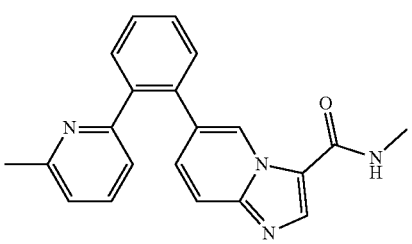

4

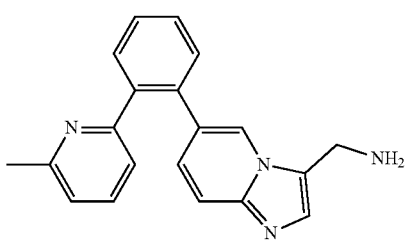

5

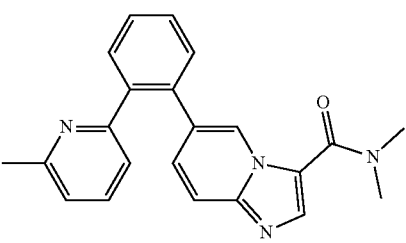

6

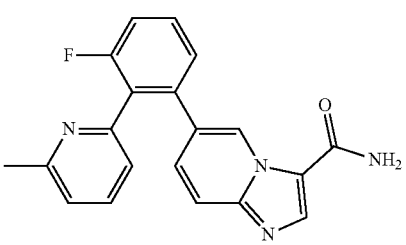

7

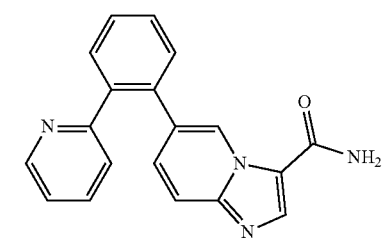

8

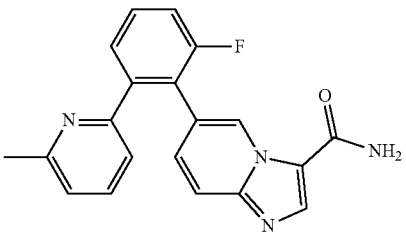

9

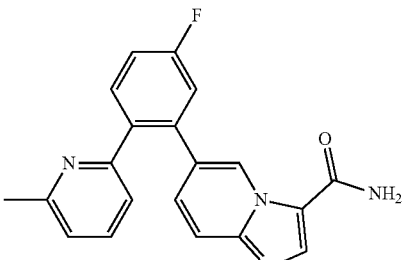

10

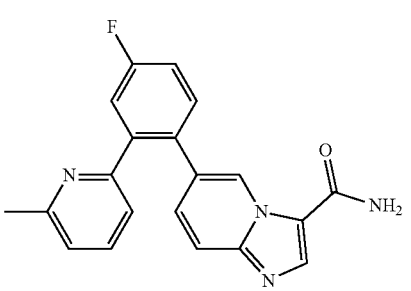

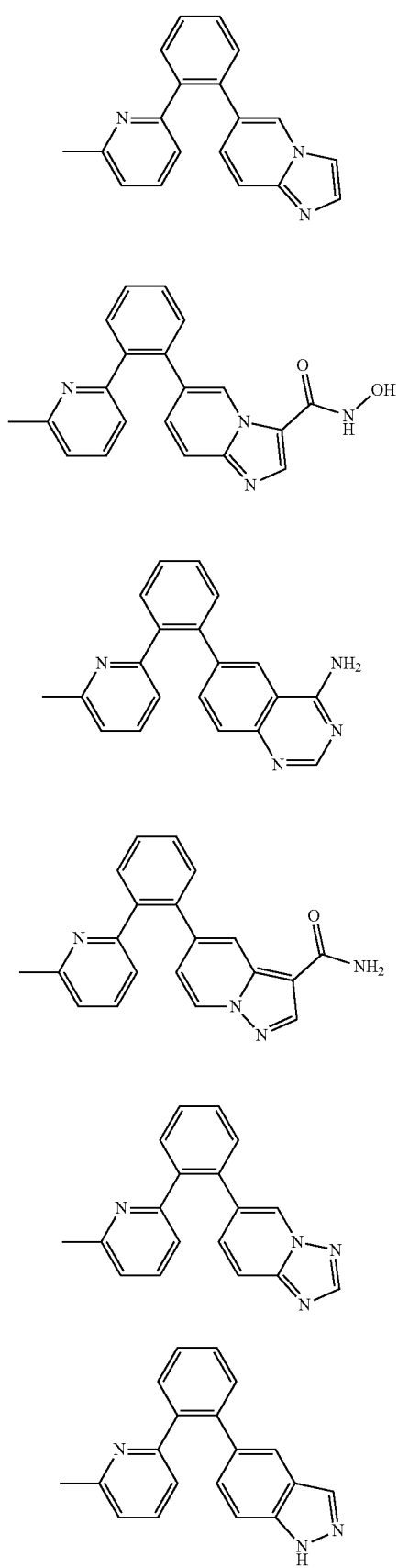
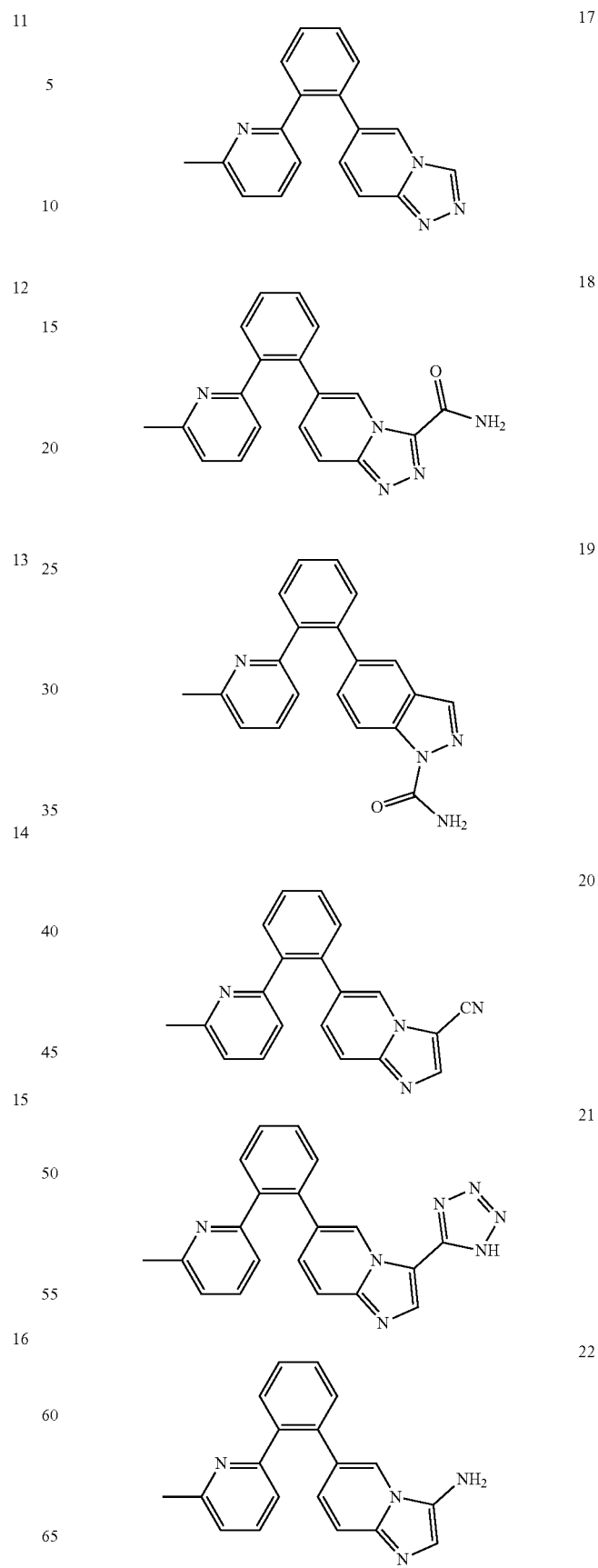

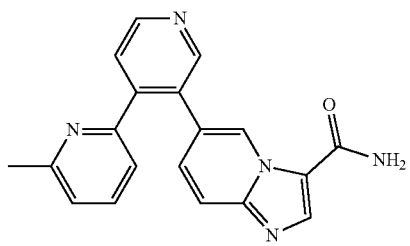
23
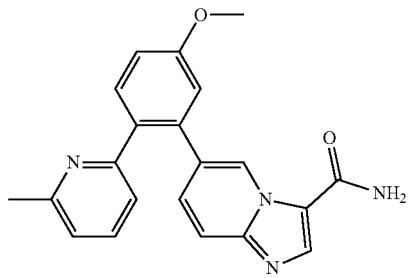
29
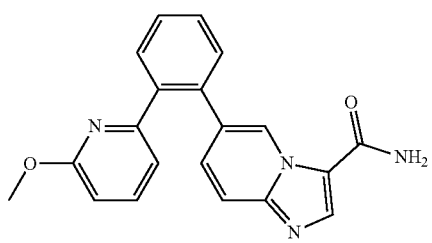
24
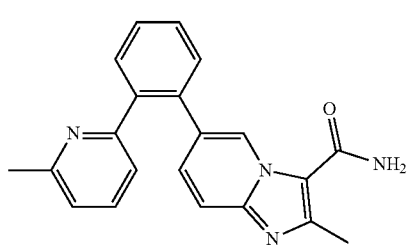
30
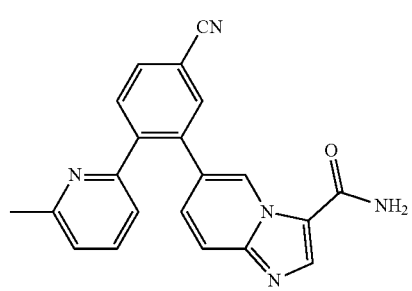
25
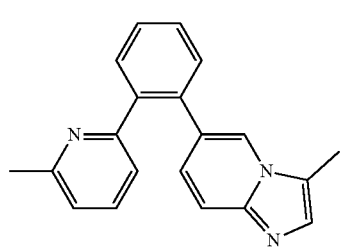
31
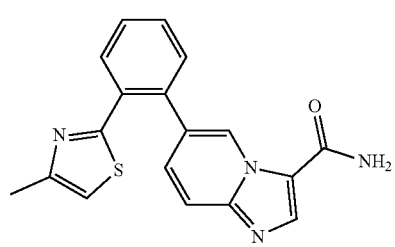
26
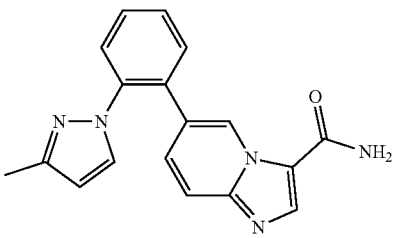
32
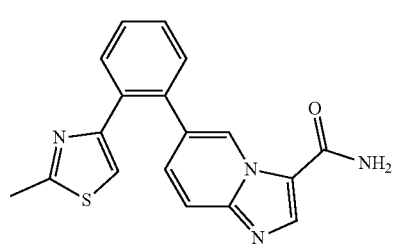
27
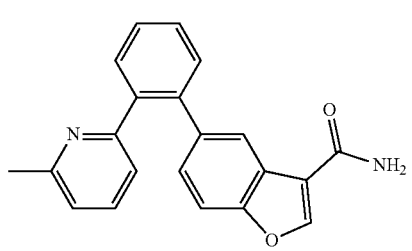
33
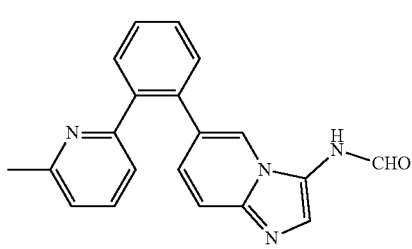
28
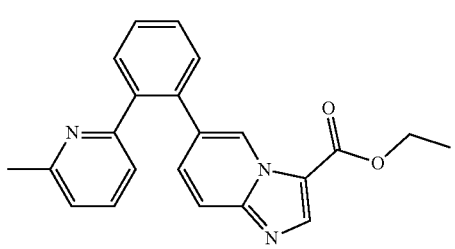
1-a

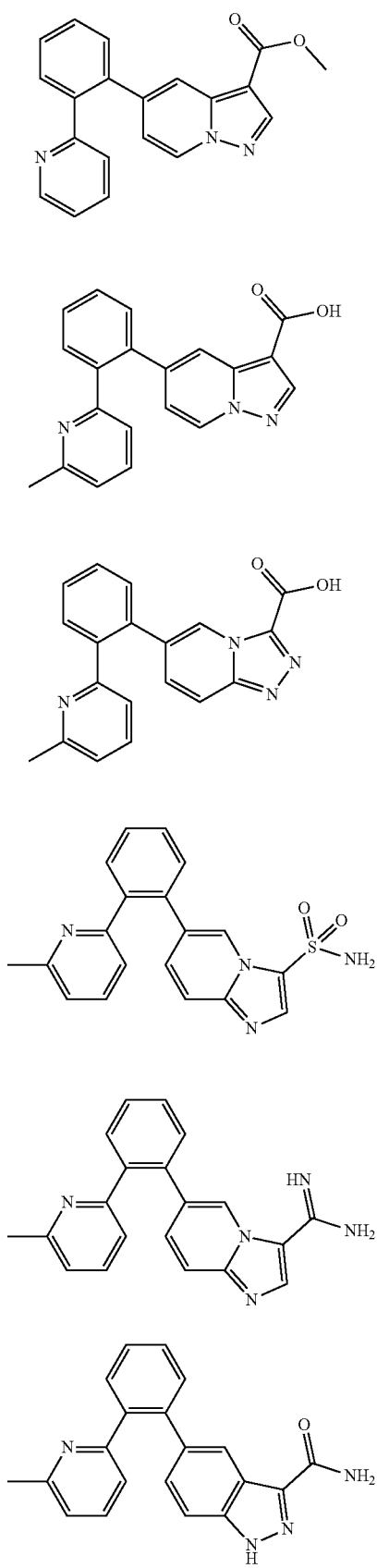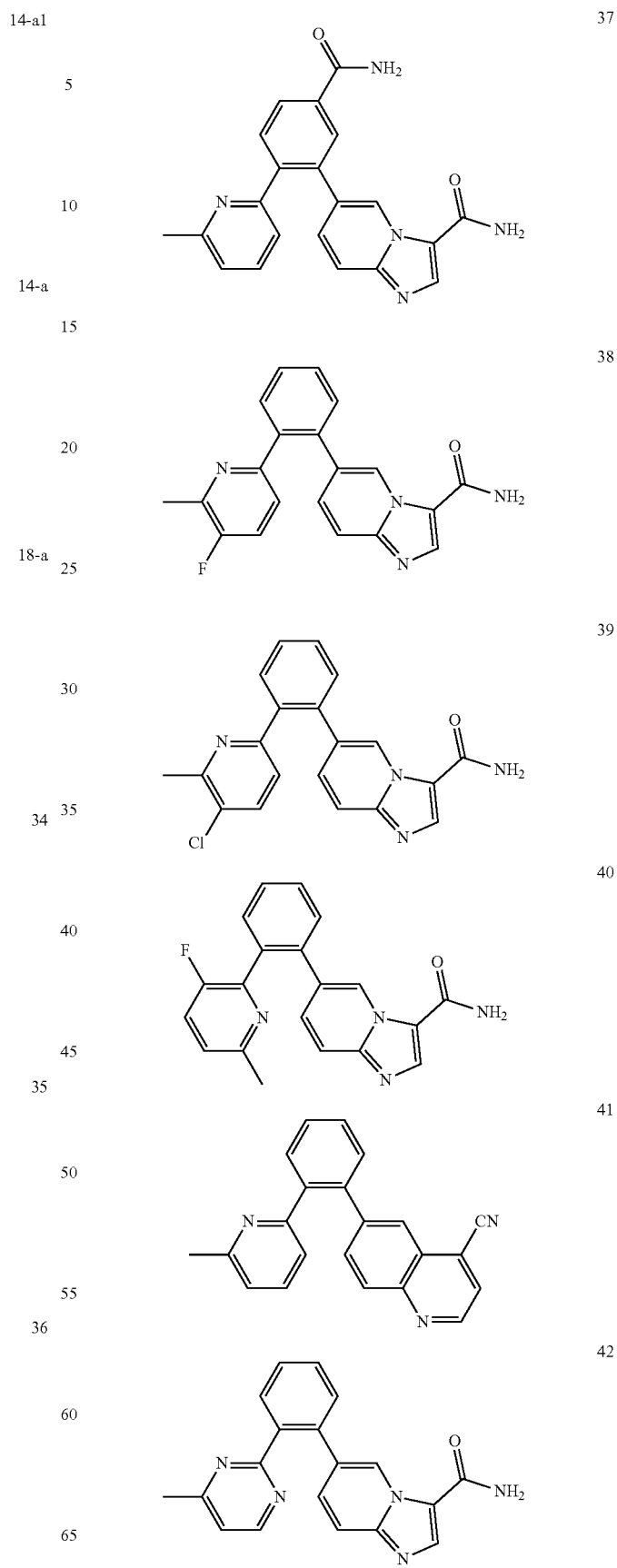

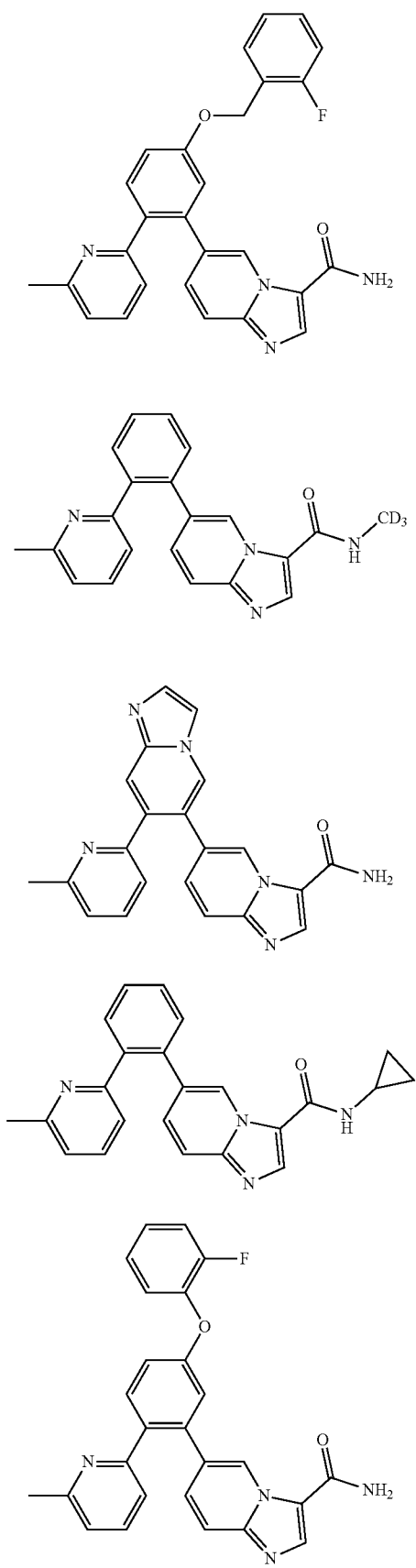
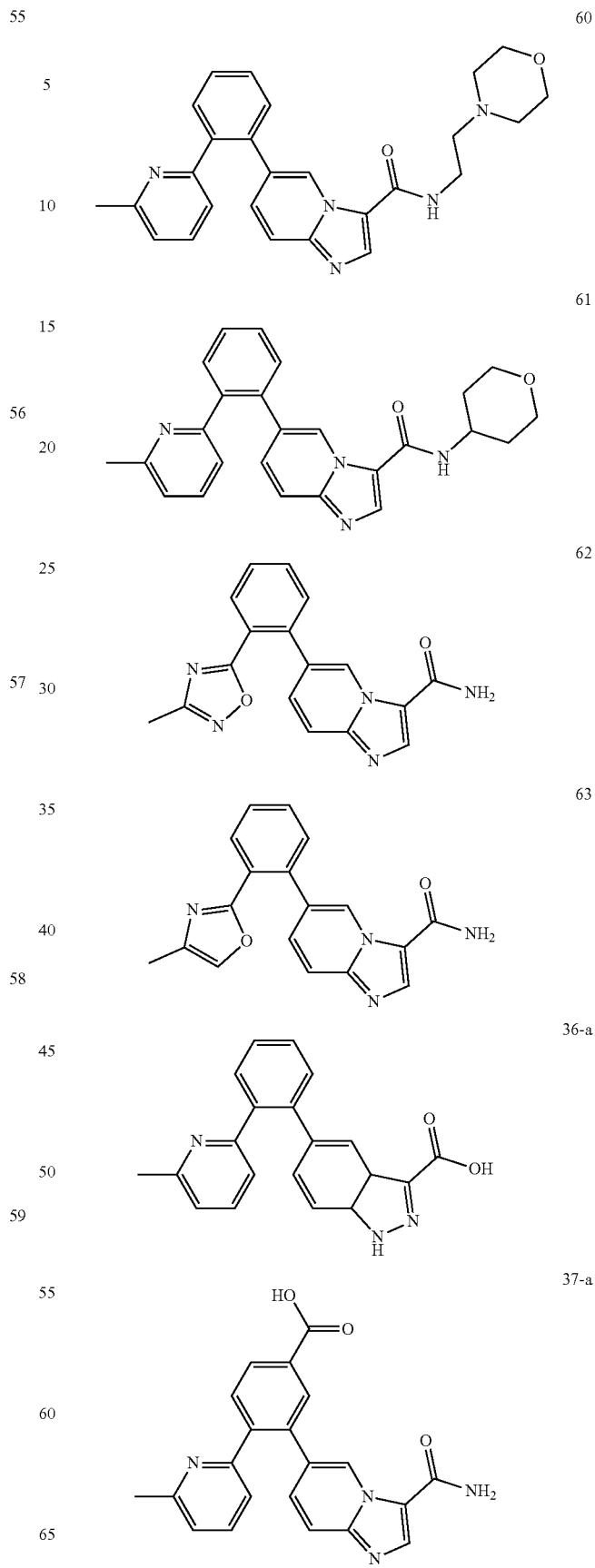

-continued

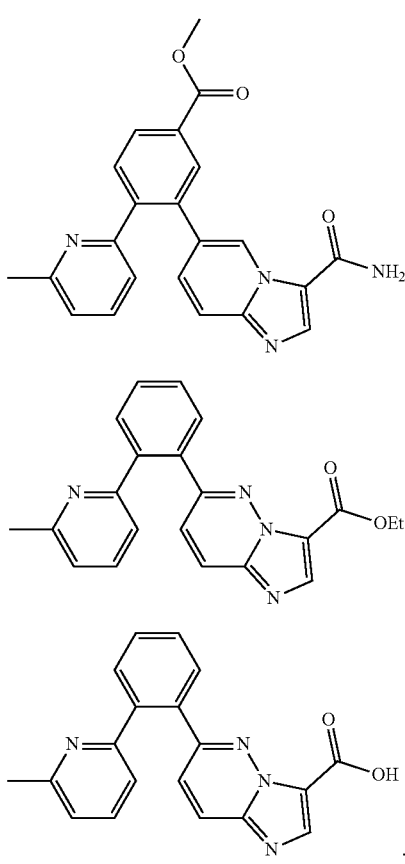

37-b 54-b 54-a

The present invention also provides a process for preparing nitrogenous aromatic heterocyclic compound represented by formula I, comprising conducting a coupling reaction of a compound represented by formula I-1 with a compound represented by formula I-2 as shown below;

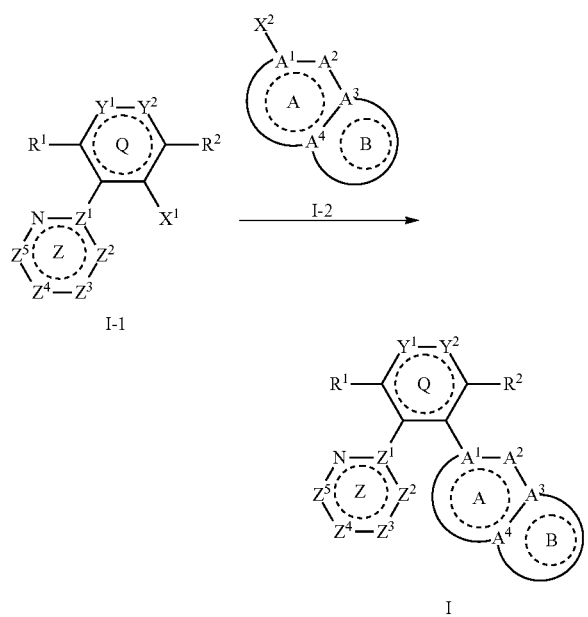

I-1

I-2

I wherein $X^1$ is Cl, Br, I or —$OSO_2CF_3$, $X^2$ is —$BF_3K$ or —$B(OR^{35})_2$;

or, $X^2$ is Cl, Br, I or —$OSO_2CF_3$, $X^1$ is —$BF_3K$ or —$B(OR^{35})_2$;

wherein $R^{35}$ is hydrogen or $C_1$-$C_6$ alkyl, or two $OR^{35}$ together with the boron atom to which they are attached form

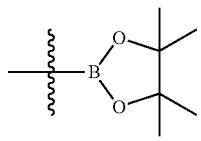

wherein $R^1, R^2, Z^1, Z^2, Z^3, Z^4, Z^5, Y^1, Y^2, A^1, A^2, A^3, A^4$, ring Z, ring Q, ring A and ring B are defined as above.

In the process for preparing nitrogenous aromatic heterocyclic compound represented by formula I, the conditions for the coupling reaction may be conventional conditions for such reactions in the art. The present invention preferably comprises conducting the coupling reaction of the compound represented by formula I-1 with the compound represented by formula I-2 in the presence of a base and a palladium catalyst in a solvent. Wherein, the solvent is preferably an organic solvent and/or water. The organic solvent may be an organic solvent commonly used in such reactions in the art, as long as it does not affect the progress of the reaction. The organic solvent is preferably selected from the group consisting of aromatics solvent, alcohols solvent, nitriles solvent and ethers solvent. The aromatics solvent is preferably toluene. The alcohols solvent is preferably $C_{1-4}$ alcohols solvent, e.g., ethanol. The nitriles solvent is preferably acetonitrile. The ethers solvent is preferably 1,4-dioxane. The amount of the solvent is not particularly limited as long as it does not affect the progress of the reaction. The palladium catalyst may be a conventional palladium catalyst for such reactions in the art, preferably tetrakis(triphenylphosphine)palladium and/or Pd(dppf)Cl$_2$. The palladium catalyst is generally used in a catalytic amount, and the molar ratio of the palladium catalyst to the compound represented by formula I-1 is preferably 0.1 to 1. The base may be a conventional base for such reactions in the art, preferably selected from the group consisting of sodium carbonate, potassium acetate and potassium phosphate. The amount of the base is not particularly limited as long as it does not affect the progress of the reaction, and the molar ratio of the base to the compound represented by formula I-1 is preferably 1:1 to 1:5, more preferably 1:2 to 1:3. The amount ratio of the compound represented by formula I-1 to the compound represented by formula I-2 is not particularly limited as long as it does not affect the progress of the reaction, and the molar ratio of the compound represented by formula I-1 to the compound represented by formula I-2 is preferably 1:0.5 to 1:2 (e.g., 1:1.2). The temperature of the coupling reaction may be a conventional temperature for such reactions in the art, preferably 50 to 100° C., more preferably 80 to 95° C. The progress of the coupling reaction can be monitored by a conventional detection method in the art (e.g., TLC, GC, HPLC or HNMR, etc.), generally disappearance of the compound of formula I-1 is seen as completion of the reaction, the duration of the coupling reaction is preferably 8 to 15 hours.

In a preferred embodiment of the invention, the coupling reaction is preferably conducted under nitrogen atmosphere.

The present invention also provides a process for preparing the nitrogenous aromatic heterocyclic compound represented by formula I, comprising conducting a coupling reaction of a compound represented by formula II-1 with a compound represented by formula II-2 as shown below;

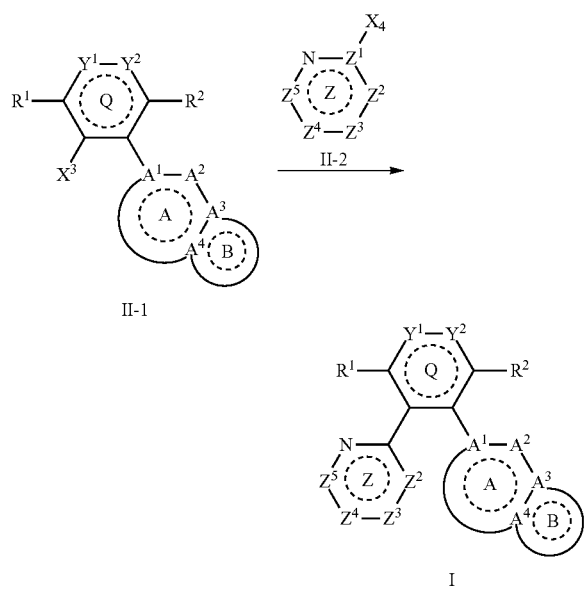

wherein, $X^3$ is Cl, Br, I or —$OSO_2CF_3$; $X^4$ is $SnBu_3$; or $X^4$ is Cl, Br, I or —$OSO_2CF_3$; $X^3$ is $SnBu_3$;

$R^1$, $R^2$, $Z^1$, $Z^2$, $Z^3$, $Z^4$, $Z^5$, $Y^1$, $Y^2$, $A^1$, $A^2$, $A^3$, $A^4$, ring Z, ring Q, ring A and ring B are defined as above.

In formula II-2, ring Z is preferably pyridine ring.

In the process for preparing the nitrogenous aromatic heterocyclic compound represented by formula I, the conditions of the coupling reaction may be conventional conditions for such reactions in the art. The present invention preferably comprises conducting the coupling reaction of the compound represented by formula II-1 with the compound represented by formula II-2 under the catalysis of palladium in a solvent. Wherein, the solvent is preferably an anhydrous organic solvent. The organic solvent may be a solvent commonly used in such reactions in the art, as long as it does not affect the progress of the reaction. The organic solvent is preferably an aromatics solvent. The aromatics solvent is preferably toluene. The amount of the solvent is not particularly limited as long as it does not affect the progress of the reaction. The palladium catalyst may be a conventional palladium catalyst for such reactions in the art, preferably tetrakis(triphenylphosphine)palladium and/or Pd(dppf)C$_{1-2}$. The palladium catalyst is generally used in a catalytic amount, and the molar ratio of the palladium catalyst to the compound represented by formula I-1 is preferably 0.1 to 1. The amount ratio of the compound represented by formula II-1 to the compound represented by formula II-2 is not particularly limited as long as it does not affect the progress of the reaction, and the molar ratio of the compound represented by formula I-1 to the compound represented by formula I-2 is preferably 1:0.5 to 1:2 (e.g., 1:1). The temperature of the coupling reaction may be a conventional temperature for such reactions in the art, preferably 50 to 100° C., more preferably 80 to 95° C. (e.g., 90° C.). The progress of the coupling reaction can be monitored by a conventional detection method in the art (e.g., TLC, GC, HPLC or HNMR, etc.), generally disappearance of the compound of formula II-1 is seen as completion of the reaction, the duration of the coupling reaction is preferably 8 to 15 hours.

In a preferred embodiment of the invention, the coupling reaction is preferably conducted under nitrogen atmosphere.

The conditions and steps for the chemical reactions involved in the various reaction routes described in the present invention can be carried out by referring to conventional conditions and steps for such reactions in the art, specifically referring to the following references: R. Larock, *Comprehensive Organic Transformations*, VCH Publishers (1989); T. W. Greene and P. G. M. Wuts, *Protective Groups in Organic Synthesis*, 3$^{rd}$ ED., John Wiley and Sons (1999); L. Fieser and M. Fieser, *Fieser and Fieser's Reagents for Organic Synthesis*, John Wiley and Sons (1994); L. Paquette, ed., *Encyclopedia of Reagents for Organic Synthesis*, John Wiley and Sons (1995) and its subsequent editions. The content of the above references is hereby incorporated by reference in its entirety. In addition, the compounds obtained according to the methods above can be further modified in peripheral positions to give other target compounds of the present invention according to the relevant methods disclosed in the above references.

At least one of the aromatic heterocyclic compound or pharmaceutically acceptable salt thereof prepared by the above methods can be purified by column chromatograph, high performance liquid chromatography, crystallization or other proper conditions. The conditions and steps used in the purification method such as column chromatograph, high performance liquid chromatography and crystallization can refer to conventional conditions and steps in the art.

The compounds described herein includes, but are not limited to, their optical isomers, racemates, and other mixtures. In these cases, a single enantiomer or diastereomer, e.g., an optically active structure, can be obtained by asymmetric synthesis or by resolution of a racemic mixture or a mixture of diastereomers. The methods for the resolution of a racemic mixture or a mixture of diastereomers can be conventional separation methods, for example, crystallization with a resolving agent or chromatography (e.g., chiral high performance liquid chromatography (HPLC) column). Additionally, such compounds include compounds having Z- and E-configuration (or cis- and tram-) C═C double bond. The compounds described herein may exist in various tautomeric forms, and the term "compound" includes all tautomers of the compound. The compounds herein also include their different crystal forms, including polycrystals and clathrates. Likewise, the term "salt" also includes all isomers of the compound, e.g., racemates, other mixtures, Z- and E-configuration, tautomers and crystalline forms.

The present invention also provides a use of the nitrogenous aromatic heterocyclic compound represented by formula I or the pharmaceutically acceptable salt thereof in manufacturing an ALK5 inhibitor or manufacturing a medicament for treating or preventing an ALK5 mediated disease.

The "ALK5 mediated disease" includes but is not limited to the group consisting of cancer, organ fibrosis, viral infection, chronic nephritis, acute nephritis, diabetic nephropathy, osteoporosis, arthritis, wound healing, ulceration, corneal trauma, heart valve stenosis, congestive cardiac necrosis, neurologic impairment, Alzheimer's syndrome, peritoneal or subcutaneous adhesions, atherosclerosis and tumor metastasis, is preferably cancer and/or organ fibrosis. The cancer includes but is not limited to the group consisting of colon cancer, pancreatic cancer, breast cancer, prostate cancer, lung cancer, brain cancer, ovarian cancer, cervical cancer, testicular cancer, kidney cancer, head or neck cancer, bone cancer, skin cancer, rectal cancer, liver cancer, colon cancer, esophagus cancer, stomach cancer, pancreatic cancer, thyroid cancer, bladder cancer, lymphoma, leukemia and melanoma. The organ fibrosis includes but is not limited to the group consisting of renal fibrosis, liver fibrosis and pulmonary fibrosis.

The present invention also provides a pharmaceutical composition comprising a prophylactically and/or therapeutically effective amount of one or more than one of the nitrogenous aromatic heterocyclic compound represented by formula I and the pharmaceutically acceptable salt thereof, and a pharmaceutically acceptable carrier.

In the present invention, the term "therapeutically effective amount" means (i) the amount of the compound of the present invention required for preventing or treating the specific disease or disorder described in the application; (ii) the amount of the compound of the present invention required for attenuating, ameliorating or eliminating one or more symptoms of the specific disease or disorder described in the application; or (iii) the amount of the compound of the present invention required for preventing or delaying the onset of one or more symptoms of the specific disease or disorder described in the application. The amount for treating human patients may range from 0.0001 mg/kg to 50 mg/kg, most commonly 0.001 mg/kg to 10 mg/kg by body weight, e.g., within the range from 0.01 mg/kg to 1 mg/kg. Such amounts may be administered, for example 1 to 5 times a day.

In the present invention, according to therapeutic purposes, the pharmaceutical composition can be formulated into various unit dosage forms such as tablets, pills, powders, liquids, suspensions, emulsions, granules, capsules, suppositories and injections (solutions and suspensions) and the like, preferably tablets, pills, granules, and capsules and the like.

In order to form a pharmaceutical composition in the form of a tablet preparation, any known and widely used excipients in the art can be used, e.g., carriers, such as lactose, white sugar, sodium chloride, glucose, urea, starch, calcium carbonate, kaolin, crystalline cellulose and silicic acid and the like; adhesives, such as water, ethanol, propanol, ordinary syrup, glucose solution, starch solution, gelatin solution, carboxymethyl cellulose, shellac, methylcellulose and potassium phosphate, polyvinylpyrrolidone and the like; disintegrants, such as dry starch, sodium alginate, agar powder and kelp powder, sodium bicarbonate, calcium carbonate, fatty acid ester of polythene dehydrated sorbitol, sodium lauryl sulfate, stearic acid monoglyceride, starch and lactose and the like; disintegration inhibitors, such as white sugar, glyceryl tristearate, coconut oil and hydrogenated oil; adsorption accelerators, such as quaternary ammonium bases and sodium lauryl sulfate and the like; wetting agents, such as glycerin, starch and the like; adsorbents, such as starch, lactose, kaolin, bentonite and colloidal silicic acid and the like; and lubricants, such as pure talc, stearates, boric acid powder and polyethylene glycol, and the like It can also be made into sugar-coated tablets, gelatin membrane-coated tablets, enteric-coated tablets, film-coated tablets, bilayer tablets and multilayered tablets by use of conventional coated materials when necessary.

In order to form the pharmaceutical composition in the form of a pill preparation, any known and widely used excipients in the art can be used, e.g, carriers, such as lactose, starch, coconut oil, hardened vegetable oil, kaolin and talc and the like; adhesives, such as gum arabic powder, tragacanth powder, gelatin and ethanol and the like; disintegrants, such as agar and kelp powder and the like.

In order to form the pharmaceutical composition in the form of a suppository preparation, any known and widely used excipients in the art can be used, e.g., polyethylene glycol, coconut oil, higher alcohols, higher alcohol esters, gelatin and semi-synthetic glycerides and the like.

In order to prepare a pharmaceutical composition in the form of an injection preparation, a solution or suspension may be sterilized (preferably by adding an appropriate amount of sodium chloride, glucose or glycerol, etc.), then prepared into a blood-isotonic injection with the isotonic pressure of the blood. Any suitable carriers in the art may also be used in the preparation of the injection. For example, water, ethanol, propanediol, ethoxylated isostearyl alcohol, polyoxylated isostearyl alcohol and polyethylene sorbitan fatty acid ester. In addition, conventional solubilizers, buffers and analgesics and the like may be added.

In the present invention, the administration route of the pharmaceutical composition do not have special requirements. Various preparations for administration are selected according to the age, gender, other conditions and symptoms of patients. For example, tablets, pills, solutions, suspensions, emulsions, granules or capsules for oral administration; injection preparations can be administered individually, or mixed with an injectable conveying liquid (such as glucose solution and amino acid solution) and intravenously injected; the suppository is administered rectally.

Unless otherwise specified, the following terms when used in the description and the claims of the present invention have the following meanings:

The terms used in the present invention may be preceded and/or followed by a single dash, "—" or a double dash, "═", indicating the bond order of the bond between the named substituent and its parent moiety; wherein the single dash indicates a single bond, a double dash indicates a double bond or a pair of single bonds in the case of a spiro ring substituent. In the absence of a single dash or a double dash, a single bond can be formed between the substituent and its parent moiety; in addition, the substituent is read "from left to right" unless otherwise indicated. For example, $C_{1-6}$ alkoxycarbonyloxy group and —OC(O)($C_{1-6}$ alkyl) have a same meaning; likewise, arylalkyl, arylalkyl-, and -alkylaryl have a same meaning.

The term "alkyl" used in the present invention refers to a branched and linear saturated aliphatic hydrocarbyl group having 1 to 20 carbon atoms, preferably 1 to 12 carbon atoms, more preferably 1 to 6 carbon atoms, e.g., methyl, ethyl, n-propyl, isopropyl, n-butyl, tert-butyl, isobutyl, pentyl, hexyl, heptyl, octyl, nonyl, decyl, 4,4-dimethylpentyl, 2,2,4-trimethylpentyl, undecyl, dodecyl, and various isomers thereof and the like. The "$C_{x1-y1}$" alkyl (x1 and y1 are integers) wherein the number of carbon atoms is specified, e.g., "$C_{1-6}$ alkyl", has a same definition as the term "alkyl" in this paragraph except the range of the number of carbon atoms. When "alkyl" acts as a linker between two groups of other types, it can also be linear or branched, and examples include, but are not limited to —$CH_2$—, —$CH_2CH_2$—, —$CH_2CH_2CHC(CH_3)$—, —$CH_2CH_2(CH_2CH_3)CH_2$—.

The term "cycloalkyl" used in the present invention refers to a monocyclic or bicyclic cycloalkyl ring system. The monocyclic system refers to a cyclic hydrocarbyl group having 3 to 8 carbon atoms, which may be saturated or unsaturated but not aromatic. In certain embodiments, the cycloalkyl group is fully saturated. Examples of monocyclic cycloalkyl include cyclopropyl, cyclobutyl, cyclopentyl, cyclopentenyl, cyclohexyl, cyclohexenyl, cycloheptyl and cyclooctyl. The bicyclic cycloalkyl ring system refers to a bridged monocyclic ring or a fused bicyclic ring. The bridged monocyclic ring contains a monocyclic cycloalkyl ring wherein two non-adjacent carbon atoms of the monocyclic ring are linked by an alkylene bridge having one to three additional carbon atoms (i.e., a bridge of —(CH$_2$)$_w$— wherein w is 1, 2 or 3). Representative examples of bicyclic systems include, but are not limited to, bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane. The fused bicyclic cycloalkyl ring system includes a monocyclic cycloalkyl ring fused to phenyl, monocyclic cycloalkyl, monocyclic cycloalkenyl, monocyclic heterocyclyl or monocyclic heteroaryl. The bridged or fused bicyclic cycloalkyl attaches to the parent moiety of the molecular via any carbon atom contained in the monocyclic cycloalkyl ring. The cycloalkyl group is optionally substituted by one or two groups independently selected from the group consisting of oxo or thioxo. In certain embodiments, the fused bicyclic cycloalkyl is fused to phenyl ring, a 5- or 6-membered monocyclic cycloalkyl, a 5- or 6-membered monocyclic cycloalkenyl, a 5- or 6-membered monocyclic heterocyclyl or a 5- or 6-membered monocyclic cycloalkyl of 5- or 6-membered monocyclic heteroaryl, wherein the fused bicyclic cycloalkyl may be optionally substituted by one or two groups independently selected from the group consisting of oxo or thioxo.

The term "cycloalkenyl" used in the present invention refers to a monocyclic or bicyclic cycloalkenyl ring system. The monocyclic system refers to a cyclic hydrocarbyl group having 3 to 8 carbon atoms, which may be unsaturated (i.e., contain at least one cyclic carbon-carbon double bond) but is not aromatic. Examples of the monocyclic system include cyclopentene and cyclohexene. The bicyclic cycloalkenyl ring refers to a bridged monocyclic ring or a fused bicyclic ring. The bridged monocyclic ring contains a monocyclic cycloalkenyl ring wherein two non-adjacent carbon atoms of the monocyclic ring are linked by an alkylene bridge having one to three additional carbon atoms (i.e., a bridge of —(CH$_2$)$_w$— wherein w is 1, 2 or 3). Representative examples of the bicyclic cycloalkenyl group include, but are not limited to, norbornenyl and bicyclo[2.2.2]octenyl. The fused bicyclic cycloalkenyl ring system includes a monocyclic cycloalkenyl ring which is fused to phenyl, a monocyclic cycloalkyl, a monocyclic cycloalkenyl, a monocyclic heterocyclyl or a monocyclic heteroaryl. The bridged or fused bicyclic cycloalkenyl attaches to the parent moiety of the molecular via any carbon atom contained in the monocyclic cycloalkenyl ring. The cycloalkenyl group may be optionally substituted by one or two groups independently selected from the group consisting of oxo or thioxo.

In the present invention, the term "alkoxy" refers to a cyclic or non-cyclic alkyl having an indicated number of carbon atoms attached via an oxygen bridge. Therefore, "alkoxy" includes the definition of the above alkyl and cycloalkyl.

In the present invention, the term "alkenyl" refers to a linear, branched or cyclic non-aromatic hydrocarbyl having an indicated number of carbon atoms and at least one carbon-carbon double bond. Preferably one carbon-carbon double bond is present, and up to four non-aromatic carbon-carbon double bonds may be present. Thus, "C$_{2-8}$ alkenyl" refers to an alkenyl group having 2 to 8 carbon atoms. "C$_{2-6}$ alkenyl" refers to an alkenyl group having 2 to 6 carbon atoms, including ethenyl, propenyl, butenyl, 2-methylbutenyl and cyclohexenyl. The double bond can be present in the linear chain, branched chain or cyclic portion of the alkenyl, and if it is indicated to be a substituted alkenyl, the alkenyl can be substituted.

In the present invention, the term "alkynyl" refers to a linear, branched, or cyclic hydrocarbyl having an indicated number of carbon atoms and at least one carbon-carbon triple bond. Up to three carbon-carbon triple bonds may be present. Thus, "C$_{2-12}$ alkynyl" refers to an alkynyl group having 2 to 12 carbon atoms. "C$_{2-6}$ alkynyl" refers to an alkynyl group having 2 to 6 carbon atoms, including but not limited to ethynyl, propynyl, butynyl, and 3-methylbutynyl.

In the present invention, the term "aryl" refers to phenyl (i.e., a monocyclic aryl) or an aromatic bicyclic ring system containing at least one benzene ring or a bicyclic ring system containing only carbon atoms. A bicyclic aryl may be azulenyl, naphthyl, or a phenyl group fused to a monocyclic cycloalkyl, a monocyclic cycloalkenyl or a monocyclic heterocyclic ring. The bicyclic aryl is attached to the parent molecule via any carbon atom contained in the phenyl moiety of the bicyclic system or any carbon atom bearing naphthyl or an azulene ring. A fused monocyclic cycloalkyl or monocyclic heterocyclyl moiety of the bicyclic aryl can be optionally substituted by one or two groups independently selected from the group consisting of oxo or thioxo. Representative examples of the bicyclic aryl include, but are not limited to, azulenyl, naphthyl, dihydroindene-1-yl, dihydroindene-2-yl, dihydroindene-3-yl, dihydroindene-4-yl, 2,3-dihydroindole-4-yl, 2,3-dihydroindole-5-yl, 2,3-dihydroindole-6-yl, 2,3-dihydroindole-7-yl, indene-1-yl, indene-2-yl, indene-3-yl, indene-4-yl, dihydronaphthalene-2-yl, dihydronaphthalene-3-yl, dihydronaphthalene-4-yl, dihydronaphthalene-1-yl, 5,6,7,8-tetrahydronaphthalene-1-yl, 5,6,7,8-tetrahydronaphthalene-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-benzofuran-2-one-5-yl, 2H-benzofuran-2-one-6-yl, 2H-benzofuran-2-one-7-yl, 2H-benzofuran-2-one-8-yl, isoindoline-1,3-dione-4-yl, isoindoline-1,3-dione-5-yl, indene-1-one-4-yl, indene-1-one-5-yl, indene-1-one-6-yl, indene-1-one-7-yl, 2,3-dihydrobenzo[b][1,4]dioxan-5-yl, 2,3-dihydrobenzo[b][1,4]dioxan-6-yl, 2H-benzo[b][1,4]oxazin-3(4H)-one-5-yl, 2H-benzo[b][1,4]oxazin-3 (4H)-one-6-yl, 2H-benzo[b][1,4]oxazin-3 (4H)-one-7-yl, 2H-benzo[b][1,4]oxazine-3(4H)-one-8-yl, benzo[d]oxazin-2(3H)-one-5-yl, benzo[d]oxazin-2(3H)-one-6-yl, benzo[d]oxazin-2(3H)-one-7-yl, benzo[d]oxazin-2(3H)-one-8-yl, quinazoline-4(3H)-one-5-yl, quinazoline-4(3H)-one-6-yl, quinazoline-4(3H)-keto-7-yl, quinazoline-4(3H)-one-8-yl, quinoxaline-2(1H)-one-5-yl, quinoxaline-2(1H)-one-6-yl, quinoxaline-2(1H)-one-7-yl, quinoxaline-2(1H)-one-8-yl, benzo[d]thiazol-2(3H)-one-4-yl, benzo[d]thiazol-2(3H)-one-5-yl, benzo[d]thiazol-2(3H)-one-6-yl and benzo[d]thiazol-2(3H)-one-7-yl. In certain embodiments, the bicyclic aryl is a naphthyl ring or a phenyl ring each of which is fused to a 5- or 6-membered monocyclic cycloalkyl, a 5- or 6-membered monocyclic cycloalkenyl or a 5- or 6-membered monocyclic heterocyclyl, wherein the fused cycloalkyl, cycloalkenyl and heterocyclyl may be optionally substituted by one or two groups independently selected from the group consisting of oxo or thioxo.

In the present invention, the term "cyano" as used herein refers to —CN.

In the present invention, the term "halogen" as used herein refers to fluorine, chlorine, bromine or iodine.

In the present invention, the term "heteroaryl" as used herein refers to a monocyclic or bicyclic heteroaryl system containing at least one heteroaryl ring. The monocyclic heteroaryl can be a 5- or 6-membered ring. The 5-membered ring consists of two double bonds and one, two, three or four nitrogen atoms or one oxygen atom or sulfur atom. The 6-membered ring consists of three double bonds and one, two, three or four nitrogen atoms. The 5- or 6-membered heteroaryl is attached to the parent molecule via any carbon or nitrogen atom contained in the heteroaryl. Representative examples of the monocyclic heteroaryl include, but are not limited to, furyl, imidazolyl, isoxazolyl, isothiazolyl, oxadiazolyl, oxazolyl, pyridyl, pyridazinyl, pyrimidinyl, pyrazinyl, pyrazolyl, pyrrolyl, tetrazolyl, thiadiazolyl, thiazolyl, thienyl, triazolyl and triazinyl. The bicyclic heteroaryl consists of a monocyclic heteroaryl which is fused to phenyl, a monocyclic cycloalkyl, a monocyclic cycloalkenyl, a monocyclic heterocyclyl or a monocyclic heteroaryl. The fused cycloalkyl or heterocyclyl moiety of the bicyclic heteroaryl may be optionally substituted by one or two groups independently selected from the group consisting of oxo or thioxo. When the bicyclic heteroaryl contains a fused cycloalkyl, cycloalkenyl or heterocyclyl ring, the bicyclic heteroaryl is attached to the parent molecule via any carbon or nitrogen atoms contained in the monocyclic heteroaryl portion of the bicyclic system. When the bicyclic heteroaryl is a monocyclic heteroaryl which is fused to a benzene ring or a monocyclic heteroaryl, the bicyclic heteroaryl is attached to the parent molecule via any carbon or nitrogen atoms in the bicyclic ring system. Representative examples of the bicyclic heteroaryl include, but are not limited to, benzimidazolyl, benzofuranyl, benzothienyl, benzooxadiazolyl, benzothiazolyl, cinnolinyl, 5,6-dihydroquinolin-2-yl, 5,6-dihydroquinolin-1-yl, furopyridinyl, indazolyl, indolyl, isoquinolinyl, naphthyridinyl, purinyl, quinolinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridyl, 4,5,6,7-tetrahydro[c][1,2,5]oxadiazolyl and 6,7-dihydro[c][1,2,5]oxadiazol-4(5H)-one. In certain embodiments, the fused bicyclic heteroaryl is fused to a 5- or 6-membered monocyclic heteroaryl ring which is fused to phenyl ring, a 5- or 6-membered monocyclic cycloalkyl, a 5- or 6-membered monocyclic cycloalkenyl, a 5- or 6-membered monocyclic heterocyclyl or a 5- or 6-membered monocyclic heteroaryl, wherein the fused cycloalkyl, cycloalkenyl and heterocyclyl may be optionally substituted by one or two groups independently selected from the group consisting of oxo or thioxo.

In the present invention, the term "heterocyclyl" or "heterocyclic ring" as used herein refers to a monocyclic heterocyclic ring or a bicyclic heterocyclic ring. The monocyclic heterocyclic ring is a 3, 4, 5, 6 or 7-membered ring having at least one heteroatom selected from the group consisting of O, N and S, wherein the ring is saturated or unsaturated, but not aromatic. The monocyclic heterocyclic ring is attached to the parent molecule via any carbon or nitrogen atoms contained in the monocyclic heterocyclic ring. Representative examples of the monocyclic heterocyclic ring include, but are not limited to, azetidinyl, azepanyl, aziridine, diazepanyl, 1,3-dioxanyl, 1,3-dioxolanyl, 1,3-dithiolanyl, 1,3-dithianyl, imidazolinyl, imidazolidinyl, isothiazolidinyl, isothiazolyl, isoxazolinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothiophenyl, thiadiazolinyl, thiadiazolidinyl, thiazolinyl, thiazolidinyl, thiomorpholinyl, 1,1-dioxothiomorpholinyl, thiopyranyl and trithianyl. The bicyclic heterocyclic ring is a monocyclic heterocyclic ring which is fused to phenyl, a monocyclic cycloalkyl, a monocyclic cycloalkenyl, a monocyclic heterocyclyl or a monocyclic heteroaryl. The bicyclic heterocyclic ring is attached to the parent molecule via any carbon or nitrogen atoms contained in the monocyclic heterocyclic moiety of the bicyclic system. Representative examples of the bicyclic heterocyclyl include, but are not limited to, 2,3-dihydrobenzofuran-2-yl, 2,3-dihydrobenzofuran-3-yl, indoline-1-yl, indoline-2-yl, indoline-3-yl, 2,3-dihydrobenzothiophen-2-yl, decahydroquinolinyl, decahydroisoquinolinyl, octahydro-1H-indolyl, octahydrobenzofuranyl. The heterocyclyl may be optionally substituted by one or two groups independently selected from the group consisting of oxo or thioxo. In certain embodiments, the bicyclic heterocyclyl is a 5- or 6-membered monocyclic heterocyclic ring which is fused to benzene ring, a 5- or 6-membered monocyclic cycloalkyl, a 5- or 6-membered monocyclic cycloalkenyl, a 5- or 6-membered monocyclic heterocyclyl or a 5- or 6-membered monocyclic heteroaryl, wherein the bicyclic heterocyclyl may be optionally substituted by one or two groups independently selected from the group consisting of oxo or thioxo.

In the present invention, the term "hydroxy" as used herein refers to —OH.

In the present invention, the term "nitro" as used herein refers to —NO$_2$.

In the present invention, the term "oxo" as used herein refers to =O.

In the present invention, the term "thioxo" as used herein refers to =S.

In the present invention, the substituent of "$C_{x1}$-$C_{y1}$" (x1 and y1 are integers) having an indicated number of carbon atoms, e.g, "$C_{x1}$-$C_{y1}$" alkyl, "$C_{x1}$-$C_{y1}$" cycloalkyl group, "$C_{x1}$-$C_{y1}$" cycloalkenyl, "$C_{x1}$-$C_{y1}$" alkoxy, "$C_{x1}$-$C_{y1}$" alkenyl, "$C_{x1}$-$C_{y1}$" alkynyl, "$C_{x1}$-$C_{y1}$" aryl, "$C_{x1}$-$C_{y1}$" heteroaryl or "$C_{x1}$-$C_{y1}$" heterocyclyl refers to the number of carbon atoms which does not contain a substituent, for example, a $C_1$-$C_{10}$ alkyl refers to a $C_1$-$C_{10}$ alkyl which does not contain a substituent.

It is to be understood by the skilled person in the art that any group which is substituted by one or more substituents than one does not include those substituents which is of impractical high steric hindrance, synthetically unfeasible, and/or inherently labile.

In the present invention, the term "pharmaceutically acceptable salt" as used herein refers to a pharmaceutically acceptable salt and solvate formed with an acid or a base. Such pharmaceutically acceptable salts include, but are not limited to, a salt formed with an inorganic acid, e.g., hydrochloride, phosphate, diphosphate, hydrobromide, sulfate, sulfinate, nitrate, and the like; s salt formed with an organic acid, e.g., malate, maleate, fumarate, tartrate, succinate, citrate, acetate, lactate, sulfonate, tosylate, 2-hydroxy ethyl sulfonate, benzoate, salicylate, stearate and alkanoate such as acetate, a salt formed with HOOC—(CH$_2$)$_n$—COOH wherein n is 0 to 4, and the like. Similarly, pharmaceutically acceptable cations include, but are not limited to, sodium, potassium, calcium, aluminum, lithium, and ammonium. The person skilled in the art will recognize a variety of synthetic methods that may be used to prepare a non-toxic pharmaceutically acceptable salt.

In the present invention, the "solvate" e.g., "hydrate" is formed by the interaction of a solvent and a compound. The term "compound" should be understood to include a solvate of a compound (including a hydrate of a compound). Similarly, "salt" also includes a solvate of a salt (e.g., a hydrate of a salt). Suitable solvates are pharmaceutically acceptable, e.g., hydrates, which include monohydrates and hemihydrates.

Without violating the common sense in the art, the above preferred conditions can be arbitrarily combined, then preferred embodiments of the present invention are obtained.

The reagents and raw materials used in the present invention are commercially available.

In the present invention, the room temperature refers to an ambient temperature of 10° C. to 35° C.

The positive and progressive effect of the present invention is that the nitrogenous aromatic heterocyclic compound of the present invention can be a ALK5 inhibitor, and can be used to manufacturing a medicament for treating cancer, renal fibrosis, liver fibrosis, pulmonary fibrosis, viral infection, chronic nephritis, acute nephritis, diabetic nephropathy, osteoporosis, arthritis, wound healing, ulceration, corneal trauma, heart valve stenosis, congestive cardiac necrosis, neurological impairment, Alzheimer's syndrome, peritoneal or subcutaneous adhesions, atherosclerosis and tumor metastasis.

DETAILED DESCRIPTION OF THE PREFERRED EMBODIMENT

The reagents and raw materials (except intermediates) used in the present invention are commercially available. The room temperature used in the present invention refers to an ambient temperature of 10° C. to 35° C. Overnight refers to 8 to 15 hours. Reflux is the reflux temperature of a solvent at normal pressure. All mass spectra were determined by Agilent 6110. All nuclear magnetic data was contained by Bruker Avance-400.

The synthetic route of compound 1 and 2

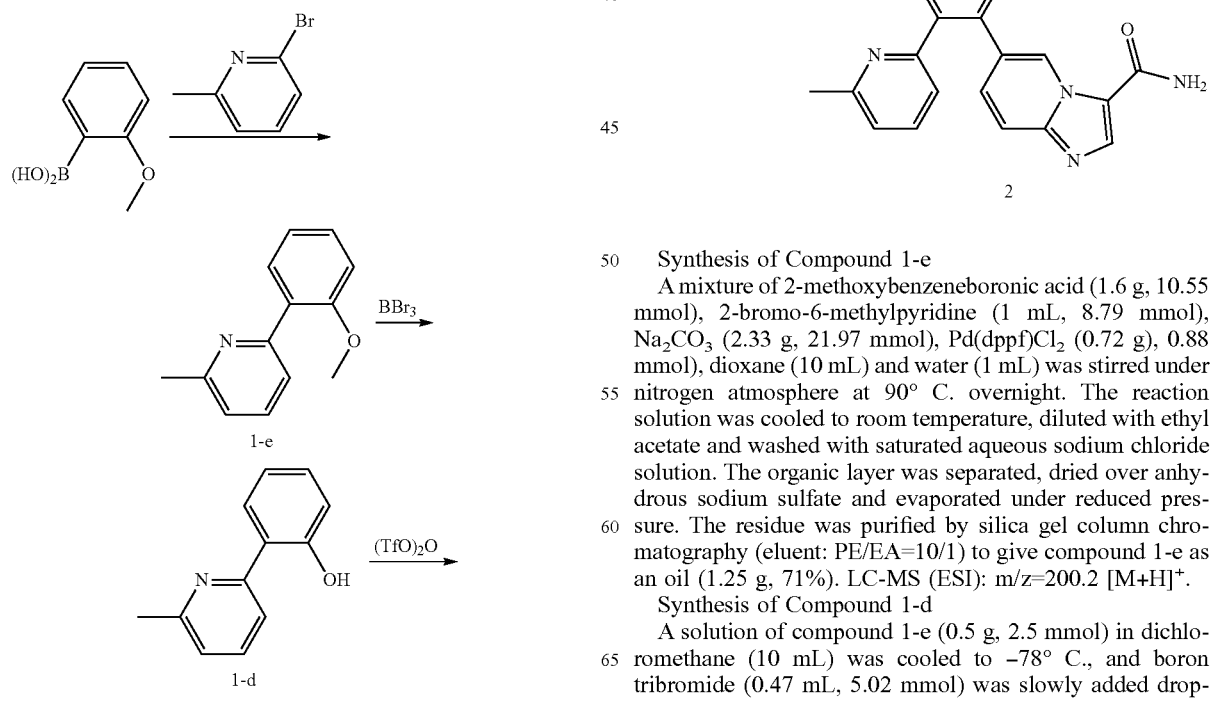

Synthesis of Compound 1-e

A mixture of 2-methoxybenzeneboronic acid (1.6 g, 10.55 mmol), 2-bromo-6-methylpyridine (1 mL, 8.79 mmol), Na$_2$CO$_3$ (2.33 g, 21.97 mmol), Pd(dppf)Cl$_2$ (0.72 g), 0.88 mmol), dioxane (10 mL) and water (1 mL) was stirred under nitrogen atmosphere at 90° C. overnight. The reaction solution was cooled to room temperature, diluted with ethyl acetate and washed with saturated aqueous sodium chloride solution. The organic layer was separated, dried over anhydrous sodium sulfate and evaporated under reduced pressure. The residue was purified by silica gel column chromatography (eluent: PE/EA=10/1) to give compound 1-e as an oil (1.25 g, 71%). LC-MS (ESI): m/z=200.2 [M+H]$^+$.

Synthesis of Compound 1-d

A solution of compound 1-e (0.5 g, 2.5 mmol) in dichloromethane (10 mL) was cooled to −78° C., and boron tribromide (0.47 mL, 5.02 mmol) was slowly added dropwise. The reaction solution was stirred at −78° C. for half an hour, then the reaction solution was allowed to slowly warm to room temperature and stirred for another 1 hour. The reaction solution was slowly added dropwise to ice water (10 mL), then the organic layer was separated and the aqueous layer was extracted with dichloromethane (10 mL×2). The organic layers were combined, dried over anhydrous sodium sulfate and evaporated under reduced pressure to give compound 1-d as an oil (0.4 g, 86%). LC-MS (ESI): m/z=186.1 [M+H]+.

Synthesis of Compound 1-c

Triethylamine (0.45 mL, 3.29 mmol) and compound 1-d (0.4 g, 2.16 mmol) were dissolved in dichloromethane (20 mL). The solution was cooled with ice water, and trifluoromethanesulfonic anhydride (0.44 mL, 2.59 mmol) was slowly added. The reaction solution was stirred at room temperature overnight, then diluted with water (15 mL). The organic layer was separated and the aqueous layer was extracted with dichloromethane (10 mL×2). The organic layers were combined, dried over anhydrous sodium sulfate and evaporated under reduced pressure. The residue was purified by silica gel column chromatography (eluent: PE/EA=10/1) to give compound 1-c as an oil (0.6 g, 87%). LC-MS (ESI): m/z=318.0 [M+H]+.

Synthesis of Compound 1

A mixture of compound 1-c (500 mg, 1.57 mmol), commercially available compound 1-b (442.5 mg, 1.89 mmol), tetrakis(triphenylphosphine)palladium (182.1 mg, 0.16 mmol), sodium carbonate (501.1 mg, 4.73 mmol), toluene (6.0 mL), ethanol (6.0 mL) and water (3.0 mL) was stirred under nitrogen atmosphere at 85° C. overnight. The reaction solution was cooled to room temperature, diluted with ethyl acetate and washed with saturated aqueous sodium chloride solution. The organic layer was separated, dried over anhydrous sodium sulfate and evaporated under reduced pressure to give crude product of compound 1a, which was directly used in the next step without further purification.

The above crude product of compound 1a was dissolved in MeOH (2 mL) and THF (2 mL), followed by addition of aqueous sodium hydroxide solution (2 M). The reaction solution was stirred at room temperature for 2 hours. After completion of the reaction, the reaction solution was evaporated under reduced pressure to remove the organic solvent. The residue was diluted with water (10 mL) and dichloromethane (10 mL). The aqueous layer was cooled to 0° C., neutralized to pH of 5-6 with hydrochloric acid (6 M), and extracted with chloroform/isopropyl alcohol (3/1). The organic layer was washed with saturated brine, dried over anhydrous sodium sulfate and evaporated under reduced pressure. The residue was purified by preparative HPLC to give compound 1 as a white solid (250 mg, yield 48% for two steps). LC-MS (ESI): m/z=330.1 [M+H]+. 1H NMR (400 MHz, CDCl3): δ9.32 (s, 1H), 8.19 (s, 1H), 7.44-7.62 (m, 6H), 7.15-7.17 (d, J=7.2 Hz, 1H), 7.07 (d, J=7.2 Hz, 1H). 6.87 (d, J=8.8 Hz, 1H), 2.47 (s, 3H).

Synthesis of Compound 2

Compound 1 (150 mg, 0.46 mmol) was dissolved in dichloromethane (10 mL), followed by slow addition of oxalyl chloride (1 mL) and a drop of DMF under an ice bath. The reaction solution was warmed to room temperature and stirred for 60 minutes. Then the reaction solution was evaporated under reduced pressure and diluted with dichloromethane (5 mL). The resulting solution was slowly added dropwise to aqueous ammonia (5 mL) under an ice bath, and the reaction solution was stirred at 0° C. for 10 minutes, then warmed to room temperature and stirred overnight. The organic phase was separated and the aqueous phase was extracted with dichloromethane. The organic phase was combined, washed with saturated brine, dried over anhydrous sodium sulfate and evaporated under reduced pressure. The residue was purified by preparative HPLC to give compound 2 (75 mg, 50%). LC-MS (ESI): m/z=329.0 [M+H]+. 1H NMR (400 MHz, CDCl3): δ9.58 (s, 1H), 8.27 (s, 1H), 7.69 (d, J=7.2 Hz, 1H), 7.47-7.55 (m, 4H), 7.38 (t, J=7.6 Hz, 1H), 7.07 (dd, J1=9.2 Hz, J2=1.2 Hz, 1H), 7.01 (d, J=7.6 Hz, 1H), 6.89 (d, J=7.6 Hz, 1H), 5.88 (bs, 2H), 2.52 (s, 3H).

Synthetic Route of Compound 3

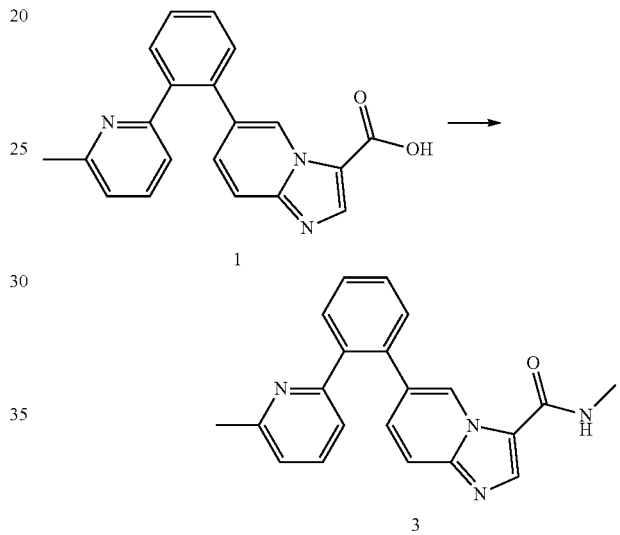

Synthesis of Compound 3

Compound 1 (100 mg, 0.30 mmol) was dissolved in dichloromethane (10 mL), followed by slow addition of oxalyl chloride (1 mL) and a drop of DMF under an ice bath. The reaction solution was warmed to room temperature and stirred for 60 minutes. Then the reaction solution was evaporated under reduced pressure and diluted with dichloromethane (5 mL). The resulting solution was slowly added dropwise to a solution of methylamine in tetrahydrofuran (2 M, 5 mL) under an ice bath, and the reaction solution was stirred at 0° C. for 10 minutes, then warmed to room temperature and stirred overnight. The organic phase was separated and the aqueous phase was extracted with dichloromethane. The organic phase was combined, washed with saturated brine, dried over anhydrous sodium sulfate and evaporated under reduced pressure. The residue was purified by preparative HPLC to give compound 3 (29 mg, 28%). LC-MS (ESI): m/z=343.0 [M+H]+. 1H NMR (400 MHz, CDCl3): δ9.59 (s, 1H), 7.97 (s, 1H), 7.69 (d, J=6.8 Hz, 1H), 7.45-7.53 (m, 3H), 7.32-7.39 (m, 2H), 7.00 (d, J=7.2 Hz, 1H), 6.91 (d, J=9.2 Hz, 1H), 6.86 (d, J=8 Hz, 1H), 6.00 (bs, 1H), 3.04 (d, J=4.8 Hz, 3H), 2.54 (s, 3H).

Synthetic Route of Compound 4

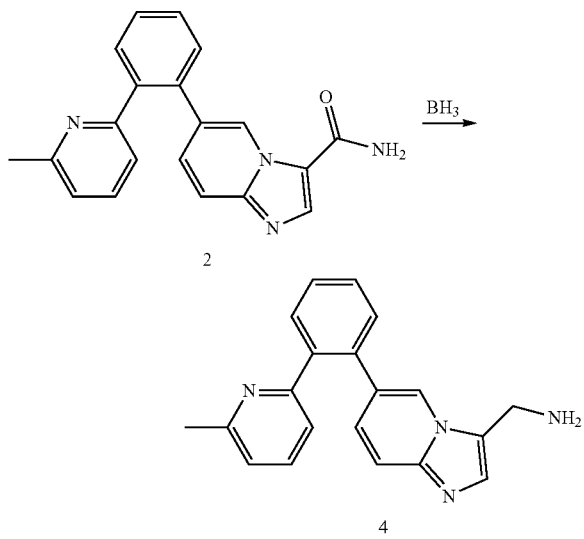

Synthesis of Compound 4

Compound 2 (30 mg, 0.09 mmol) was dissolved in a solution of borane in tetrahydrofuran (1 M, 10 mL). The reaction solution was heated to reflux and stirred for 6 hours. Then the reaction solution was cooled to room temperature, evaporated under reduced pressure, diluted with aqueous hydrochloric acid (6 M, 3 mL) and stirred at reflux for 15 minutes. The reaction solution was cooled to room temperature and filtered. The filtrate was neutralized with an aqueous NaOH solution (6 M, 3 mL) under an ice bath and then extracted with dichloromethane. The organic phase was combined, washed with saturated brine, dried over anhydrous sodium sulfate and evaporated under reduced pressure. The residue was purified by preparative HPLC to give compound 4 (20 mg, 70%). LC-MS (ESI): m/z=315.1 [M+H]$^+$. $^1$H NMR (400 MHz, CDCl$_3$): δ8.06 (s, 1H), 7.67-7.69 (m, 1H), 7.42-7.53 (m, 5H), 7.36 (t, J=7.6 Hz, 1H), 7.00 (d, J=7.2 Hz, 1H), 6.96 (d, J=9.2 Hz, 1H), 6.85 (d, J=8 Hz, 1H), 4.07 (s, 2H), 2.54 (s, 3H).

Synthetic Route of Compound 5

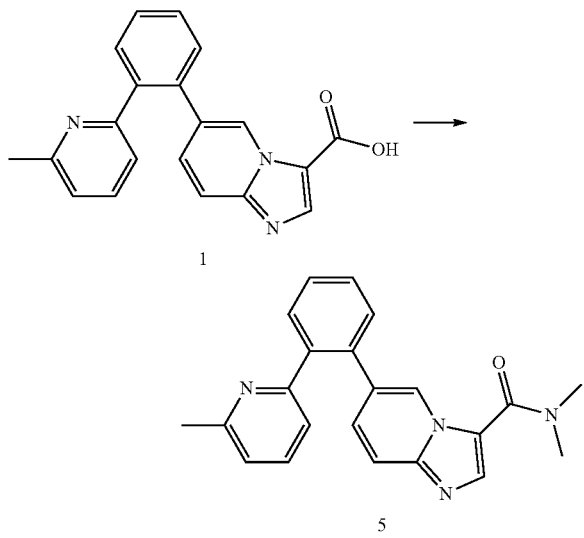

Synthesis of Compound 5

Compound 1 (100 mg, 0.30 mmol) was dissolved in dichloromethane (10 mL), followed by slow addition of oxalyl chloride (1 mL) and a drop of DMF under an ice bath. The reaction solution was warmed to room temperature and stirred for 60 minutes. Then the reaction solution was evaporated under reduced pressure and diluted with dichloromethane (5 mL). The resulting solution was slowly added dropwise to an aqueous solution of methylamine (40%, 5 mL) under an ice bath. The reaction solution was stirred at 0° C. for 10 minutes, then warmed to room temperature and stirred overnight. The organic phase was separated and the aqueous phase was extracted with dichloromethane. The organic phase was combined, washed with saturated brine, dried over anhydrous sodium sulfate and evaporated under reduced pressure. The residue was purified by preparative HPLC to give compound 5 (60 mg, 55%). LC-MS (ESI): m/z=357.0 [M+H]$^+$. $^1$H NMR (400 MHz, CD$_3$OD): δ8.97 (s, 1H), 8.02 (s, 1H), 7.53-7.62 (m, 5H), 7.43 (d, J=9.2 Hz, 1H), 7.15 (d, J=5.6 Hz, 1H), 7.08 (dd, J$_1$=9.2 Hz, J$_2$=1.6 Hz, 1H), 7.04 (d, J=7.6 Hz, 1H), 3.26 (s, 6H), 2.47 (s, 3H).

Synthesis of Compound 6

Compound 6 (40 mg) was obtained as a white solid by replacing the raw material 2-methoxyphenylboronic acid with 6-fluoro-2-methoxyphenylboronic acid according to the synthetic route and method for preparing compound 2. LC-MS (ESI): m/z=347.1 [M+H]$^+$. $^1$H NMR (400 MHz, CD$_3$OD): δ9.40 (s, 1H), 8.24 (s, 1H), 7.61-7.67 (m, 2H), 7.44-7.49 (m, 2H), 7.35-7.35 (m, 1H), 7.14-7.25 (m, 3H), 2.46 (s, 3H).

Synthesis of Compound 7

Compound 7 (30 mg) was obtained as a white solid by replacing the raw material 2-bromo-6-methylpyridine with 2-bromopyridine according to the synthetic route and method for preparing compound 2. LC-MS (ESI): m/z=315.1 [M+H]$^+$. $^1$H NMR (400 MHz, DMSO-d$_6$): δ9.40 (s, 1H), 8.50 (m, 1H), 8.32 (s, 1H), 7.95 (bs, 1H), 7.50-7.67 (m, 6H), 7.36 (bs, 1H), 7.22-7.25 (m, 2H), 6.97 (d, J=9.2 Hz, 1H).

Synthesis of Compound 8

Compound 8 (64 mg) was obtained as a white solid by replacing the raw material 2-methoxyphenylboronic acid with 3-fluoro-2-methoxyphenylboronic acid according to the synthetic route and method for preparing compound 2. LC-MS (ESI): m/z=347.0 [M+H]$^+$. $^1$H NMR (400 MHz, CD$_3$OD): δ9.37 (s, 1H), 8.26 (s, 1H), 7.54-7.62 (m, 3H), 7.47 (d, J=7.2 Hz, 1H), 7.37 (t, J=9.6 Hz, 1H), 7.30 (d, J=9.2 Hz, 1H), 7.12 (d, J=8 Hz, 1H), 7.07 (d, J=7.6 Hz, 1H), 2.42 (s, 3H).

Synthesis of Compound 9

Compound 9 (90 mg) was obtained as a white solid by replacing the raw material 2-methoxyphenylboronic acid with 4-fluoro-2-methoxyphenylboronic acid according to the synthetic route and method for preparing compound 2. LC-MS (ESI): m/z=347.0 [M+H]$^+$. $^1$H NMR (400 MHz, CD$_3$OD): δ9.45 (s, 1H), 8.27 (s, 1H), 7.66 (dd, J$_1$=8.4 Hz, J$_2$=5.6 Hz, 1H), 7.57 (t, J=8 Hz, 1H), 7.51 (d, J=10 Hz, 1H), 7.40 (dd, J$_1$=9.6 Hz, J$_2$=2.8 Hz, 1H), 7.32-7.37 (m, 1H), 7.15-7.21 (m, 2H), 7.05 (d, J=7.6 Hz, 1H), 2.46 (s, 3H).

Synthesis of Compound 10

Compound 10 (100 mg) was obtained as a white solid by replacing the raw material 2-methoxyphenylboronic acid with 5-fluoro-2-methoxyphenylboronic acid according to the synthetic route and method for preparing compound 2. LC-MS (ESI): m/z=347.0 [M+H]$^+$. $^1$H NMR (400 MHz, CD$_3$OD): δ9.43 (s, 1H), 8.26 (s, 1H), 7.63 (dd, J$_1$=8.4 Hz, $J_2$=5.2 Hz, 1H), 7.49 (d, J=9.2 Hz, 1H), 7.33-7.42 (m, 2H), 7.14-7.19 (m, 2H), 7.05 (d, J=7.6 Hz, 1H), 2.48 (s, 3H).

Synthetic Route of Compound 11

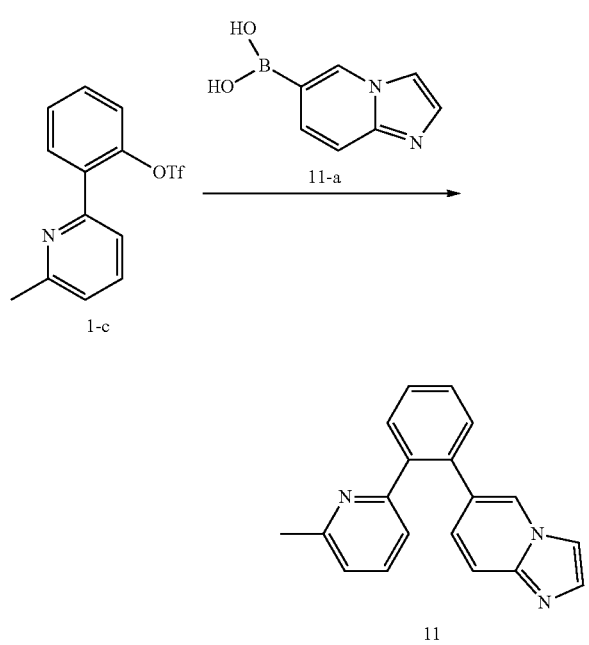

Synthesis of Compound 11

A mixture of compound 1-c (150 mg, 0.47 mmol), commercially available compound 11-a (153.1 mg, 0.57 mmol), tetrakis(triphenylphosphine)palladium (54.6 mg, 0.047 mmol), sodium carbonate (150 mg, 1.42 mmol), toluene (6.0 mL), ethanol (6.0 mL) and water (3.0 mL) was stirred under nitrogen atmosphere at 85° C. overnight. The reaction solution was cooled to room temperature, diluted with ethyl acetate and washed with saturated aqueous sodium chloride solution. The organic layer was separated, dried over anhydrous sodium sulfate and evaporated under reduced pressure. The residue was purified by preparative HPLC to give compound 11 (55 mg, 41%). LC-MS (ESI): m/z=286.1 [M+H]$^+$. $^1$H NMR (400 MHz, CD$_3$OD): δ8.38 (s, 1H), 7.82 (s, 1H), 7.56-7.62 (m, 6H), 7.33 (d, J=9.6, 1H), 7.17 (d, J=7.6, 1H), 7.06 (d, J=7.6, 1H), 6.91 (d, J=9.6, 1H), 2.47 (s, 3H).

Synthetic Route of Compound 12

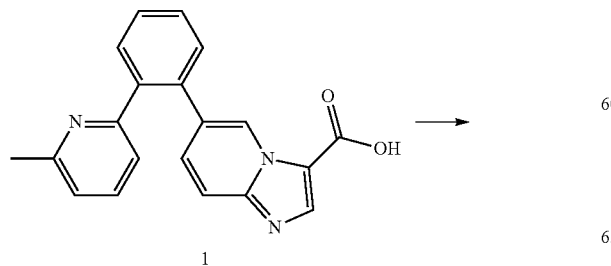

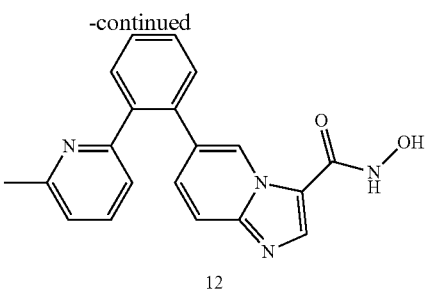

Synthesis of Compound 12

Compound 1 (50 mg, 0.15 mmol) was dissolved in dichloromethane (10 mL), followed by slow addition of oxalyl chloride (1 mL) and a drop of DMF under an ice bath. The reaction solution was warmed to room temperature and stirred for 60 minutes. Then the reaction solution was evaporated under reduced pressure and diluted with dichloromethane (5 mL). The resulting solution was slowly added dropwise to a solution of hydroxylamine hydrochloride (52.7 mg, 0.75 mmol) and triethylamine (0.1 mL, 0.75 mmol) in dichloromethane (5 mL) under an ice bath. The reaction solution was stirred at 0° C. for 10 minutes, then warmed to room temperature and stirred overnight. The organic phase was separated and the aqueous phase was extracted with dichloromethane. The organic phase was combined, washed with water and brine respectively, dried over anhydrous sodium sulfate and evaporated under reduced pressure. The residue was purified by HPLC to give compound 12 (7 mg, 13%). LC-MS (ESI): m/z=345.1 [M+H]$^+$. H NMR (400 MHz, CD$_3$OD): δ9.36 (s, 1H), 8.10 (s, 1H), 7.55-7.64 (m, 5H), 7.47 (d, J=9.2 Hz, 1H), 7.14-7.16 (m, 2H), 7.07 (d, J=8 Hz, 1H), 2.45 (s, 3H).

Synthetic Route of Compound 13

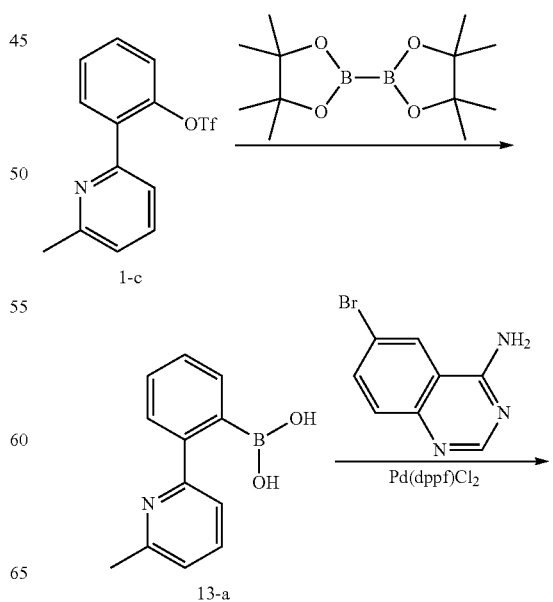

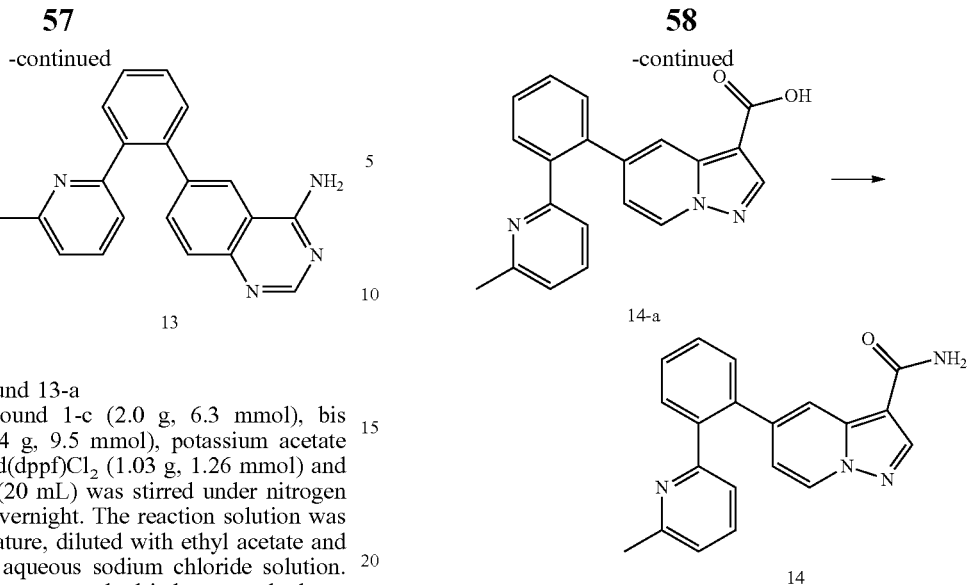

Synthesis of Compound 13-a

A mixture of compound 1-c (2.0 g, 6.3 mmol), bis(pinacolato)diboron (2.4 g, 9.5 mmol), potassium acetate (1.55 g, 15.8 mmol), Pd(dppf)Cl$_2$ (1.03 g, 1.26 mmol) and anhydrous acetonitrile (20 mL) was stirred under nitrogen atmosphere at 80° C. overnight. The reaction solution was cooled to room temperature, diluted with ethyl acetate and washed with saturated aqueous sodium chloride solution. The organic phase was separated, dried over anhydrous sodium sulfate and evaporated under reduced pressure. The residue was purified by silica gel column chromatography (eluent: dichloromethane/methanol=10/1) to give compound 13-a as a gray solid (0.6 g, 45%). LC-MS (ESI): m/z=214.1 [M+H]$^+$.

Synthesis of Compound 13

A mixture of compound 13-a (114.1 mg, 0.54 mmol), 6-bromoquinazoline-4-amine (100 mg, 0.45 mmol), K$_3$PO$_4$ (284.2 mg, 1.34 mmol), Pd(dppf)Cl$_2$ (36.4 mg, 0.045 Methanol), dioxane (10 mL) and water (2 mL) was stirred under nitrogen atmosphere at 95° C. for 2 hours. The reaction solution was cooled to room temperature, diluted with ethyl acetate and washed with saturated aqueous sodium chloride solution. The organic phase was separated, dried over anhydrous sodium sulfate and evaporated under reduced pressure. The residue was purified by preparative HPLC to give compound 13 (55 mg, 40%). LC-MS (ESI): m/z=313.1 [M+H]$^+$. $^1$H NMR (400 MHz, CD$_3$OD): δ8.35 (s, 1H), 8.10 (d, J=2 Hz, 1H), 7.55-7.64 (m, 4H), 7.46-7.52 (m, 2H), 7.35-7.39 (m, 1H), 7.13 (d, J=7.6 Hz, 1H), 6.93 (d, J=8 Hz, 1H), 2.44 (s, 3H).

Synthetic Route of Compound 14

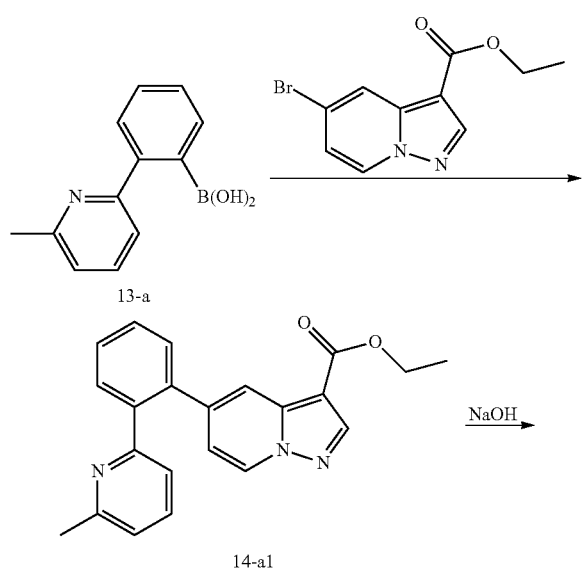

Synthesis of Compound 14-a

A mixture of compound 13-a (47.5 mg, 0.22 mmol), ethyl 5-bromopyrazolo[1,5-A]pyridine-3-carboxylate (50 mg, 0.19 mmol), Na$_2$CO$_3$ (49.2 mg, 0.46 mmol), Pd(dppf)Cl$_2$ (15.2 mg, 0.019 mmol), dioxane (10 mL) and water (1 mL) was stirred under nitrogen atmosphere at 90° C. overnight. The reaction solution was cooled to room temperature and evaporated under reduced pressure. The residue compound 14-a1 was dissolved in methanol (2.0 mL) and THF (2 mL), followed by addition of aqueous sodium hydroxide solution (2 M, 2 mL). The reaction solution was stirred at room temperature for 2 hours. After completion of the reaction, the reaction solution was evaporated under reduced pressure to remove the organic solvent, diluted with water (10 mL) and dichloromethane (10 mL) and the organic layer was discarded. The aqueous layer was cooled to 0° C., neutralized to pH of 5-6 with hydrochloric acid (6 M), extracted with chloroform/isopropanol (3/1). The organic phase was washed with saturated brine, dried over anhydrous sodium sulfate and evaporated under reduced pressure to give compound 14-a as a pale yellow solid (40 mg, yield 65% for two steps). LC-MS (ESI): m/z=330.0 [M+H]$^+$.

Synthesis of Compound 14

Compound 14 (20 mg, 50%) was obtained by using compound 14-a as raw material according to the method for preparing compound 2. LC-MS (ESI): m/z=329.0 [M+H]$^+$. $^1$H NMR (400 MHz, CD$_3$OD): δ8.42 (s, 1H), 8.40 (d, J=7.6 Hz, 1H), 8.18 (s, 1H), 7.54-7.65 (m, 5H), 7.17 (d, J=7.6 Hz, 1H), 7.05 (d, J=8 Hz, 1H), 6.64 (dd, J$_1$=7.2 Hz, J$_2$=1.6 Hz, 1H), 2.48 (s, 3H).

Synthetic Route of Compound 15

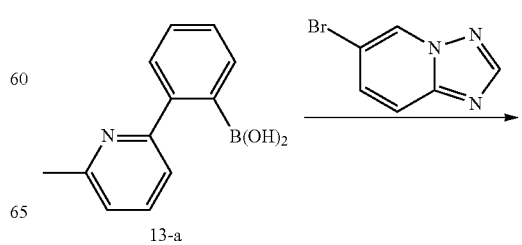

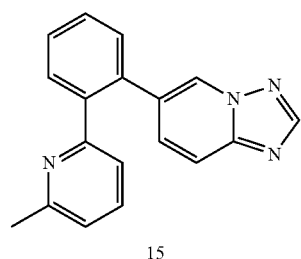

15

Synthesis of Compound 15

A mixture of the compound 6-bromo-1,2,4-triazolo[1,5-a]pyridine (0.2 g, 1.0 mmol), compound 13-a (0.32 g, 1.5 mmol), Pd(dppf)Cl$_2$ (0.21 g, 0.26 mmol), sodium carbonate (0.22 g, 2.0 mmol), dioxane (6 mL) and water (2 mL) was stirred under nitrogen atmosphere at 88° C. overnight. The reaction solution was cooled to room temperature and evaporated under reduced pressure. The residue was purified by silica gel column chromatography (eluent: PE/EA=1/1) to give compound 15 (90 mg, 31.5%). LC-MS (ESI): m/z=287.1 [M+H]$^+$. $^1$H NMR (400 MHz, CDCl$_3$): δ8.66 (s, 1H), 8.39 (s, 1H), 7.64 (m, 6H), 7.36 (d, J=8.0 Hz, 1H), 7.17 (d, J=8.0 Hz, 1H), 7.11 (d, J=8.0 Hz, 1H), 2.43 (s, 3H).

Synthetic Route of Compound 16

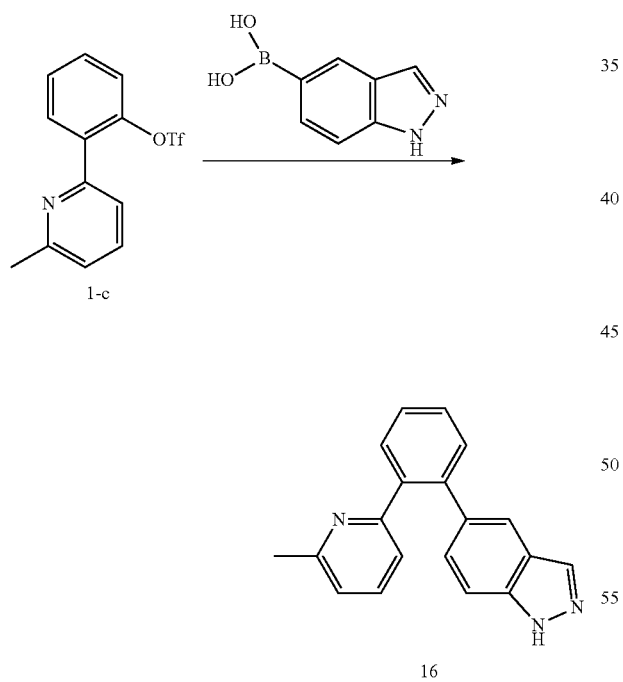

Compound 16 (160 mg, 56.1%) was obtained by using indazole-5-boronic acid as raw material according to the method for preparing compound 11. LC-MS (ESI): m/z=286 [M+H]$^+$. $^1$H NMR (400 MHz, CD$_3$OD): δ8.00 (s, 1H), 7.56 (m, 5H), 7.41 (t, J=8.0 Hz, 1H), 7.33 (s, 1H), 7.11 (d, J=8.0 Hz, 1H), 6.92 (d, J=8.0 Hz, 1H), 6.82 (d, J=8.0 Hz, 1H), 2.50 (s, 3H).

Synthetic Route of Compound 17 and 18

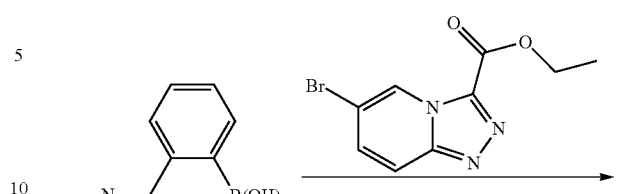

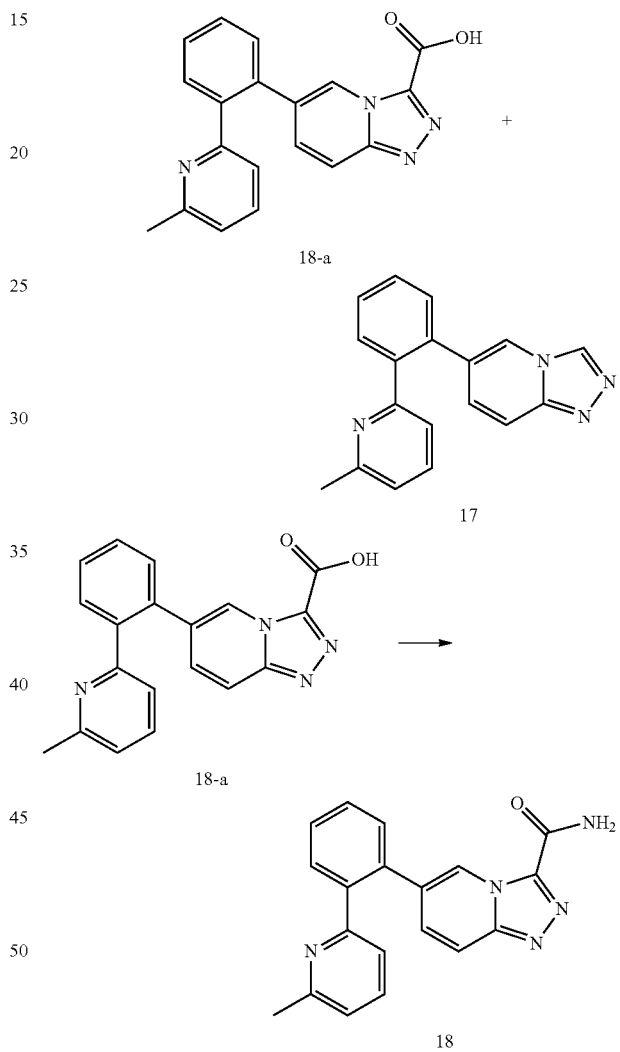

Synthesis of Compound 17 and 18-a

A mixture of compound 13-a (0.53 g, 2.5 mmol), compound 18-b (0.54 g, 2.0 mmol), Pd(dppf)Cl$_2$ (0.43 g, 0.53 mmol), Na$_2$CO$_3$ (0.43 g, 4.12 mmol), dioxane (60 mL) and water (20 mL) was stirred under nitrogen atmosphere at 80° C. overnight. The reaction solution was cooled to room temperature and evaporated under reduced pressure. The residue was dissolved in methanol (2.0 mL) and THF (2 mL), followed by addition of aqueous sodium hydroxide solution (2 M, 2 mL). The reaction solution was stirred at room temperature for 2 hours. After completion of the reaction, the reaction solution was evaporated under reduced pressure to remove the organic solvent, diluted with water (10 mL) and dichloromethane (10 mL) and the organic layer was discarded. The aqueous layer was cooled to 0° C., neutralized to pH of 5-6 with hydrochloric acid (6 M), extracted with chloroform/isopropanol (3/1). The organic phase was washed with saturated brine, dried over anhydrous sodium sulfate and evaporated under reduced pressure. The residue was purified by preparative HPLC to give compound 17 (21 mg) and 18-a (25 mg).

Compound 17: LC-MS (ESI): m/z=287.1 [M+H]+. 1H NMR (400 MHz, CD3OD): δ9.16 (s, 1H), 8.45 (s, 1H), 7.65 (m, 5H), 7.51 (d, J=8.0 Hz, 1H), 7.18 (d, J=8.0 Hz, 1H), 7.15 (d, J=8.0 Hz, 1H), 7.01 (d, J=8.0 Hz, 1H), 2.43 (s, 3H).

Compound 18-a: LC-MS (ESI): m/z=331.1 [M+H]+.

Synthesis of Compound 18

Compound 18 (10 mg, 46%) was obtained by using compound 18-a as raw material according to the method for preparing compound 2. LC-MS (ESI): m/z=330.0 [M+H]+. 1H NMR (400 MHz, CDCl3): δ9.20 (s, 1H), 7.67 (m, 6H), 7.25 (d, J=8.0 Hz, 1H), 7.16 (d, J=8.0 Hz, 1H), 7.12 (d, J=8.0 Hz, 1H), 2.41 (s, 3H).

Synthetic Route of Compound 19

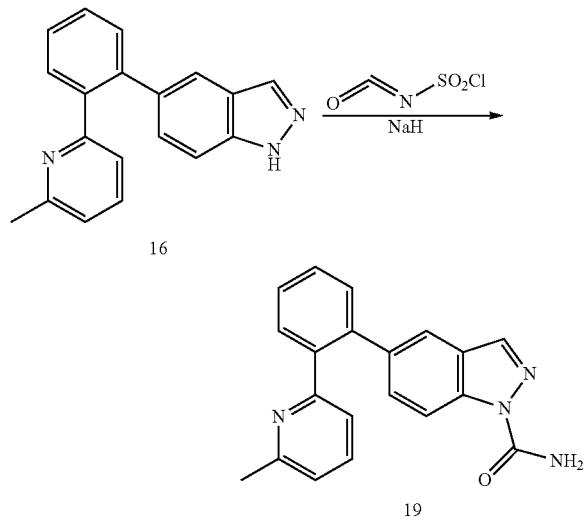

Synthesis of Compound 19

A mixture of compound 16 (0.143 g, 0.5 mmol), sodium hydride (0.043 g, 1.0 mmol) and tetrahydrofuran (10 mL) was stirred under an ice bath for 10 min. Then the reaction solution was warmed to room temperature and stirred for another 2 hours, followed by addition of chlorosulphonyl isocyanate (0.141 g, 1.0 mmol). The reaction solution was stirred at room temperature overnight and then the reaction was quenched with water (50 mL). The resulting mixture was extracted with ethyl acetate (30 mL×3). The organic phase was combined and evaporated. The residue was purified by preparative HPLC to give compound 19 as a white solid (23 mg, 14%). LC-MS (ESI): m/z=329 [M+H]+. 1H NMR (400 MHz, CD3OD): δ8.23 (s, 1H), 8.15 (s, 1H), 7.60 (m, 5H), 7.43 (t, J=8.0 Hz, 1H), 7.10 (d, J=8.0 Hz, 1H), 7.02 (d, J=8.0 Hz, 1H), 6.83 (d, J=8.0 Hz, 1H), 2.50 (s, 3H).

Synthetic Route of Compound 20 and 21

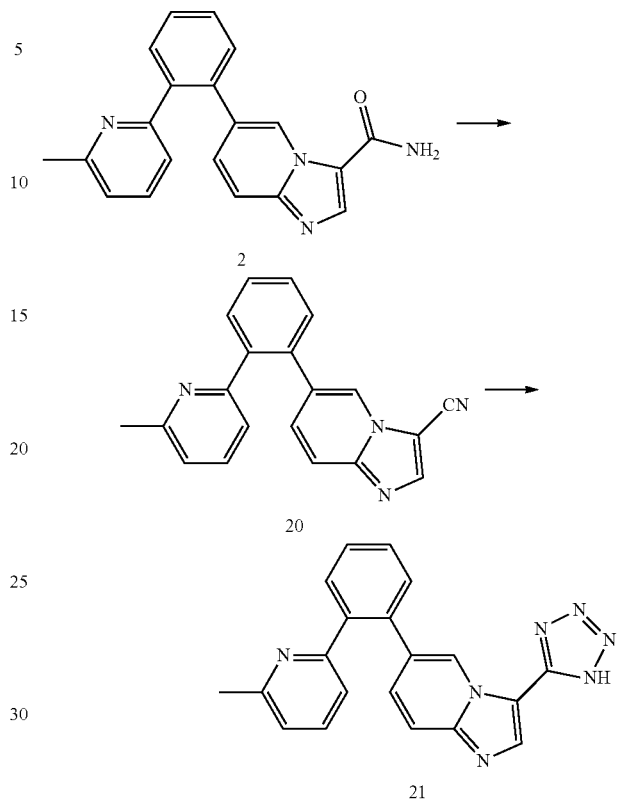

Synthesis of Compound 20

A solution of compound 2 (250 mg, 0.76 mmol) and pyridine (0.12 mL, 1.52 mmol) in tetrahydrofuran (10 mL) was cooled to 0° C., and trifluoroacetic anhydride (0.16 mL, 1.14 mmol) was slowly added dropwise. After completion of the addition, the reaction solution was allowed to warm to room temperature and stirred for 2 hours. After completion of the reaction, the reaction solution was evaporated to remove tetrahydrofuran, followed by addition of saturated sodium bicarbonate solution. The resulting mixture was stirred for 10 minutes and extracted with dichloromethane (10 mL×3). The organic phase was combined, washed with water and saturated brine, dried over anhydrous sodium sulfate, filtered and evaporated under reduced pressure. The residue was purified by silica gel column chromatography (eluent: PE/EA=3/1) to give compound 20 (150 mg, 64%). LC-MS (ESI): m/z=311.0 [M+H]+. 1H NMR (400 MHz, CD3OD): δ8.32 (s, 1H), 8.26 (s, 1H), 7.59-7.67 (m, 6H), 7.31 (dd, J1=9.6 Hz, J2=2 Hz, 1H), 7.20 (d, J=8 Hz, 1H), 7.12 (d, J=8 Hz, 1H), 2.46 (s, 3H).

Synthesis of Compound 21

Compound 20 (50 mg, 0.16 mmol), NaN3 (13.6 mg, 0.21 mmol), and ammonium chloride (11.2 mg, 0.21 mmol) were dissolved in DMF (2 mL). The reaction solution was heated to 80° C. and stirred overnight. After completion of the reaction, the reaction solution was cooled to room temperature. Water (5 mL) was slowly added under stirring and a white solid precipitated. The mixture was stirred for half an hour and then filtered. The solid was washed with water and dried in the air to give compound 21 (45 mg, 79%). LC-MS (ESI): m/z=354.0 [M+H]+. 1H NMR (400 MHz, DMSO-d6): δ 9.32 (s, 1H), 8.33 (s, 1H), 7.59-7.70 (m, 5H), 7.49 (t, J=7.6 Hz, 1H), 7.14 (dd, J1=9.2 Hz, J2=1.6 Hz, 1H), 7.06 (d, J=7.6 Hz, 1H), 7.01 (d, J=8 Hz, 1H), 2.38 (s, 3H).

63

Synthetic Route of Compound 22

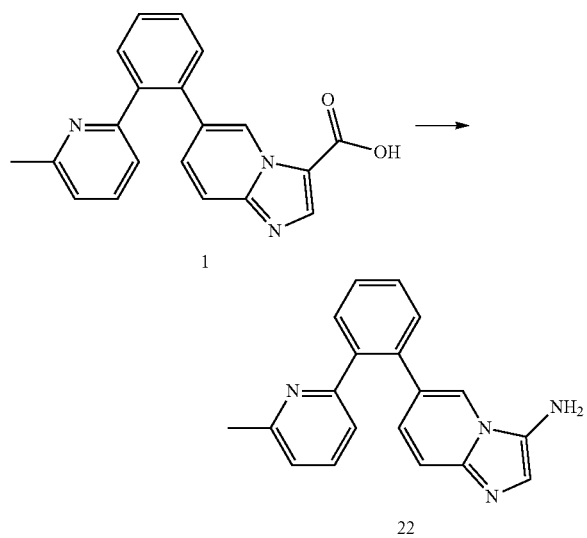

Synthesis of Compound 22

Compound 1 (400 mg, 1.2 mmol) was dissolved in dichloromethane (10 mL), followed by slow addition of oxalyl chloride (1 mL) and a drop of DMF under an ice bath. The reaction solution was warmed to room temperature and stirred for 60 minutes. Then the reaction solution was evaporated under reduced pressure and diluted with acetone (10 mL). Sodium azide (118.4 mg, 1.8 mmol) and water (10 mL) were successively added. The reaction solution was warmed to 90° C. and stirred overnight. The reaction solution was cooled to room temperature, evaporated under reduced pressure to remove the organic solvent and the aqueous layer was extracted with dichloromethane. The organic phase was combined, washed with water and brine respectively, dried over anhydrous sodium sulfate and evaporated under reduced pressure. The residue was purified by preparative thin layer chromatography (eluent: dichloromethane/methanol=10/1) to give compound 22 (150 mg, 41%). LC-MS (ESI): m/z=301.0 [M+H]$^+$. $^1$H NMR (400 MHz, CD$_3$OD): δ8.08 (s, 1H), 7.54-7.62 (m, 5H), 7.18 (s, 1H), 7.16 (d, J=2.4 Hz, 1H), 7.06 (d, J=7.6 Hz, 1H), 6.99 (s, 1H), 6.72 (dd, J$_1$=9.6 Hz, J$_2$=1.6 Hz, 1H), 2.49 (s, 3H).

Synthetic Route of Compound 23

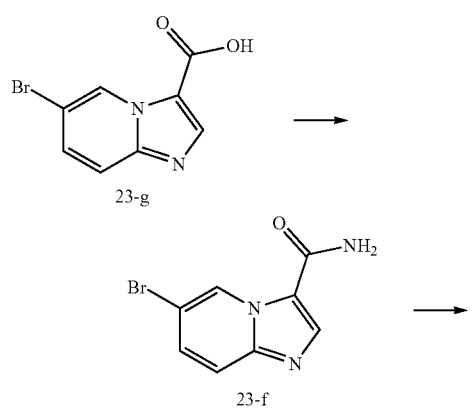

64

-continued

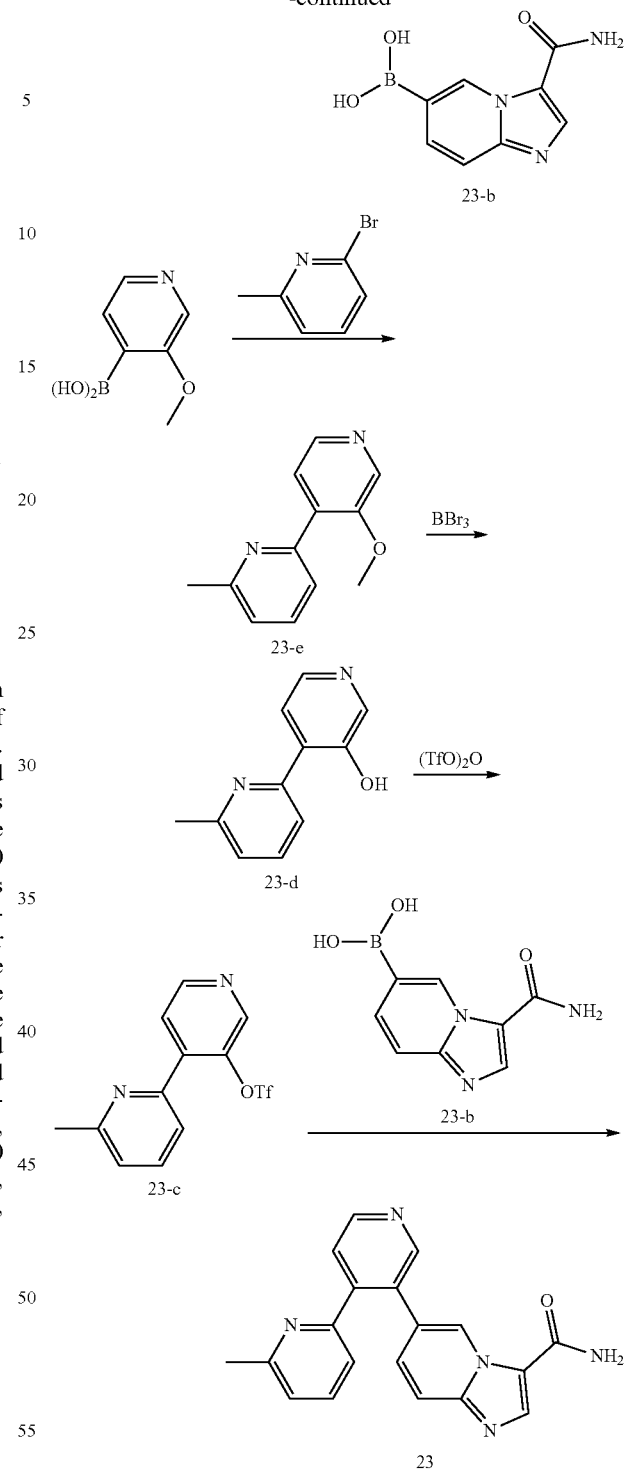

Synthesis of Compound 23-f

A mixture of commercially available compound 23-g (8.6 g, 35.8 mmol) and dichloromethane (60 mL) was cooled under an ice bath, oxalyl chloride (8 mL) was added under stirring, followed by slow addition of DMF (0.3 mL). The reaction solution was allowed to warm to room temperature and stirred for 4 hours. The reaction solution was evaporated under reduced pressure and diluted with dichloromethane (40 mL). The resulting solution was slowly added dropwise to aqueous ammonia (50 mL), and the mixture was stirred at 0° C. for 10 minutes, then warmed to room temperature and stirred for another 2 hours. The reaction solution was evaporated to remove dichloromethane, diluted with water (60 mL), stirred for 1 hour and then filtered. The solid was washed with water and dried to give compound 23-f as a white solid (7.6 g, 88.8%). LC-MS (ESI): m/z=240.1 [M+H]$^+$.

Synthesis of Compound 23-b

A mixture of compound 23-f (7.2 g, 30.1 mmol), bis (pinacolato)diboron (22.86 g, 90 mmol), potassium acetate (8.82 g, 90 mmol), Pd(dppf)Cl$_2$ (0.43 g, 0.53 mmol) and anhydrous dioxane (80 mL) was heated to 100° C. under nitrogen atmosphere and stirred for 3 hours. The reaction solution was cooled to room temperature, evaporated and diluted with water (200 mL). The mixture was stirred, filtered and the solid was dried. The solid was dissolved in ethyl acetate (200 mL), followed by addition of a saturated solution of hydrogen chloride in ethyl acetate (20 mL) under stirring. The mixture was filtered and the solid was dried to give compound 23-b (5.96 g, 96.5%). LC-MS (ESI): m/z=206 [M+H]$^+$. $^1$H NMR (400 MHz, CD$_3$OD): δ9.96 (s, 1H), 8.54 (s, 1H), 8.13 (d, J=8.0 Hz, 1H), 7.89 (d, J=8.0 Hz, 1H).

Synthesis of Compound 23-e

Compound 23-e (400 mg, 75%) was obtained by using 3-methoxy-4-pyridineboronic acid as raw material according to the method for preparing compound 1-e. LC-MS (ESI): m/z=201.1 [M+H]$^+$.

Synthesis of Compound 23-d

Compound 23-d (250 mg, 67%) was obtained by using compound 23-e as raw material according to the method for preparing compound 1-d. LC-MS (ESI): m/z=187.0 [M+H]$^+$.

Synthesis of Compound 23-c

Compound 23-c (40 mg, 55%) was obtained by using compound 23-d as raw material according to the method for preparing compound 1-c. LC-MS (ESI): m/z=319.0 [M+H]$^+$.

Synthesis of Compound 23

Compound 23 (20 mg, 39%) was obtained by using compound 23-c and compound 23-b as raw material according to the method for preparing compound 11. LC-MS (ESI): m/z=330.0 [M+H]$^+$. $^1$H NMR (400 MHz, CD$_3$OD): δ9.53 (s, 1H), 8.77 (s, 1H), 8.74 (d, J=5.2 Hz, 1H), 8.29 (s, 1H), 7.71 (d, J=7.8 Hz, 1H), 7.63 (t, J=8 Hz, 1H), 7.56 (d, J=9.2 Hz, 1H), 7.24 (d, J=7.6 Hz, 1H), 7.19 (dd, J$_1$=9.2 Hz, J$_2$=1.6 Hz, 1H), 7.16 (d, J=7.6 Hz, 1H), 2.47 (s, 3H).

Synthetic Route of Compound 24

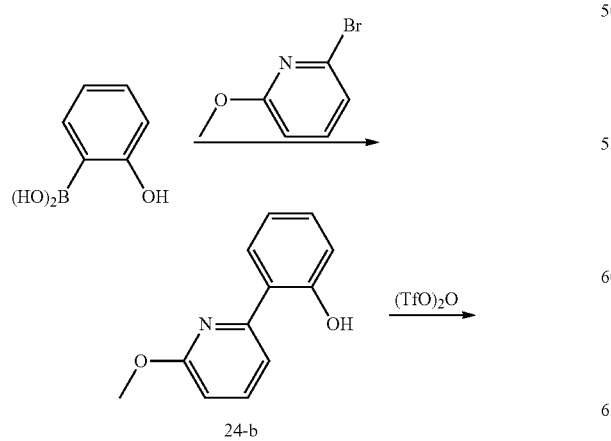

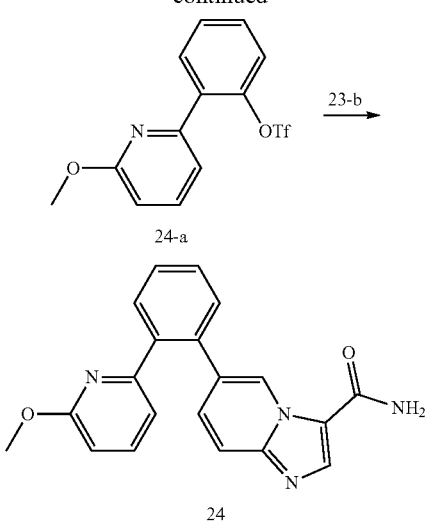

Synthesis of Compound 24-b

Compound 24-b (800 mg, 61%) was obtained by using 2-hydroxyphenylboronic acid and 2-bromo-6-methoxypyridine as raw material according to the method for preparing compound 1-e. LC-MS (ESI): m/z=202.1 [M+H]$^+$.

Synthesis of Compound 24-a

Compound 24-a (600 mg, 45%) was obtained by using compound 24-b as raw material according to the method for preparing compound 1-c. LC-MS (ESI): m/z=333.9 [M+H]$^+$.

Synthesis of Compound 24

Compound 24 (40 mg, 41%) was obtained as a white solid by compound 24-a and compound 23-b as raw material according to the method for preparing compound 11. LC-MS (ESI): m/z=345.0 [M+H]$^+$. $^1$H NMR (400 MHz, CD$_3$OD): δ9.46 (s, 1H), 8.28 (s, 1H), 7.68-7.73 (m, 1H), 7.55-7.76 (m, 4H), 7.50 (d, J=9.6 Hz, 1H), 7.20 (dd, J$_1$=9.6 Hz, J$_2$=2 Hz, 1H), 6.98 (d, J=7.2 Hz, 1H), 6.62 (d, J=8.4 Hz, 1H), 3.49 (s, 3H).

Synthetic Route of Compound 25

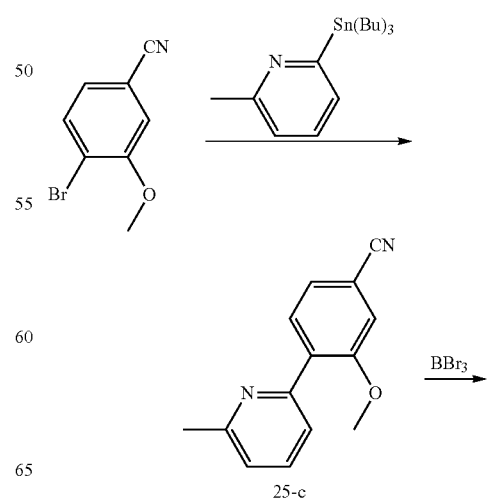

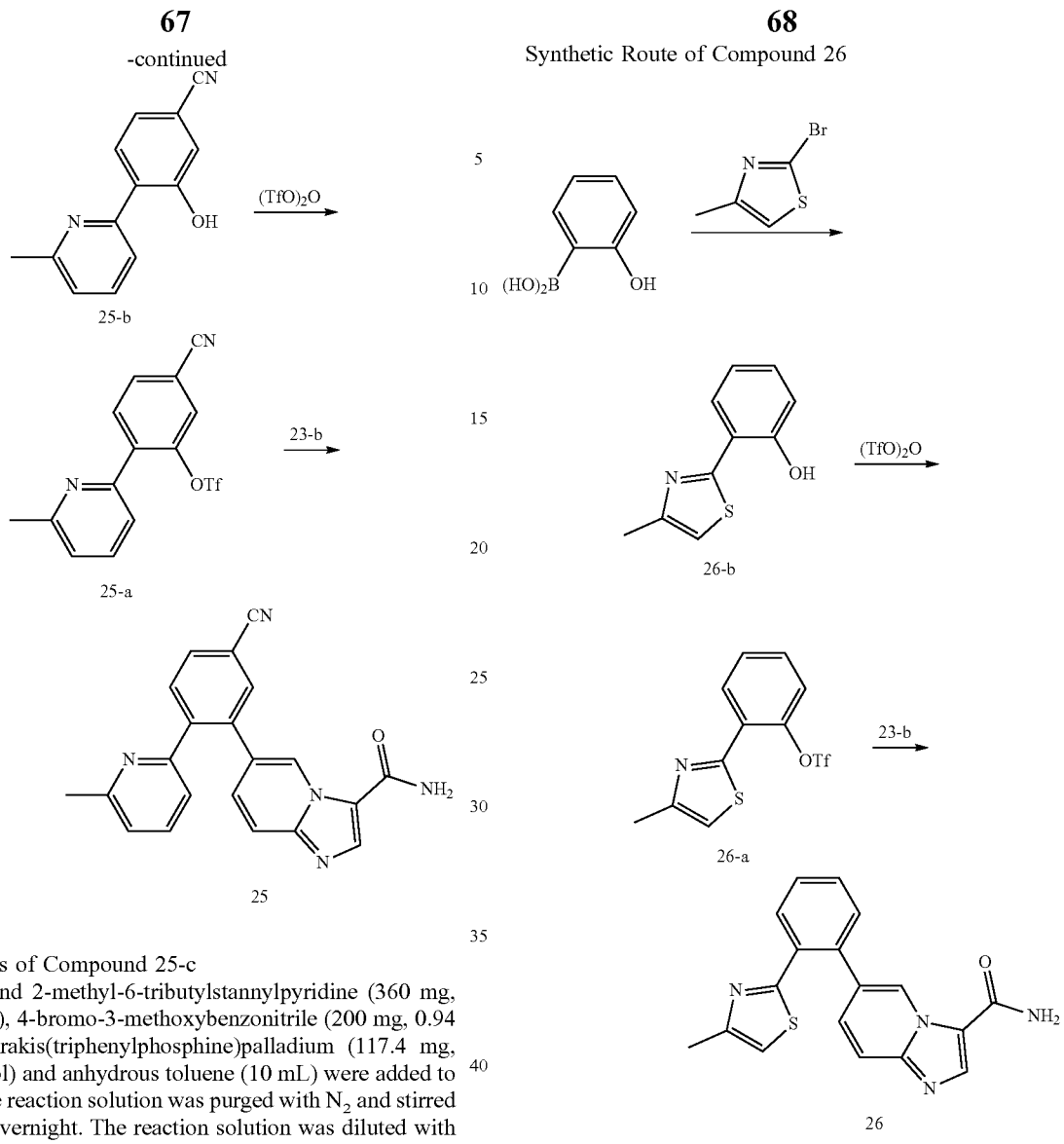

Synthetic Route of Compound 26

Synthesis of Compound 25-c

Compound 2-methyl-6-tributylstannylpyridine (360 mg, 0.94 mmol), 4-bromo-3-methoxybenzonitrile (200 mg, 0.94 mmol), tetrakis(triphenylphosphine)palladium (117.4 mg, 0.094 mmol) and anhydrous toluene (10 mL) were added to a flask. The reaction solution was purged with $N_2$ and stirred at 90° C. overnight. The reaction solution was diluted with ethyl acetate, washed with water and saturated brine, dried over anhydrous sodium sulfate, filtered and evaporated. The residue was purified by silica gel column chromatography (eluent: PE/EA=5/1) to give compound 20 (90 mg, 43%). LC-MS (ESI): m/z=225.1 [M+H]$^+$.

Synthesis of Compound 25-b

Compound 25-b (70 mg, 83%) was obtained by using compound 25-c as raw material according to the method for preparing compound 1-d. LC-MS (ESI): m/z=211.1 [M+H]$^+$.

Synthesis of Compound 25-a

Compound 25-a (70 mg, 61%) was obtained by using compound 25-b as raw material according to the method for preparing compound 1-c. LC-MS (ESI): m/z=342.9 [M+H]$^+$.

Synthesis of Compound 25

Compound 25 (30 mg, 42%) was obtained by using compound 25-a and compound 23-b as raw material according to the method for preparing compound 11. LC-MS (ESI): m/z=354.0 [M+H]$^+$. $^1$H NMR (400 MHz, CD$_3$OD): δ9.45 (s, 1H), 8.27 (s, 1H), 7.99 (s, 1H), 7.92 (d, J=8 Hz, 1H), 7.80 (d, J=8 Hz, 1H), 7.56 (t, J=7.6 Hz, 1H), 7.52 (d, J=9.2 Hz, 1H), 7.19 (d, J=8 Hz, 1H), 7.09 (d, J=8 Hz, 1H), 2.46 (s, 3H).

Synthesis of Compound 26-b

Compound 26-b (81 mg, 76%) was obtained as an oil by using 2-hydroxyphenylboronic acid and 2-bromo-4-methylthiazole as raw material according to the method for preparing compound 1-e. LC-MS (ESI): m/z=192.1 [M+H]$^+$.

Synthesis of Compound 26-a

Compound 26-a (143 mg, 85%) was obtained by using compound 26-b as raw material according to the method for preparing compound 1-c. LC-MS (ESI): m/z=323.9 [M+H]$^+$.

Synthesis of Compound 26

Compound 26 (60 mg, 40%) was obtained as a white solid by using compound 26-a and compound 23-b as raw material according to the method for preparing compound 11. LC-MS (ESI): m/z=335.0 [M+H]$^+$. $^1$H NMR (400 MHz, CDCl$_3$): δ 9.56 (s, 1H), 8.11 (s, 1H), 7.96-7.98 (m, 1H), 7.60-7.63 (m, 1H), 7.51-7.54 (m, 2H), 7.46-7.48 (m, 1H), 7.19 (dd, J=9.2, 1.7 Hz, 1H), 6.82 (s, 1H), 5.74 (s, 2H), 2.40 (s, 3H).

Synthetic Route of Compound 27

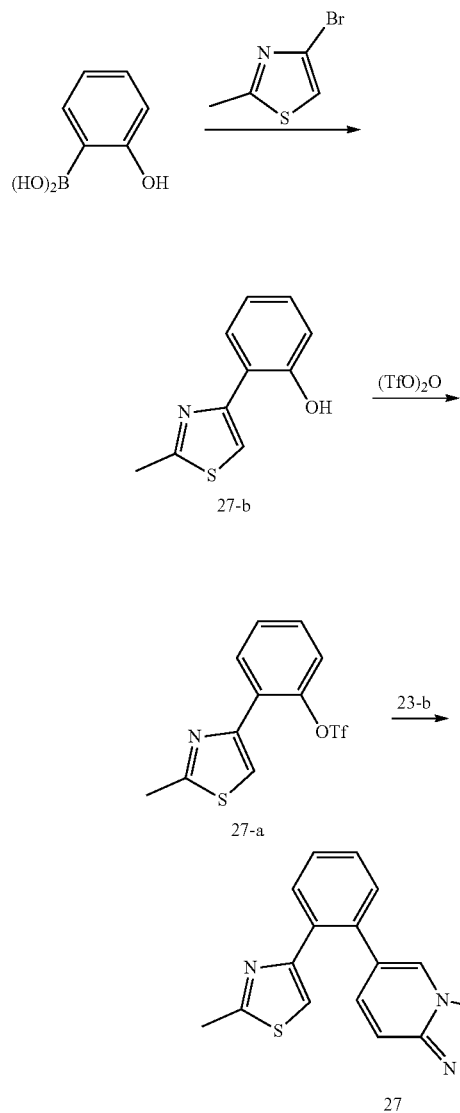

Synthesis of Compound 27-b

Compound 27-b (85 mg, 88%) was obtained by using 2-hydroxyphenylboronic acid and 2-bromo-2-methylthiazole as raw material according to the method for preparing compound 1-e. LC-MS (ESI): m/z=192.1 [M+H]$^+$.

Synthesis of Compound 27-a

Compound 27-a (75 mg, 52%) was obtained by using compound 27-b as raw material according to the method for preparing compound 1-c. LC-MS (ESI): m/z=324.0 [M+H]$^+$.

Synthesis of Compound 27

Compound 27 (30 mg, 39%) was obtained as a white solid by using compound 27-a and compound 23-b as raw material according to the method for preparing compound 11. LC-MS (ESI): m/z=335.0 [M+H]$^+$. $^1$H NMR (400 MHz, DMSO-d$_6$): δ9.45 (s, 1H), 8.34 (s, 1H), 7.83-7.76 (m, 1H), 7.58 (d, J=9.3 Hz, 1H), 7.55-7.43 (m, 3H), 7.08 (dd, J=9.2, 1.8 Hz, 1H), 7.04 (s, 1H), 2.57 (s, 2H), 2.08 (s, 3H).

Synthetic Route of Compound 28

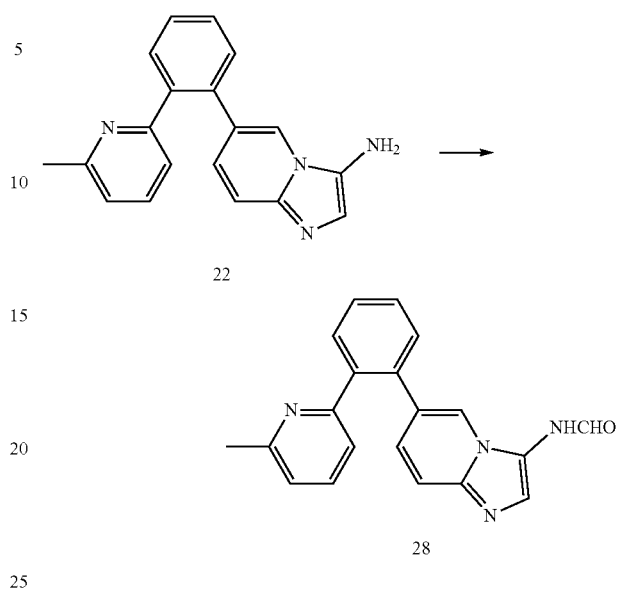

Synthesis of Compound 28

Compound 22 (100 mg, 0.33 mmol) was dissolved in ethyl formate (10 mL) and formic acid (5 mL). The reaction solution was heated to 65° C. and stirred for 2 hours. Then the reaction solution was cooled to room temperature, evaporated under reduced pressure to remove the organic solvent, diluted with saturated aqueous sodium bicarbonate solution (10 mL) and extracted with dichloromethane. The organic phase was combined, washed with water and brine respectively, dried over anhydrous sodium sulfate and evaporated under reduced pressure. The residue was purified by preparative thin layer chromatography (eluent: dichloromethane/methanol=10/1) to give compound 28 (35 mg, 32%). LC-MS (ESI): m/z=329.0 [M+H]$^+$. $^1$H NMR (400 MHz, CD$_3$OD): δ8.42 (s, 0.8H), 8.15 (s, 0.2H), 7.97 (m, 1H), 7.55-7.64 (m, 6H), 7.34-7.40 (m, 1H), 7.16-7.19 (m, 1H), 7.04-7.09 (m, 1H), 6.97-7.00 (m, 1H), 2.48 (s, 2.4H), 2.46 (s, 0.6H).

Synthetic Route of Compound 29

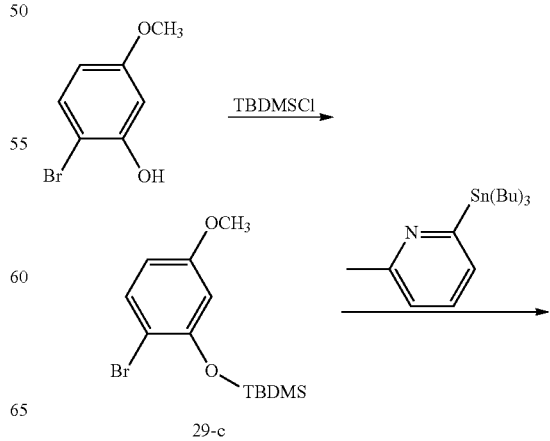

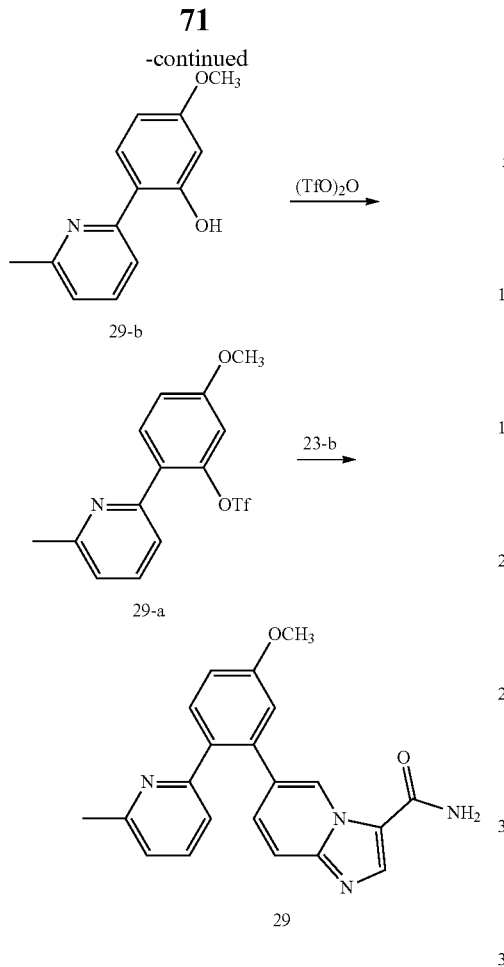

Synthesis of Compound 29

Compound 29 (20 mg, 39%) was obtained by using compound 29-a and compound 23-b as raw material according to the method for preparing compound 11. LC-MS (ESI): m/z=359.0 [M+H]$^+$. $^1$H NMR (400 MHz, CD$_3$OD): δ9.46 (s, 1H), 8.26 (s, 1H), 7.47-7.58 (m, 3H), 7.10-7.19 (m, 4H), 6.99 (d, J=8 Hz, 1H), 3.93 (s, 3H), 2.44 (s, 3H).

Synthetic Route of Compound 30

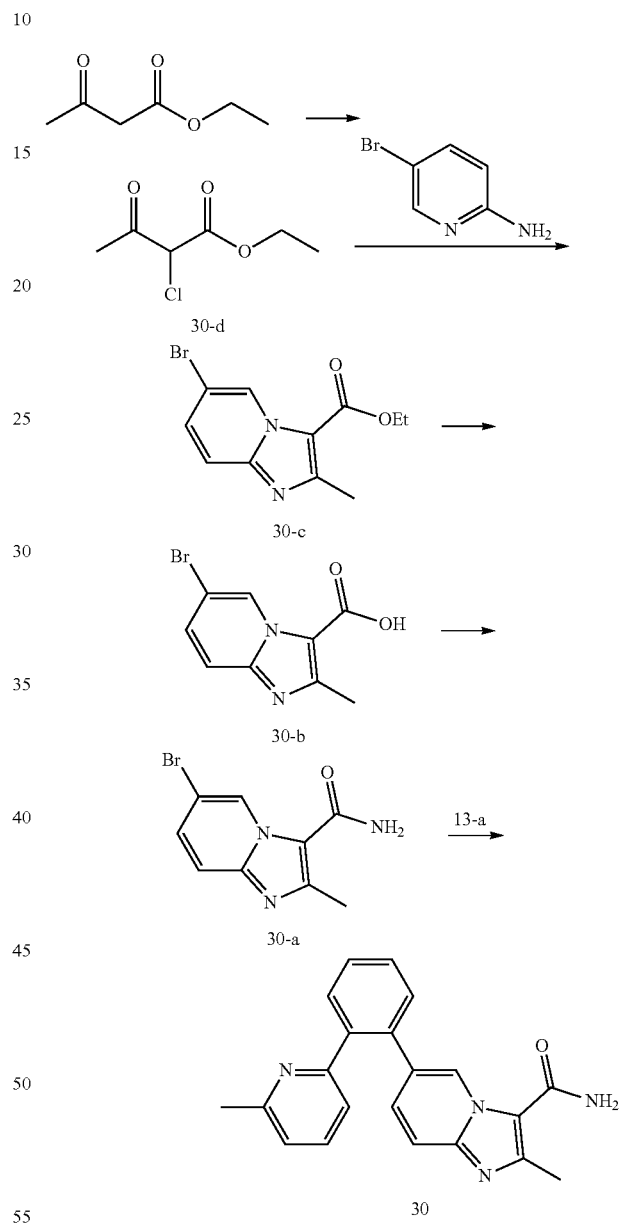

Synthesis of Compound 29-c tert-Butyldimethylsilyl chloride (TBDMSCl) (0.71 g, 4.73 mmol) and imidazole (0.4 g, 5.91 mmol) were added to a solution of 2-bromo-5-methoxyphenol (0.8 g, 3.94 mmol) in DMF (3 mL). After completion of the addition, the reaction solution was stirred at room temperature overnight. In the next day, water and ethyl acetate were added to the reaction solution, then the organic layer was separated and the aqueous layer was extracted with ethyl acetate. The organic layers were combined, washed with water and saturated brine, dried over anhydrous sodium sulfate, filtered and evaporated. The residue was purified by silica gel column chromatography to give compound 29-c (1.0 g, 80%). LC-MS (ESI): m/z=317.0 [M+H]$^+$.

Synthesis of Compound 29-b

Compound 2-methyl-6-tributylstannylpyridine (602 mg, 1.58 mmol), compound 29-c (500 mg, 1.58 mmol), tetrakis(triphenylphosphine)palladium (196.1 mg, 0.158 mmol) and anhydrous toluene (10 mL) were added to a flask. The reaction solution was purged with N$_2$ and stirred at 90° C. overnight. The reaction solution was diluted with ethyl acetate, washed with water and saturated brine, dried over anhydrous sodium sulfate, filtered and evaporated. The residue was purified by silica gel column chromatography (eluent: PE/EA=10/1) to give compound 29-b as an oil (150 mg, 44%). LC-MS (ESI): m/z=216.1 [M+H]$^+$.

Synthesis of Compound 29-a

Compound 29-a (150 mg, 62%) was obtained by using compound 29-b as raw material according to the method for preparing compound 1-c. LC-MS (ESI): m/z=348.0 [M+H]$^+$.

Synthesis of Compound 30-d

Sulfuryl chloride (1.4 mL, 17.3 mmol) was slowly added dropwise to a solution of ethyl acetoacetate (2 mL, 15.7 mmol) in carbon tetrachloride (10 mL) at room temperature. After completion of the addition, the reaction solution was stirred at room temperature for 1 hour. Then the reaction solution was evaporated under reduced pressure to gave compound 30-d as a colorless oil (2.5 g, 97%). $^1$H NMR (400 MHz, CDCl$_3$): δ 4.76 (s, 1H), 4.30 (q, J=7.6 Hz, 2H), 2.39 (s, 3H), 1.27-1.38 (m, 3H).

Synthesis of Compound 30-c

Compound 30-d (1.65 g, 10 mmol), 2-amino-5-bromopyridine (1.73 g, 10 mmol) and ethanol (10 mL) were added to a microwave tube. After completion of the addition, the reaction solution was stirred under microwave (150 W) at 120° C. for 20 minutes. The reaction solution was cooled to room temperature, poured into ice water (100 mL), and then stirred for 1 hour. The mixture was filtered, and the filter cake was washed with water and dried to give compound 30-c as a pale yellow solid (1.5 g, 53%). LC-MS (ESI): m/z=282.9 [M+H]$^+$.

Synthesis of Compound 30-b

Compound 30-c (1.5 g, 5.3 mmol) was dissolved in methanol (5 mL) and THF (5 mL), followed by addition of aqueous sodium hydroxide solution (2 M, 5 mL). The reaction solution was stirred at room temperature for 2 hours. Then the reaction solution was evaporated under reduced pressure to remove the organic solvent, diluted with water (10 mL) and dichloromethane (10 mL), then the aqueous layer was separated and the organic layer was removed. The aqueous layer was cooled to 0° C., neutralized to pH of 5-6 with hydrochloric acid (6 M), extracted with chloroform/isopropanol (3/1). The organic phase was washed with saturated brine, dried over anhydrous sodium sulfate, filtered and evaporated to give compound 30-b as a gray solid (1.1 g, 81%) LC-MS (ESI): m/z=254.9 [M+H]$^+$.

Synthesis of Compound 30-a

Compound 30-a (120 mg, 60%) was obtained by using compound 30-b as raw material according to the method for preparing compound 23-f. LC-MS (ESI): m/z=253.9 [M+H]$^+$.

Synthesis of Compound 30

Compound 30 (30 mg, 45%) was obtained by using compound 30-a as raw material according to the method for preparing compound 13. LC-MS (ESI): m/z=343.0 [M+H]$^+$.
$^1$H NMR (400 MHz, CD$_3$OD): δ9.13 (s, 1H), 7.55-7.64 (m, 5H), 7.36 (d, J=9.2 Hz, 1H), 7.16 (d, J=8 Hz, 1H), 7.11 (dd, J$_1$=9.2 Hz, J$_2$=1.2 Hz, 1H), 7.05 (d, J=8 Hz, 1H), 2.67 (s, 3H), 2.47 (s, 3H).

Synthetic Route of Compound 31

Synthesis of Compound 31-a

A mixture of compound 2-bromofuranylpropionaldehyde dimethyl acetal (1.0 g, 4.74 mmol) and hydrochloric acid (1 M, 3 mL) was heated to 90° C. and stirred for 1 hour. The reaction solution was cooled to room temperature and then neutralized to pH of 7 with a solid of sodium bicarbonate. Then 2-amino-5-bromopyridine (360 mg, 2.08 mmol) and methanol (5 mL) were added successively, and the reaction solution was heated to 90° C. and stirred overnight. The reaction solution was evaporated under reduced pressure to remove the organic solvent, diluted with water (10 mL) and dichloromethane. The organic layer was separated, washed with water, saturated brine, dried over anhydrous sodium sulfate and evaporated under reduced pressure to give a crude product, which was purified by silica gel column chromatography to give compound 31-a as a gray solid (250 mg, 57%). LC-MS (ESI): m/z=210.9 [M+H]$^+$.

Synthesis of Compound 31

Compound 31 (30 mg, 42%) was obtained by using compound 31-a as raw material according to the method for preparing compound 13. LC-MS (ESI): m/z=300.1 [M+H]$^+$.
$^1$H NMR (400 MHz, CD$_3$OD): δ7.98 (s, 1H), 7.55-7.63 (m, 5H), 7.33-7.36 (m, 2H), 7.18 (d, J=7.6 Hz, 1H), 7.06 (d, J=7.6 Hz, 1H), 6.98 (d, J=9.2 Hz, 1H), 2.48 (s, 3H), 2.42 (s, 3H).

Synthetic Route of Compound 32

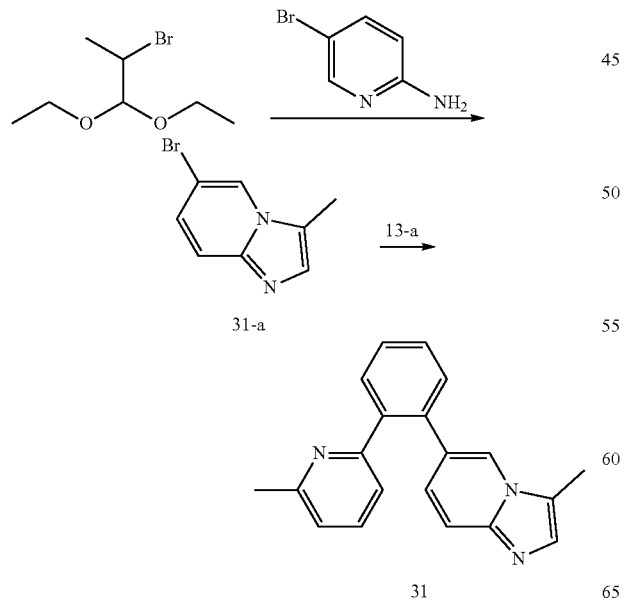

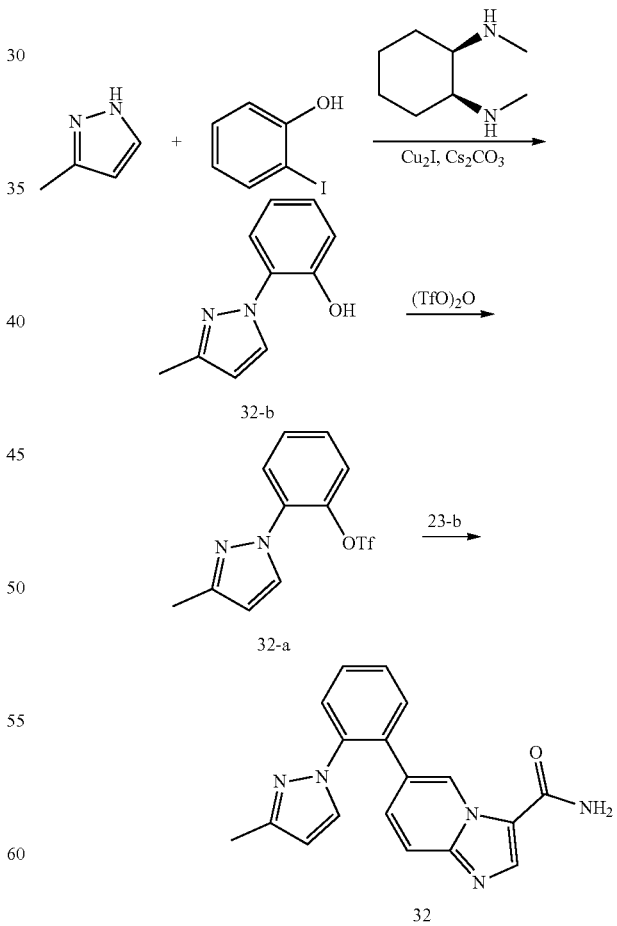

Synthesis of Compound 32-b

3-Methylpyrazole (300 mg, 3.65 mmol), o-iodophenol (965 mg, 4.38 mmol), trans-1,2-dimethylaminocyclohexane (155 mg, 1.1 mmol), cuprous iodide (70 mg, 0.365 mmol), Cs$_2$CO$_3$ (2.38 g, 7.3 mmol) and N,N-dimethylformamide (10 mL) were added to a flask. The reaction solution was purged with nitrogen and stirred at 110° C. overnight. The reaction solution was diluted with water (50 mL) and extracted with EtOAc (30 mL). The organic phase was dried over anhydrous sodium sulfate, filtered and evaporated. The residue was purified by silica gel column chromatography (eluent: PE/EA=10/1) to give compound 32-b (125 mg, 20%) as an oil. LC-MS (ESI): m/z=175.1 [M+H]$^+$.

Synthesis of Compound 32-a

Compound 32-a (182 mg, 83%) was obtained by using compound 32-b as raw material according to the method for preparing compound 1-c. LC-MS (ESI): m/z=307.0 [M+H]$^+$.

Synthesis of Compound 32

Compound 32 (18 mg, 20%). was obtained by using compound 32-a and compound 23-b as raw material according to the method for preparing compound 11. LC-MS (ESI): m/z=318.0 [M+H]$^+$. $^1$H NMR (400 MHz, DMSO-d$_6$): δ9.44 (s, 1H), 8.33 (s, 1H), 7.62-7.55 (m, 5H), 7.50 (d, J=2.2 Hz, 1H), 6.88-6.86 (dd, J=2.4 Hz, 1H), 6.08 (d, J=2.4 Hz, 1H), 2.54 (s, 2H), 2.16 (s, 3H).

Synthetic Route of Compound 33

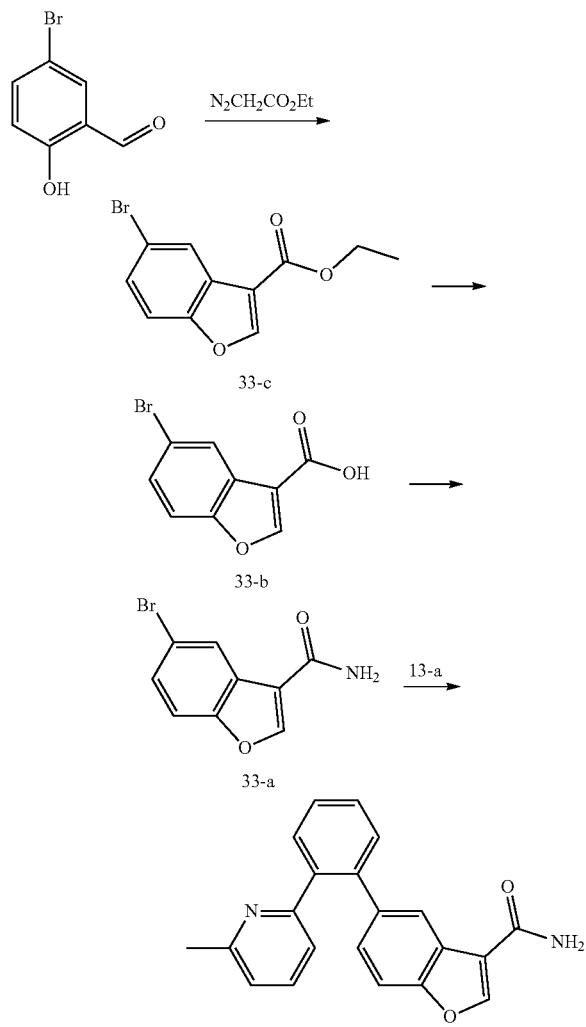

Synthesis of Compound 33-c

A solution of tetrafluoroboric acid in diethyl ether (50%-55%, 162 mg, 0.5 mmol) was added to a solution of 5-bromo-2-hydroxybenzaldehyde (1.0 g, 5 mmol) in dichloromethane (30 mL), followed by addition of a solution of ethyl diazoacetate (860 mg, 7.4 mmol) in dichloromethane (30 mL). The reaction temperature was controlled not more than 38° C. Nitrogen was produced in the reaction, and the reaction solution was concentrated when no more nitrogen was produced. 98% Concentrated sulfuric acid (650 mg, 6.5 mmol) was added under stirring. The resulting mixture was stirred for 20 minutes, neutralized with saturated aqueous sodium carbonate solution, and stirred for 10 minutes. Then a yellow solid precipitated, which was obtained by filtration to give compound 33-c as a yellow solid (830 mg, 62%). $^1$H NMR (400 MHz, CDCl$_3$): δ8.25 (s, 1H), 8.21 (d, J=1.9 Hz, 1H), 7.47 (dd, J=1.6 Hz, 1H), 7.41 (d, J=8.8 Hz, 1H), 4.42 (q, 2H), 1.43 (t, 3H).

Synthesis of Compound 33-b

Compound 33-b (716 mg, 97%) was obtained by using compound 33-c as raw material according to the method for preparing compound 30-b. LC-MS (ESI): m/z=242.0 [M+H]$^+$.

Synthesis of Compound 33-a

Compound 33-a (270 mg, 37%) was obtained by using compound 33-b as raw material according to the method for preparing compound 23-f. LC-MS (ESI): m/z=241.9 [M+H]$^+$.

Synthesis of Compound 33

Compound 33 (10 mg, 15%) was obtained by using compound 33-a as raw material according to the method for preparing compound 13. LC-MS (ESI): m/z=329.0 [M+H]$^+$. $^1$H NMR (400 MHz DMSO-d$_6$): δ8.53 (s, 1H), 7.96 (s, 1H), 7.77 (s, 1H), 7.62 (m, 1H), 7.57-7.44 (m, 4H), 7.35-7.39 (m, 2H), 7.04 (m 1H), 6.95 (m, 1H), 6.66 (m, 1H), 2.44 (s, 3H).

Synthetic Route of Compound 34

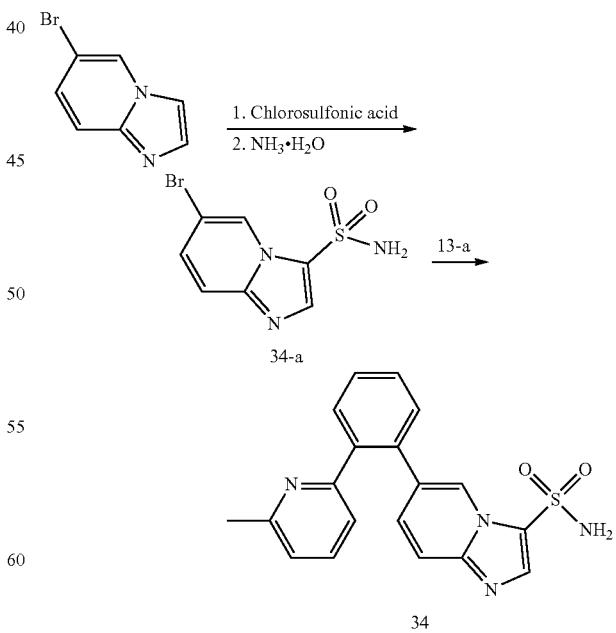

Synthesis of Compound 34-a

Chlorosulfonic acid (5 mL) was slowly added dropwise to a solution of 6-bromo-imidazo[1,2-a]pyridine (0.5 g, 2.54 mmol) in chloroform (10 mL). The reaction solution was heated to reflux and stirred overnight. The reaction solution was cooled to room temperature and evaporated under reduced pressure. The residue was dissolved in dichloromethane (10 mL), and ammonium hydroxide (10 mL) was added dropwise under stirring. The organic layer was separated and the aqueous layer was extracted with dichloromethane. The combined organic phase was washed with water and saturated brine, dried over anhydrous sodium sulfate and evaporated under reduced pressure to give compound 34-a (250 mg, 36%). LC-MS (ESI): m/z=276.0 [M+H]⁺.

Synthesis of Compound 34

Compound 34 (15 mg, 11%) was obtained by using compound 34-a as raw material according to the method for preparing compound 13. LC-MS (ESI): m/z=364.9 [M+H]⁺. ¹H NMR (400 MHz, CD₃OD): δ8.59 (s, 1H), 8.01 (s, 1H), 7.55-7.63 (m, 6H), 7.26 (d, J=9.6 Hz, 1H), 7.16 (d, J=7.6 Hz, 1H), 7.08 (d, J=8.0 Hz, 1H), 2.44 (s, 3H).

Synthetic Route of Compound 35

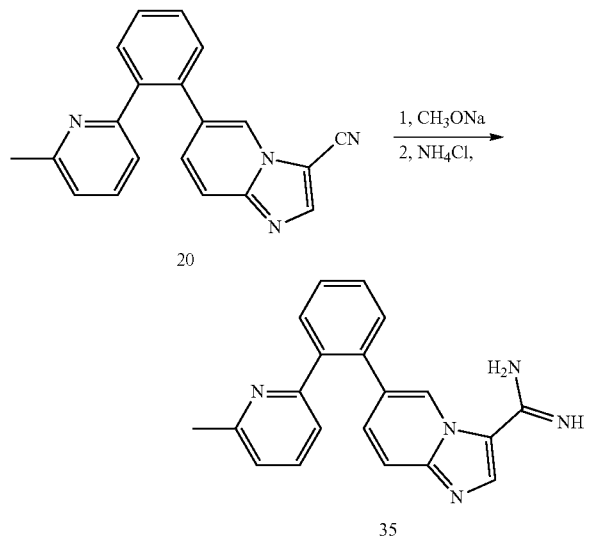

Synthesis of Compound 35

A mixture of compound 20 (80 mg, 0.26 mmol), sodium methoxide (3 mg, 0.05 mmol) and methanol (10 mL) was stirred at room temperature overnight, followed by addition of ammonium chloride (16 mg, 0.29 mmol) at 90° C. The reaction solution was cooled to room temperature and evaporated under reduced pressure. The residue was purified by preparative HPLC to give compound 35 as a white solid (20 mg, 48%). LC-MS (ESI): m/z=328.0 [M+H]⁺. ¹H NMR (400 MHz, DMSO-d₆): δ9.96 (s, 1H), 8.15 (s, 1H), 7.71-7.40 (m, 6H), 7.09 (m, 1H), 6.92 (m, 2H), 6.78 (s, 1H), 6.26 (m, 2H), 2.39 (s, 3H).

Synthetic Route of Compound 36

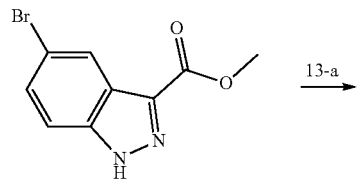

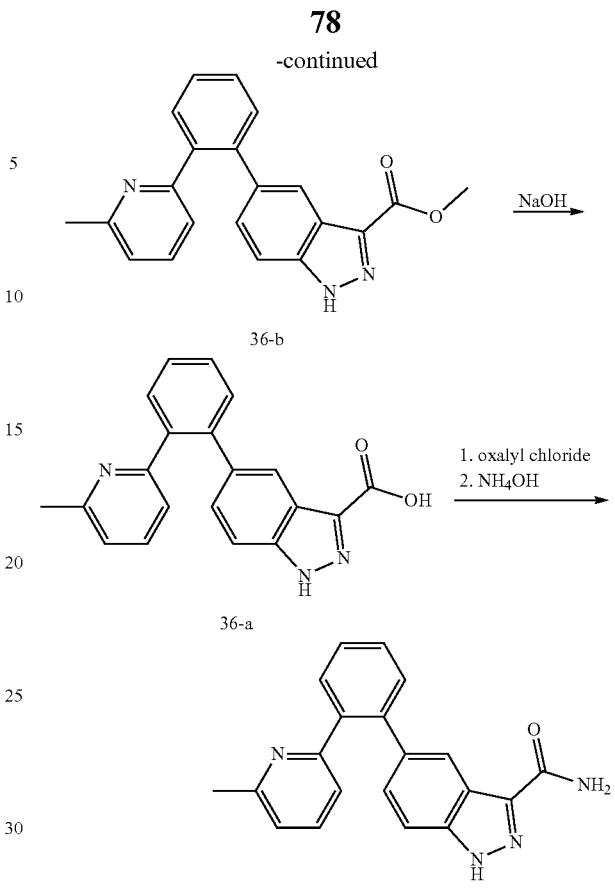

Synthesis of Compound 36-a and 36-b

A mixture of compound 13-a (80.2 mg, 0.38 mmol), methyl 5-bromo-1H-indazole-3-carboxylate (80 mg, 0.31 mmol), [1,1'-bis(diphenylphosphino)ferrocene]palladium dichloride (25.6 mg, 031 mmol), Na₂CO₃ (83.1 mg, 0.78 mmol), dioxane (10.0 mL) and water (3.0 mL) was stirred under nitrogen atmosphere at 90° C. overnight. The reaction solution was cooled to room temperature and evaporated under reduced pressure. The residue of compound 36-b was dissolved in methanol (2.0 mL) and THF (2 mL), followed by addition of aqueous sodium hydroxide solution (2 M, 2 mL). The reaction solution was stirred at room temperature overnight. After completion of the reaction, the reaction solution was evaporated under reduced pressure to remove the organic solvent, diluted with water (10 mL) and dichloromethane (10 mL) and the organic layer was discarded. The aqueous layer was cooled to 0° C., neutralized to pH of 5-6 with hydrochloric acid (6 M), extracted with chloroform/isopropanol (3/1). The organic phase was washed with saturated brine, dried over anhydrous sodium sulfate and evaporated under reduced pressure to give compound 36-a as a pale yellow solid (60 mg, yield 58% for two steps). LC-MS (ESI): m/z=330.0 [M+H]⁺.

Synthesis of Compound 36

Compound 36 (20 mg, 33.4%) was obtained by using compound 36-a as raw material according to the method for preparing compound 2. LC-MS (ESI): m/z=329.0 [M+H]⁺. ¹H NMR (400 MHz, DMSO-d₆): δ 13.51 (s, 1H), 8.08 (s, 1H), 7.71 (s, 1H), 7.63 (dd, J₁=6.4 Hz, J₂=2.4 Hz, 1H), 7.45-7.52 (m, 3H), 7.41 (d, J=8.8 Hz, 1H), 7.32-7.36 (m, 2H), 7.03 (d, J=7.6 Hz, 1H), 6.97 (dd, J₁=8.8 Hz, J₂=1.6 Hz, 1H), 6.66 (d, J=7.6 Hz, 1H), 2.44 (s, 3H).

Synthetic Route of Compound 37

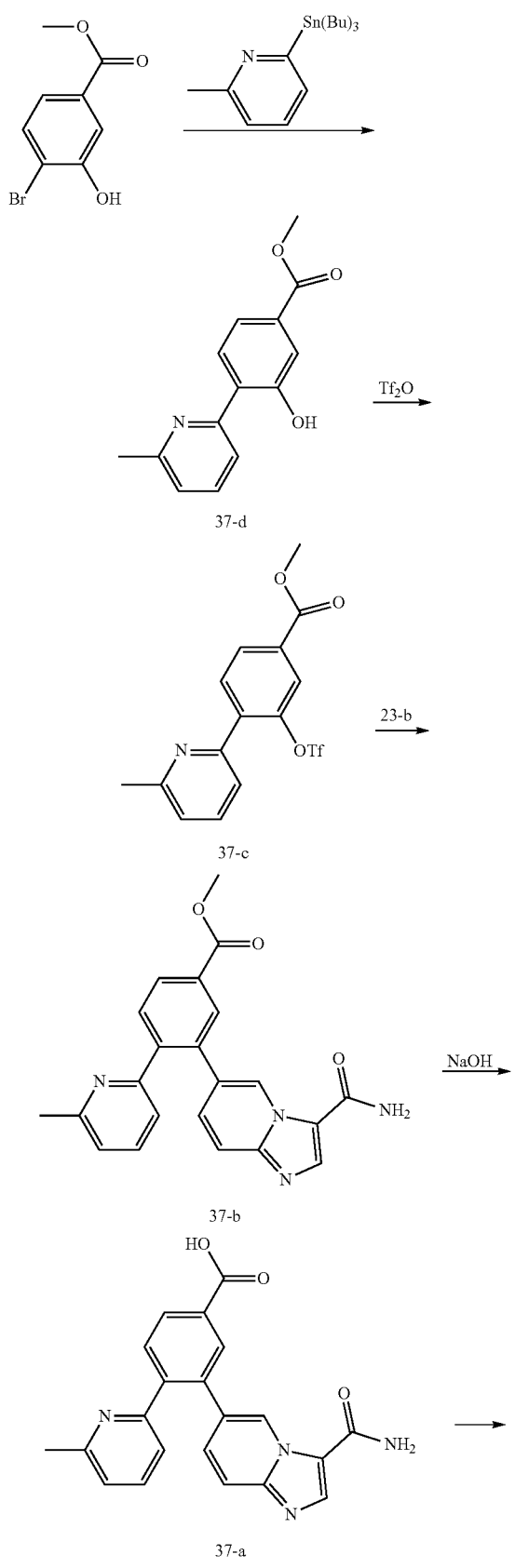

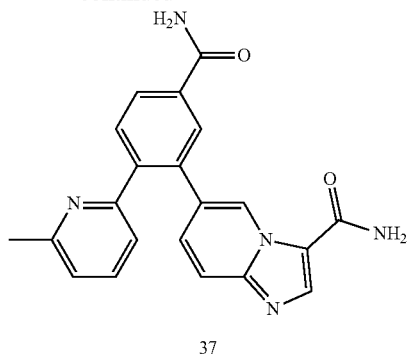 [SMILES: Cc1cccc(-c2ccc(C(N)=O)cc2-c2ccc3ncc(C(N)=O)n3c2)n1]

Synthesis of Compound 37-d

Compound 37-d (600 mg, 81%) was obtained by using methyl 4-bromo-3-hydroxybenzoate as raw material according to the method for preparing compound 25-c. LC-MS (ESI): m/z=244.1 [M+H]⁺.

Synthesis of Compound 37-c

Compound 37-c (300 mg, 65%) was obtained by using compound 37-d as raw material according to the method for preparing compound 1-c. LC-MS (ESI): m/z=375.9 [M+H]⁺.

Synthesis of Compound 37-a and 37-b

A mixture of compound 37-c (200 mg, 0.8 mmol), compound 23-b (196.6 mg, 0.96 mmol), [1,1'-bis(diphenylphosphino)ferrocene]palladium dichloride (65.3 mg, 0.08 mmol), $Na_2CO_3$ (211.8 mg, 2.0 mmol), dioxane (10.0 mL) and water (2.0 mL) was stirred under nitrogen atmosphere at 90° C. overnight. The reaction solution was cooled to room temperature and evaporated under reduced pressure. The residue of compound 37-b was dissolved in methanol (2.0 mL) and THF (2 mL), followed by addition of aqueous sodium hydroxide solution (2 M, 10 mL). The reaction solution was stirred at room temperature overnight. After completion of the reaction, the reaction solution was evaporated under reduced pressure to remove the organic solvent, diluted with water (10 mL) and dichloromethane (10 mL) and the organic layer was discarded. The aqueous layer was cooled to 0° C., neutralized to pH of 5-6 with hydrochloric acid (6 M), extracted with chloroform/isopropanol (3/1). The organic phase was washed with saturated brine, dried over anhydrous sodium sulfate and evaporated under reduced pressure to give compound 37-a as a pale yellow solid (200 mg, yield 67% for two steps). LC-MS (ESI): m/z=373.0 [M+H]⁺.

Synthesis of Compound 37

Compound 37 (10 mg, 20%) was obtained by using compound 37-a as raw material according to the method for preparing compound 2. LC-MS (ESI): m/z=372.0 [M+H]⁺. ¹H NMR (400 MHz, $CD_3OD$): δ9.36 (s, 1H), 8.16 (s, 1H), 8.00 (d, J=1.6 Hz, 1H), 7.97 (dd, $J_1$=8 Hz, $J_2$=1.2 Hz, 1H), 7.62 (d, J=8 Hz, 1H), 7.48 (t, J=8 Hz, 1H), 7.41 (d, J=9.2 Hz, 1H), 7.10 (d, J=9.2 Hz, 1H), 7.07 (d, J=7.6 Hz, 1H), 6.98 (d, J=7.6 Hz, 1H), 2.35 (s, 3H).

Synthetic Route of Compound 38

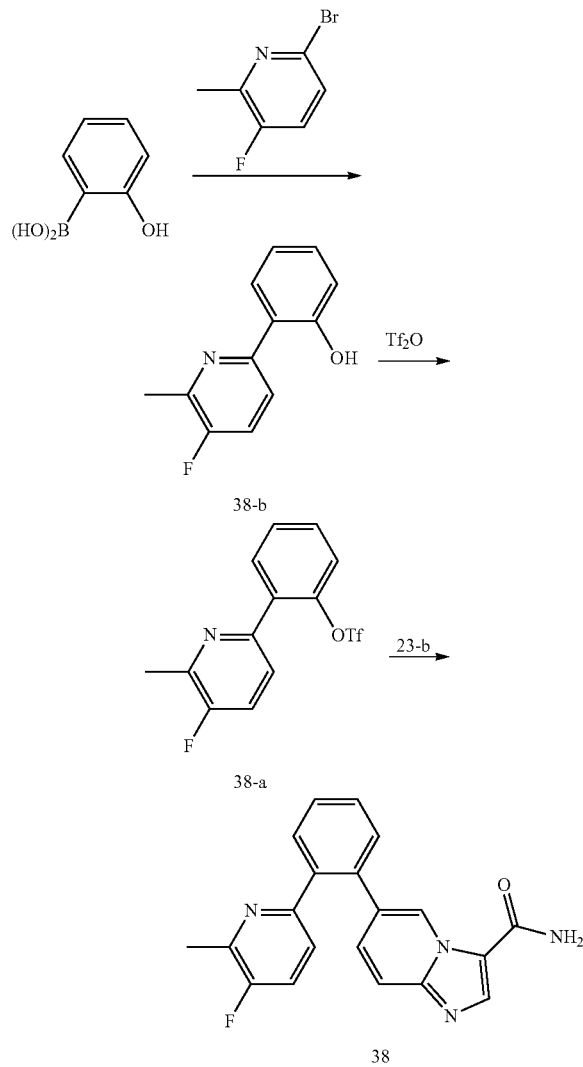

Synthetic Route of Compound 39

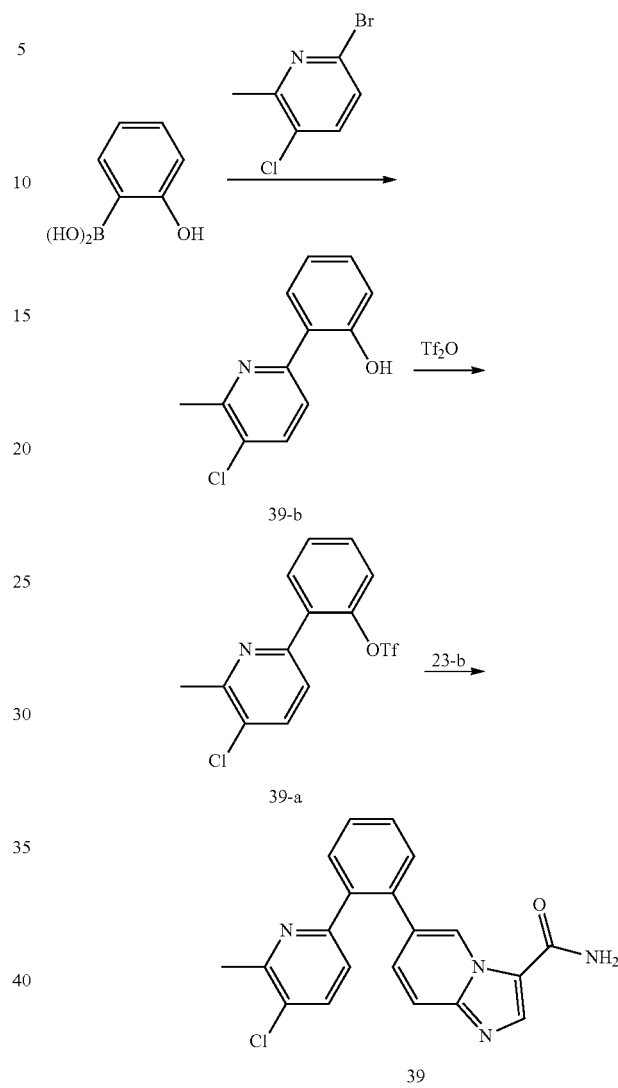

Synthesis of Compound 38-b

Compound 38-b (160 mg, 79%) was obtained by using 2-hydroxyphenylboronic acid and 6-bromo-3-fluoro-2-methylpyridine as raw material according to the method for preparing compound 1-e. LC-MS (ESI): m/z=204.1 [M+H]$^+$.

Synthesis of Compound 38-a

Compound 38-a (222 mg, 84%) was obtained by using compound 38-b as raw material according to the method for preparing compound 1-c. LC-MS (ESI): m/z=336.0 [M+H]$^+$.

Synthesis of Compound 38

Compound 38 (30 mg, 29%) was obtained as a white solid by using compound 38-a and compound 23-b as raw material according to the method for preparing compound 11. LC-MS (ESI): m/z=347.0 [M+H]$^+$. $^1$H NMR (400 MHz, DMSO-$d_6$): δ 9.38 (s, 1H), 8.32 (s, 1H), 7.93 (m, 1H), 7.68-7.62 (m, 1H), 7.59-7.51 (m, 4H), 7.45 (t, J=9.0 Hz, 1H), 7.41-7.29 (m, 1H), 7.09-7.00 (m, 2H), 2.36 (d, J=2.7 Hz, 3H).

Synthesis of Compound 39-b

Compound 39-b (100 mg, 94%) was obtained by using 2-hydroxyphenylboronic acid and 6-bromo-3-chloro-2-methylpyridine as raw material according to the method for preparing compound 1-e. LC-MS (ESI): m/z=220.1 [M+H]$^+$.

Synthesis of Compound 39-a

Compound 39-a (153 mg, 96%) was obtained by using compound 39-b as raw material according to the method for preparing compound 1-c. LC-MS (ESI): m/z=351.9 [M+H]$^+$.

Synthesis of Compound 39

Compound 39 (13 mg, 8%) was obtained as a white solid by using compound 39-a and compound 23-b as raw material according to the method for preparing compound 11. LC-MS (ESI): m/z=363.0 [M+H]$^+$. $^1$H NMR (400 MHz, DMSO-$d_6$): δ 9.40 (s, 1H), 8.32 (s, 1H), 7.99-7.88 (m, 1H), 7.69-7.67 (m, 2H), 7.60-7.55 (m, 4H), 7.41-7.29 (m, 1H), 7.10-6.98 (m, 2H), 2.46 (s, 3H).

Synthetic Route of Compound 40

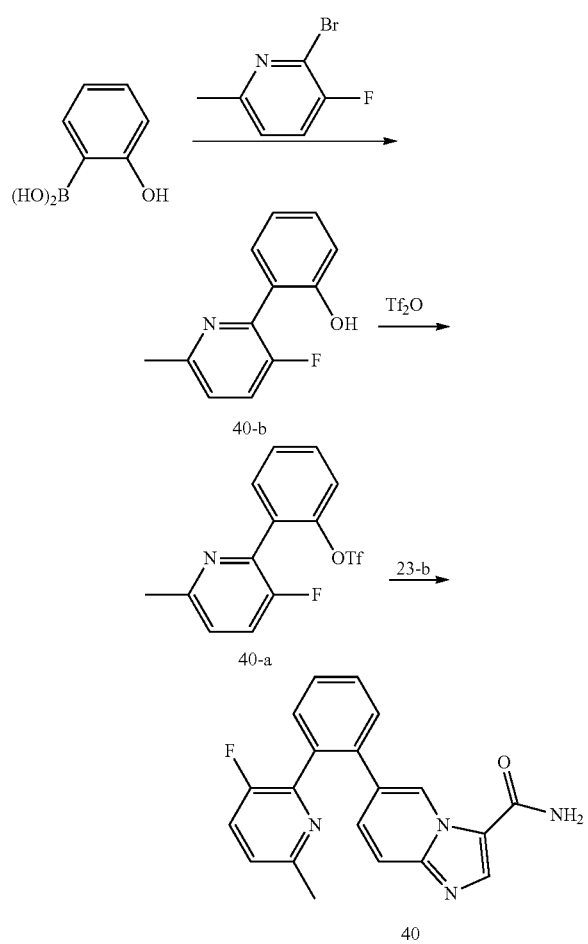

Synthesis of Compound 40-b

Compound 40-b (88 mg, 82%) was obtained by using 2-hydroxyphenylboronic acid and 2-bromo-3-fluoro-6-methylpyridine as raw material according to the method for preparing compound 1-e. LC-MS (ESI): m/z=204.1 [M+H]$^+$.

Synthesis of Compound 40-a

Compound 40-a (141 mg, 97%) was obtained by using compound 40-b as raw material according to the method for preparing compound 1-c. LC-MS (ESI): m/z=336.0 [M+H]$^+$.

Synthesis of Compound 40

Compound 40 (30 mg, 21%) was obtained as a white solid by using compound 40-a and compound 23-b as raw material according to the method for preparing compound 11. LC-MS (ESI): m/z=347.0 [M+H]$^+$. $^1$H NMR (400 MHz, DMSO-d$_6$): δ 9.30 (s, 1H), 8.30 (s, 1H), 7.90 (m, 1H), 7.73-7.51 (m, 5H), 7.49-7.31 (m, 2H), 7.22 (dd, J=8.5, 3.6 Hz, 1H), 7.13 (dd, J=9.3, 1.8 Hz, 1H), 2.44 (s, 3H).

Synthetic Route of Compound 41

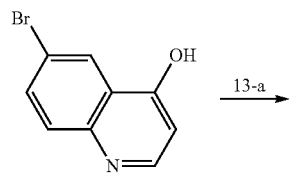

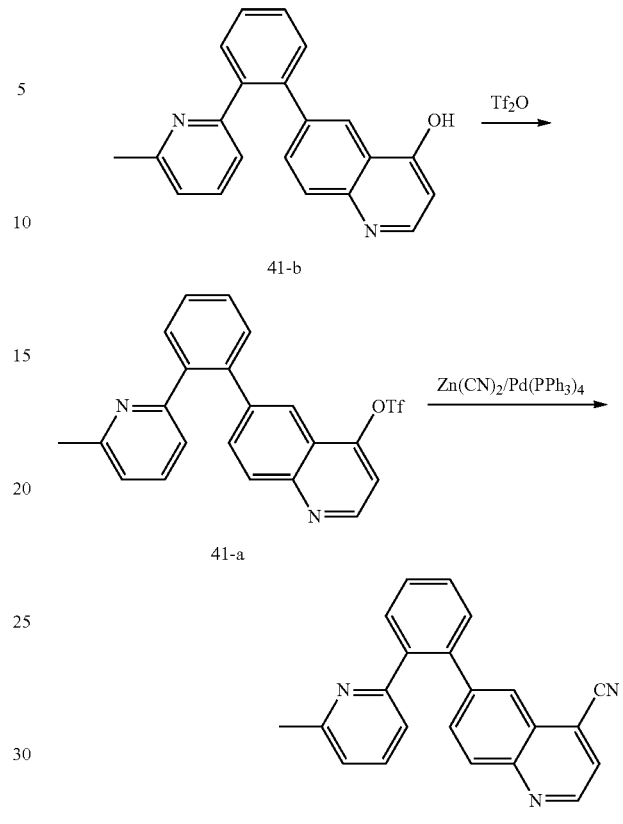

Synthesis of Compound 41-b

Compound 41-b (125 mg, 43%) was obtained by using 6-bromoquinolin-4-ol as raw material according to the method for preparing compound 13. LC-MS (ESI): m/z=313.0 [M+H]$^+$. $^1$H NMR (400 MHz, DMSO-d$_6$): δ 11.72 (s, 1H), 7.89 (m, 2H), 7.62 (m, 1H), 7.44 (m, 4H), 7.24 (m, 1H), 7.07 (m, 1H), 6.74 (m, 1H), 6.01 (m, 1H), 2.43 (s, 3H).

Synthesis of Compound 41-a

Compound 41-a (134 mg, 78%) was obtained by using compound 41-b as raw material according to the method for preparing compound 1-c. LC-MS (ESI): m/z=444.9 [M+H]$^+$.

Synthesis of Compound 41

A mixture of compound 41-a (134 mg, 0.3 mmol), zinc cyanide (71 mg, 0.6 mmol), Pd(PPh$_3$)$_4$ (35 mg, 0.03 mmol) and DMF (10 mL) was stirred under nitrogen atmosphere at 120° C. overnight. The reaction solution was cooled to room temperature, diluted with water (60 mL) and extracted with ethyl acetate (2×30 mL). The organic phase was combined, dried over anhydrous sodium sulfate and evaporated under reduced pressure. The residue was purified by preparative HPLC to give compound 41 as white solid (43.8 mg, 45%). LC-MS (ESI): m/z=322.0 [M+H]$^+$. $^1$H NMR (400 MHz, CD$_3$OD): δ8.99 (d, J=4.4 Hz, 1H), 8.05 (d, J=8.7 Hz, 1H), 7.91 (d, J=4.4 Hz, 1H), 7.87 (d, J=1.7 Hz, 1H), 7.75 (dd, J=8.8, 1.9 Hz, 1H), 7.70-7.57 (m, 4H), 7.49 (t, J=7.7 Hz, 1H), 7.14 (d, J=7.7 Hz, 1H), 6.94 (d, J=7.7 Hz, 1H), 2.45 (s, 3H).

Synthetic Route of Compound 42

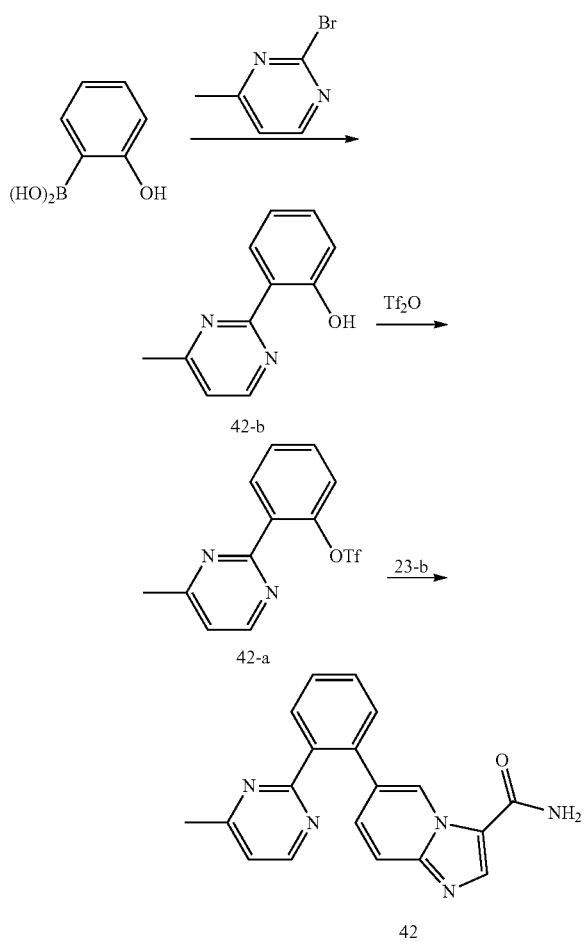

Synthesis of Compound 42-b

Compound 42-b (130 mg, 60%) was obtained by using 2-hydroxyphenylboronic acid and 2-bromo-3-fluoro-4-methylpyridine as raw material according to the method for preparing compound 1-e. LC-MS (ESI): m/z=187.1 [M+H]$^+$.

Synthesis of Compound 42-a

Compound 42-a (95 mg, 43%) was obtained by using compound 42-b as raw material according to the method for preparing compound 1-c. LC-MS (ESI): m/z=318.9 [M+H]$^+$.

Synthesis of Compound 42

Compound 42 (12 mg, 12%) was obtained as a white solid by using compound 42-a and compound 23-b as raw material according to the method for preparing compound 11. LC-MS (ESI): m/z=330.1 [M+H]$^+$. $^1$H NMR (400 MHz, CD$_3$OD): δ 9.37 (m, 1H), 8.50 (d, J=5.2 Hz, 1H), 8.26 (s, 1H), 7.85 (m, 1H), 7.62-7.60 (m, 3H), 7.53 (dd, J=9.3, 0.7 Hz, 1H), 7.26-7.19 (m, 2H), 2.41 (s, 3H).

Synthetic Route of Compound 43

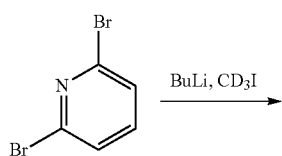

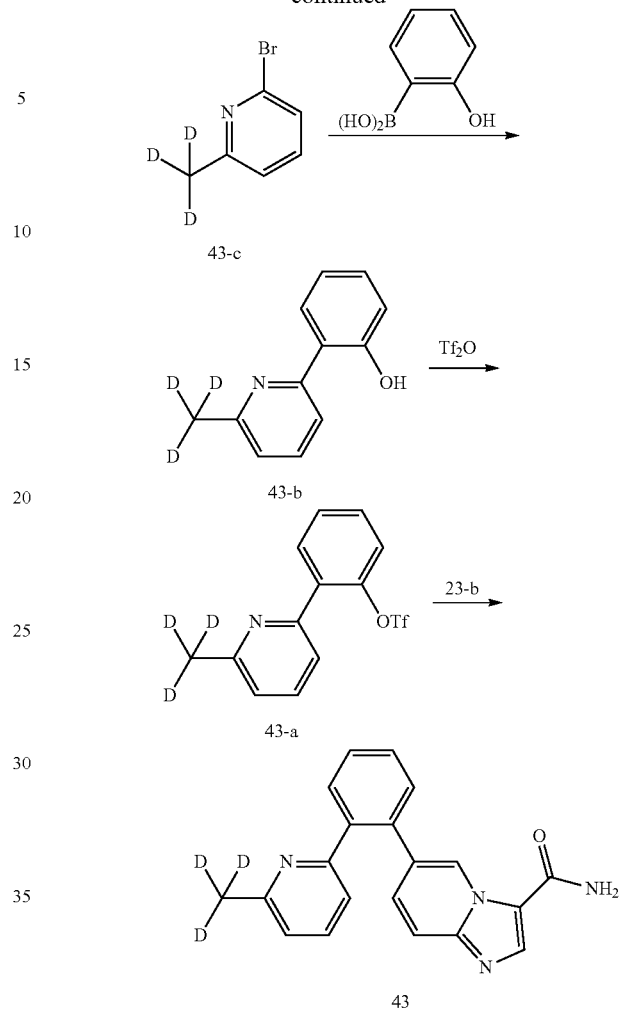

Synthesis of Compound 43-c 2,6-Dibromopyridine (1 g, 4.22 mmol) was dissolved in tetrahydrofuran (10 mL) and the solution was cooled to −78° C., followed by slow addition of n-butyl lithium (2.5 M, 2.03 mL, 5.07 mmol). The reaction solution was stirred at low temperature for half an hour, followed by addition of deuterated iodomethane (0.32 mL, 5.07 mmol). The reaction solution was warmed to room temperature and stirred for one hour. After the reaction was quenched with water (10 mL), the mixture was extracted with ethyl acetate (10 mL×3). The organic phase was combined, dried over anhydrous sodium sulfate, filtered and evaporated to give compound 43-c (0.5 g, 67%) as a brown liquid. LC-MS (ESI): m/z=175.1 [M+H]$^+$.

Synthesis of Compound 43-b

Compound 43-b (150 mg, 70%) was obtained by using 2-hydroxyphenylboronic acid and compound 43-c as raw material according to the method for preparing compound 1-e. LC-MS (ESI): m/z=189.2 [M+H]$^+$.

Synthesis of Compound 43-a

Compound 43-a (200 mg, 78%) was obtained by using compound 43-b as raw material according to the method for preparing compound 1-c. LC-MS (ESI): m/z=321.1 [M+H]$^+$.

Synthesis of Compound 43

Compound 43 (25 mg, 16%) was obtained as a white solid by using compound 43-a and compound 23-b as raw material according to the method for preparing compound 11. LC-MS (ESI): m/z=332.2 [M+H]+. 1H NMR (400 MHz, CD3OD): δ 9.44-9.45 (m, 1H), 8.26 (s, 1H), 7.57-7.65 (m, 5H), 7.49 (dd, J1=9.2 Hz, J2=0.8 Hz, 1H), 7.14-7.19 (m, 2H), 7.06 (dd, J1=7.6 Hz, J2=0.8 Hz, 1H).

Synthetic Route of Compound 44

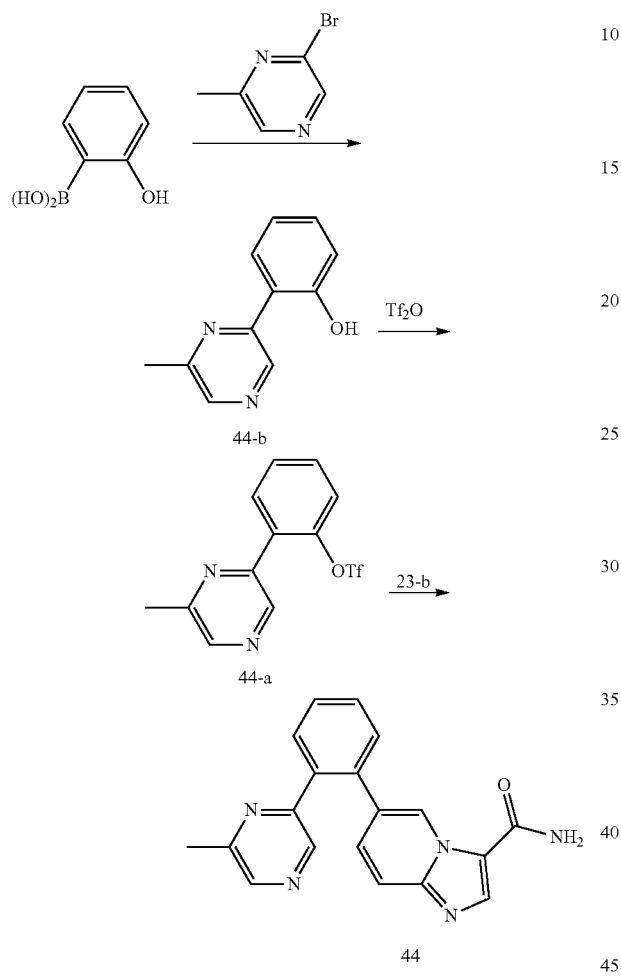

Synthetic Route of Compound 45

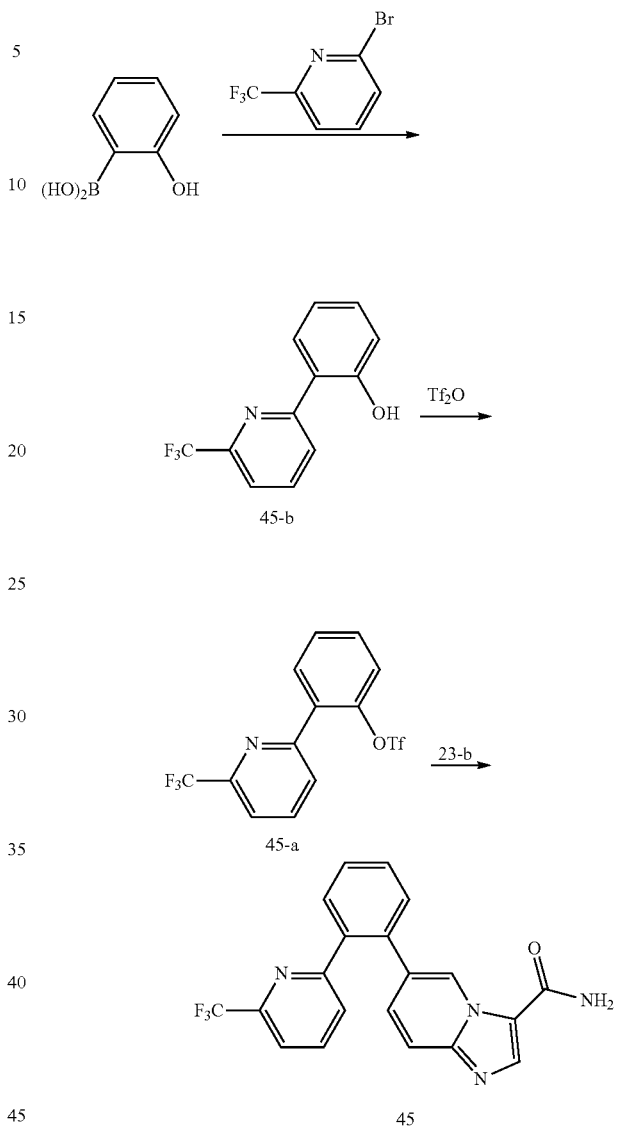

Synthesis of Compound 44-b

Compound 44-b (105 mg, 97%) was obtained by using 2-hydroxyphenylboronic acid and 2-bromo-6-methylpyrazine as raw material according to the method for preparing compound 1-e. LC-MS (ESI): m/z=187.2 [M+H]+.

Synthesis of Compound 44-a

Compound 44-a (163 mg, 90%) was obtained by using compound 44-b as raw material according to the method for preparing compound 1-c. LC-MS (ESI): m/z=319.1 [M+H]+.

Synthesis of Compound 44

Compound 44 (100 mg, 59%) was obtained as a yellow solid by using compound 44-a and compound 23-b as raw material according to the method for preparing compound 11. LC-MS (ESI): m/z=330.2 [M+H]+. 1H NMR (400 MHz, CD3OD): δ 9.40 (s, 1H), 8.35 (s, 1H), 8.28 (s, 1H), 8.20 (s, 1H), 7.74 (m, 1H), 7.68-7.61 (m, 3H), 7.57 (d, J=9.2 Hz, 1H), 7.26 (dd, J=9.2, 1.7 Hz, 1H), 2.51 (s, 3H).

Synthesis of Compound 45-b

Compound 45-b (50 mg, 23%) was obtained by using 2-hydroxyphenylboronic acid and 2-bromo-6-trifluoromethylpyridine as raw material according to the method for preparing compound 1-e. LC-MS (ESI): m/z=240.1 [M+H]+.

Synthesis of Compound 45-a

Compound 45-a (65 mg, 84%) was obtained by using compound 45-b as raw material according to the method for preparing compound 1-c. LC-MS (ESI): m/z=370.0 [M+H]+.

Synthesis of Compound 45

Compound 45 (10 mg, 14%) was obtained as a white solid by using compound 45-a and compound 23-b as raw material according to the method for preparing compound 11. LC-MS (ESI): m/z=382.9 [M+H]+. 1H NMR (400 MHz, CD3OD): δ 9.39 (s, 1H), 8.27 (s, 1H), 7.92 (t, J=7.9 Hz, 1H), 7.81-7.73 (m, 1H), 7.65-7.61 (m, 5H), 7.51 (d, J=9.2 Hz, 1H), 7.18 (dd, J=9.2, 1.8 Hz, 1H).

Synthetic Route of Compound 46

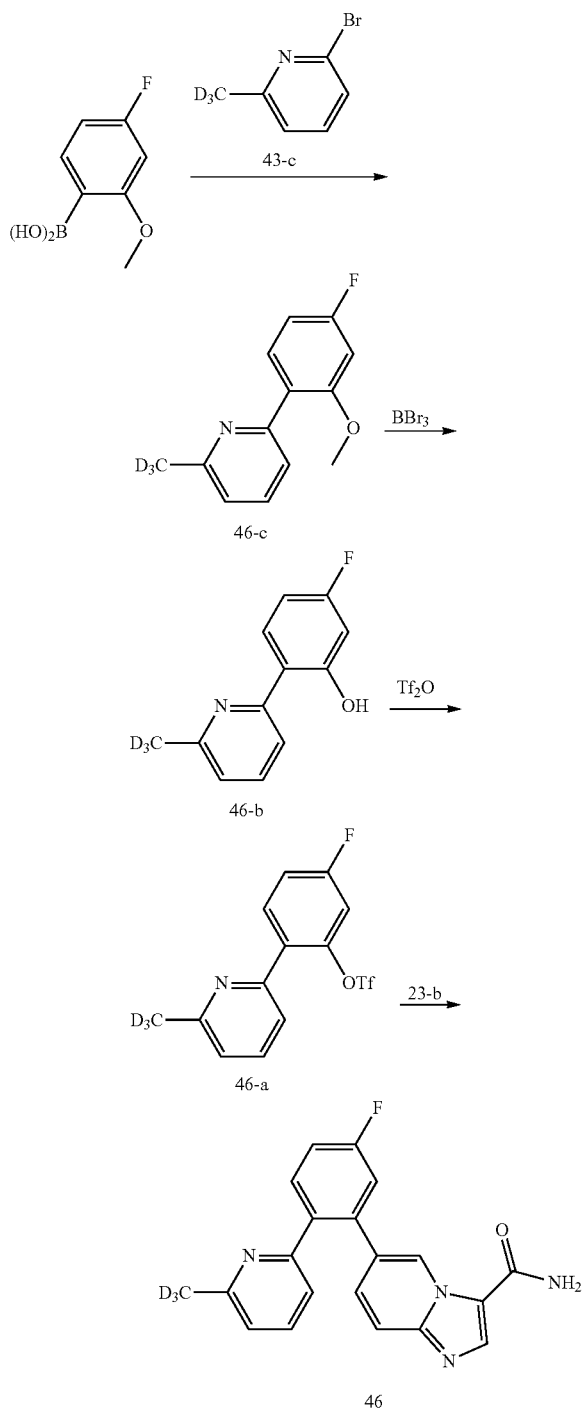

46

Synthesis of Compound 46-c

Compound 46-c (342 mg, 91%) was obtained by using 4-fluoro-2-methoxyphenylboronic acid and compound 43-c as raw material according to the method for preparing compound 1-e. LC-MS (ESI): m/z=221.1 [M+H]$^+$.

Synthesis of Compound 46-b

Compound 46-b (274 mg, 86%) was obtained by using compound 46-c as raw material according to the method for preparing compound 1-d. LC-MS (ESI): m/z=207.2 [M+H]$^+$.

Synthesis of Compound 46-a

Compound 46-a (306 mg, 68%) was obtained by using compound 46-b as raw material according to the method for preparing compound 1-c. LC-MS (ESI): m/z=339.0 [M+H]$^+$.

Synthesis of Compound 46

Compound 46 (90 mg, 51%) was obtained as a white solid by using compound 46-a and compound 23-b as raw material according to the method for preparing compound 11. LC-MS (ESI): m/z=350.0 [M+H]$^+$. $^1$H NMR (500 MHz, CD$_3$OD): δ 9.45 (s, 1H), 8.27 (s, 1H), 7.66 (dd, J=8.5, 5.8 Hz, 1H), 7.57 (t, J=7.7 Hz, 1H), 7.54-7.49 (m, 1H), 7.40 (dd, J=9.5, 2.6 Hz, 1H), 7.36-7.32 (m, 1H), 7.22-7.14 (dd, J=8, 5 Hz, 2H), 7.05 (m, 1H).

Synthetic Route of Compound 47

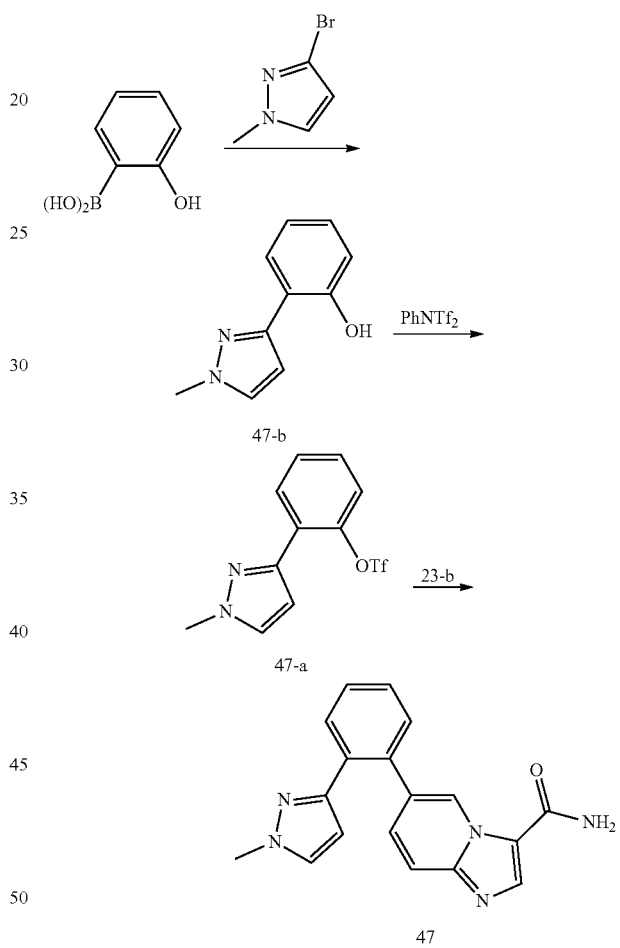

47

Synthesis of Compound 47-b

Compound 47-b (200 mg, 90%) was obtained by using 2-hydroxyphenylboronic acid and 3-bromo-1-methylpyrrole as raw material according to the method for preparing compound 1-e. LC-MS (ESI): m/z=175.2 [M+H]$^+$.

Synthesis of Compound 47-a

Potassium carbonate (238 mg, 1.72 mmol) and N-phenylbis(trifluoromethanesulfonyl)imide (225.6 mg, 0.63 mmol) were added to a solution of compound 47-b (100 mg, 0.57 mmol) in DMF (5 mL). The mixture was stirred at room temperature overnight. Water (10 mL) and ethyl acetate (10 mL) were added to the reaction solution, then the organic layer was separated and the aqueous layer was extracted with ethyl acetate (10 mL×2). The organic phase was combined, washed with water and saturated brine, dried over anhydrous sodium sulfate and evaporated under reduced pressure. The residue was purified by silica gel column chromatography (eluent: PE/EA=5/1) to give compound 47-a (100 mg, 52%). LC-MS (ESI): m/z=307.1 [M+H]$^+$.

Synthesis of Compound 47

Compound 47 (40 mg, 39%) was obtained as a yellow solid by using compound 47-a and compound 23-b as raw material according to the method for preparing compound 11 LC-MS (ESI): m/z=318.3 [M+H]$^+$. $^1$H NMR (500 MHz, CD$_3$OD): δ 9.49 (s, 1H), 8.29 (s, 1H), 7.67-7.70 (m 1H), 7.50-7.67 (m, 4H), 7.44 (d, J=2 Hz, 1H), 7.28 (dd, J$_1$=9 Hz, J$_2$=1.5 Hz, 1H), 5.87 (d, J=2.5 Hz, 1H), 3.86 (s, 3H).

Synthetic Route of Compound 48

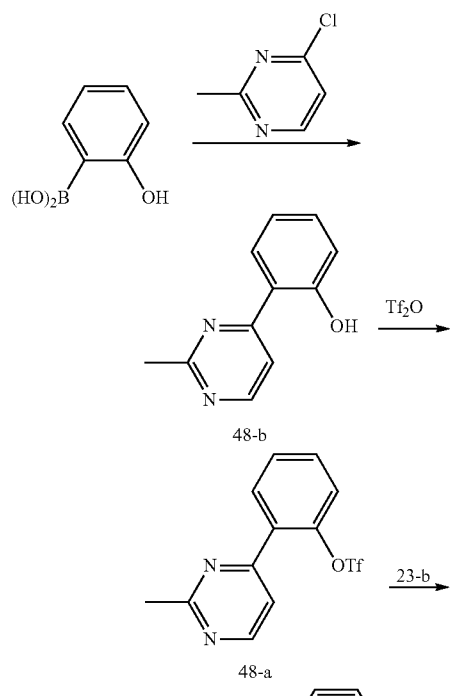

Synthesis of Compound 48-b

Compound 48-b (80 mg, 28%) was obtained by using 2-hydroxyphenylboronic acid and 4-chloro-2-methylpyridine as raw material according to the method for preparing compound 1-e. LC-MS (ESI): m/z=187.1 [M+H]$^+$.

Synthesis of Compound 48-a

Compound 48-a (85 mg, 62%) was obtained by using compound 48-b as raw material according to the method for preparing compound 1-c. LC-MS (ESI): m/z=319.0 [M+H]$^+$.

Synthesis of Compound 48

Compound 48 (40 mg, 45%) was obtained as a yellow solid by using compound 48-a and compound 23-b as raw material according to the method for preparing compound 11. LC-MS (ESI): m/z=330.1 [M+H]$^+$. $^1$H NMR (500 MHz, DMSO-d$_6$): δ 9.39 (s, 1H), 8.48 (d, J=5.2 Hz, 1H), 8.33 (s, 1H), 7.95 (m, 1H), 7.74 (m, 1H), 7.68-7.55 (m, 4H), 7.37 (m, 1H), 7.14-7.04 (m, 2H), 2.53 (s, 3H).

Synthetic Route of Compound 49

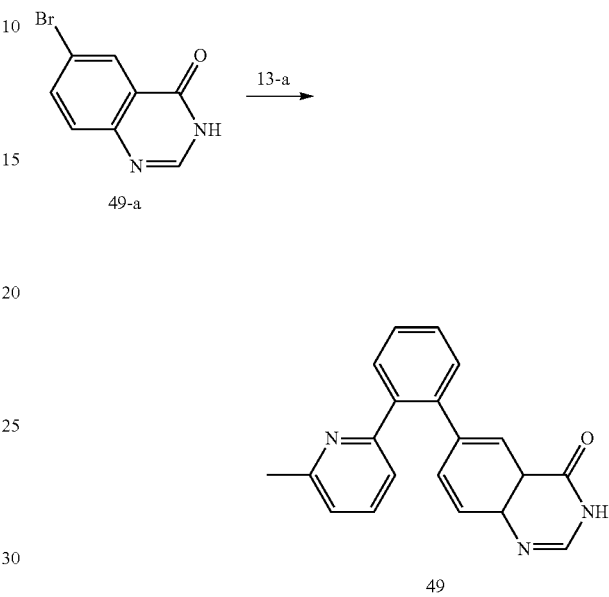

Synthesis of Compound 49

Compound 49 (16 mg, 11%) was obtained as a white solid by using compound 49-a as raw material according to the method for preparing compound 13. LC-MS (ESI): m/z=314.0 [M+H]$^+$. $^1$H NMR (500 MHz, CD$_3$OD): δ 8.08 (s, 1H), 8.06 (s, 1H), 7.66-7.49 (m, 7H), 7.15 (d, J=7.7 Hz, 1H), 6.93 (d, J=7.7 Hz, 1H), 2.47 (s, 3H).

Synthetic Route of Compound 50 and 51

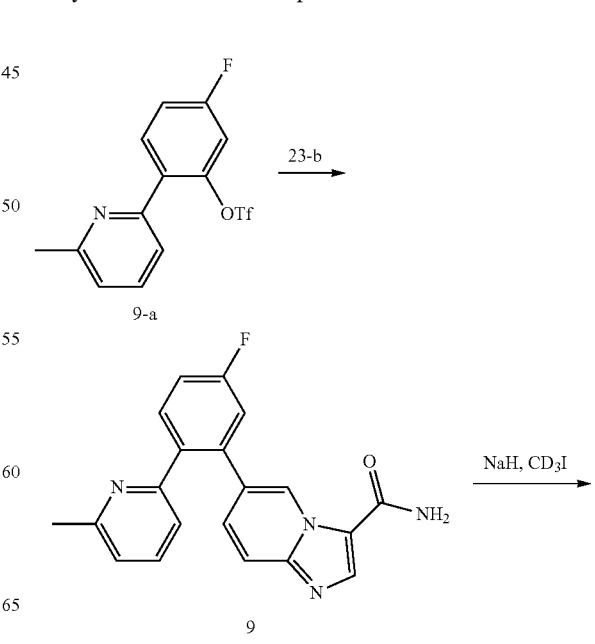

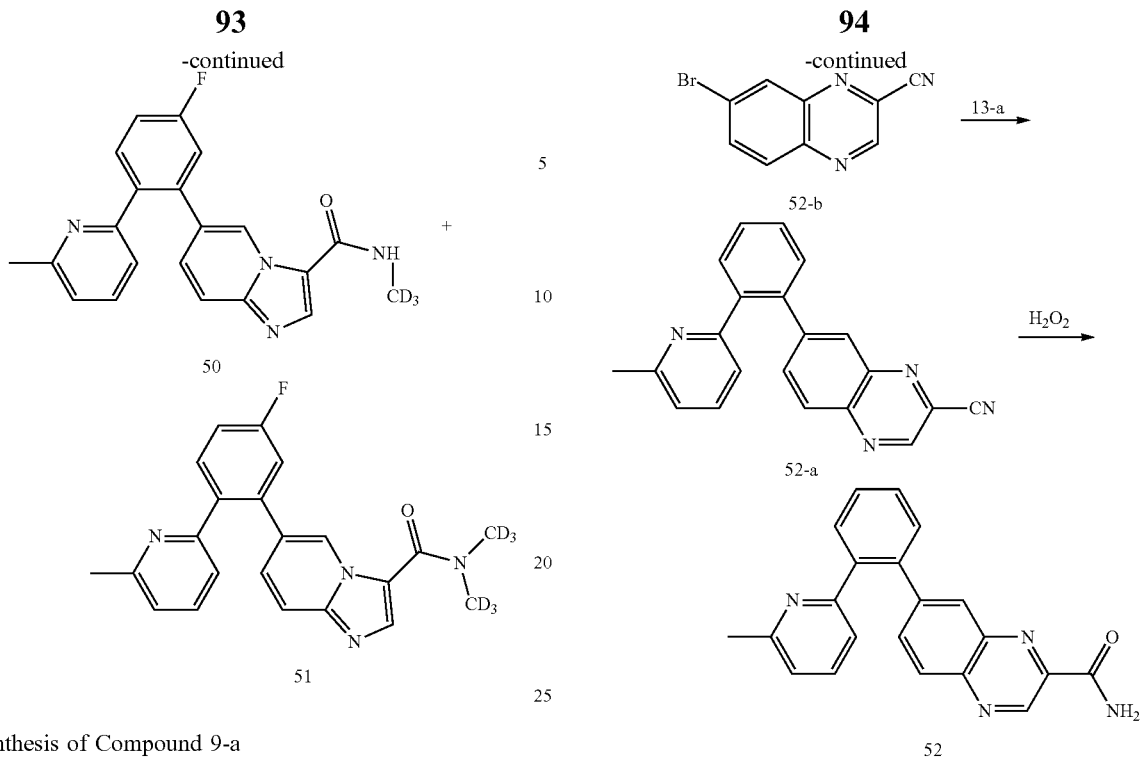

Synthesis of Compound 9-a

Compound 9-a (300 mg) was obtained by replacing raw material of 2-methoxyphenylboronic acid with 4-fluoro-2-methoxyphenylboronic acid according to the route and method for preparing compound 1-c. LC-MS (ESI): m/z=336.0 [M+H]⁺.

Synthesis of Compound 9

Compound 9 (246 mg, 71%) was obtained by using compound 9-a and compound 23-b as raw material according to the method for preparing compound 11. LC-MS (ESI): m/z=347.0 [M+H]⁺.

Synthesis of Compound 50 and 51

Compound 9 (100 mg, 0.289 mmol) was dissolved in dry tetrahydrofuran (10 mL), followed by slow addition of NaH (60% in oil, 14 mg, 0.578 mmol). The mixture was stirred at room temperature for 1 hour, then deuterated iodomethane (42 mg, 0.289 mmol) was added. The mixture was stirred for another 2 hours, then diluted with water (30 mL) and extracted with ethyl acetate (30 mL×2). The organic phase was combined, dried over anhydrous sodium sulfate, filtered and evaporated under reduced pressure. The residue was purified by preparative HPLC to give compound 50 (5 mg) and 51 (10 mg) as a white solid.

Compound 50: LC-MS (ESI): m/z=364.2 [M+H]⁺. ¹H NMR (500 MHz, CD₃OD): δ9.43 (s, 1H), 8.16 (s, 1H), 7.67 (dd, J=8.5, 5.8 Hz, 1H), 7.57 (t, J=7.8 Hz, 1H), 7.49 (d, J=9.3 Hz, 1H), 7.40 (dd, J=9.5, 2.6 Hz, 1H), 7.35 (m, 1H), 7.18-7.13 (m, 2H), 7.06 (d, J=7.8 Hz, 1H), 2.46 (s, 3H).

Compound 51: LC-MS (ESI): m/z=381.0 [M+H]⁺. ¹H NMR (500 MHz, CD₃OD): δ8.98 (s, 1H), 8.04 (s, 1H), 7.66 (dd, J=8.5, 5.8 Hz, 1H), 7.56 (t, J=7.7 Hz, 1H), 7.47 (d, J=9.3 Hz, 1H), 7.40 (dd, J=9.5, 2.6 Hz, 1H), 7.34 (m, 1H), 7.17 (d, J=7.7 Hz, 1H), 7.10 (dd, J=9.3, 1.7 Hz, 1H), 7.05 (d, J=7.7 Hz, 1H), 2.48 (s, 3H).

Synthetic Route of Compound 52

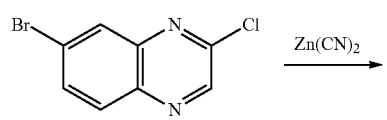

Synthesis of Compound 52-b

A mixture of zinc cyanide (48.2 mg, 0.41 mmol), 7-bromo-2-chloroquinoxaline (200 mg, 0.82 mmol), tetrakis(triphenylphosphine)palladium (94.9 mg, 0.082 mmol) and N,N-dimethyl formamide (4 mL) was stirred under nitrogen atmosphere at 100° C. overnight. The reaction solution was cooled to room temperature, diluted with ethyl acetate. The organic layer was separated, washed with water and saturated brine, dried over anhydrous sulfate, filtered and coevaporated under reduced pressure. The residue was purified by silica gel column chromatography (eluent: PE/A=5/1) to give compound 52-b as a white solid (0.1 g, 23%). LC-MS (ESI): m/z=324.0 [M+H]⁺.

Synthesis of Compound 52-a

Compound 52-a (20 mg, 32%) was obtained as a white solid by using compound 52-b as raw material according to the method for preparing compound 13. LC-MS (ESI): m/z=323.2 [M+H]⁺.

Synthesis of Compound 52

Hydrogen peroxide (0.29 mmol) was added dropwise to a solution of compound 52-a (20 mg, 0.062 mmol) and potassium carbonate (1.3 mg) in dimethyl sulfoxide (2 mL). The mixture was stirred overnight. Water (5 mL) was slowly added to the reaction solution to quench the reaction. The resulting mixture was stirred for half an hour, and a white solid precipitated. The solid was collected by filtration, and dried to give compound 52 as a white solid (15 mg, 70%). LC-MS (ESI): m/z=341.2 [M+H]⁺. ¹H NMR (400 MHz, CD₃OD): δ9.48 (s, 1H), 8.10 (d, J=1.6 Hz, 1H), 7.97 (d, J=8.8 Hz, 1H), 7.60-7.70 (m, 5H), 7.50 (t, J=7.6 Hz, 1H), 7.13 (d, J=7.6 Hz, 1H), 7.01 (d, J=7.6 Hz, 1H), 2.42 (s, 3H).

Synthetic Route of Compound 53

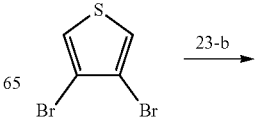

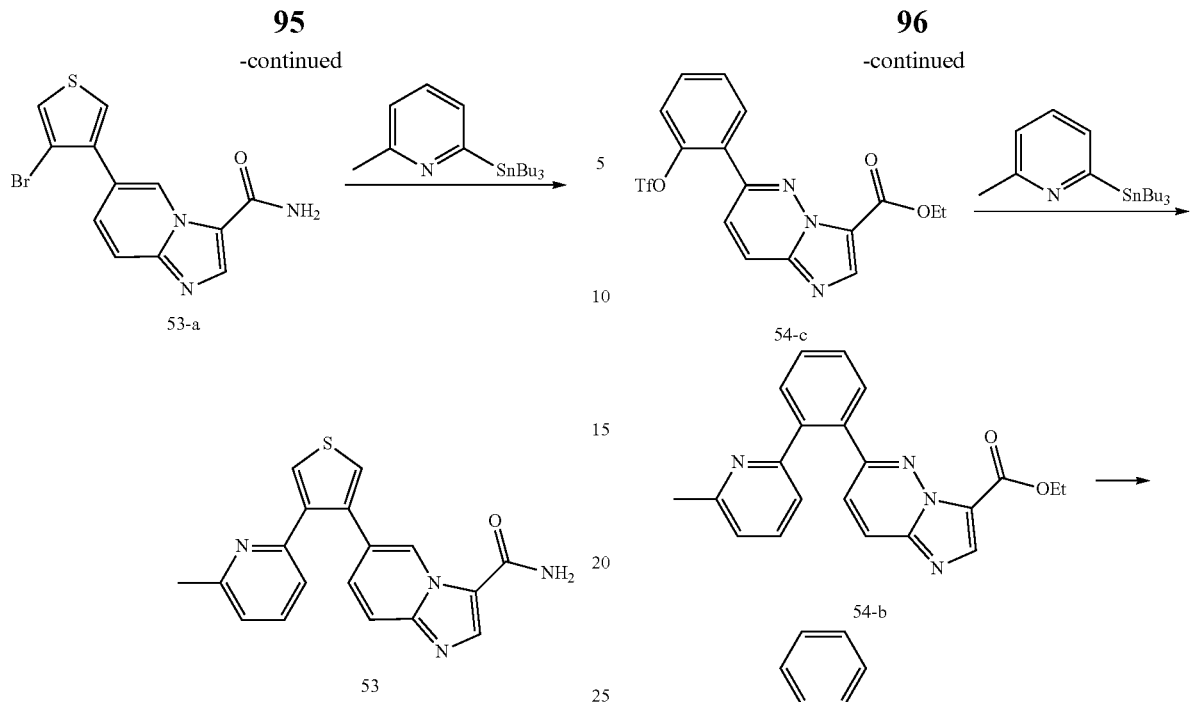

Synthesis of Compound 53-a

Compound 53-a (360 mg, 56%) was obtained by using 2,3-dibromothiophene and compound 23-b as raw material according to the method for preparing compound 11. LC-MS (ESI): m/z=322.0 [M+H]$^+$.

Synthesis of Compound 53

Compound 53 (36 mg, 11%) was obtained by using compound 53-a as raw material according to the method for preparing compound 25-c. LC-MS (ESI): m/z=335.0 [M+H]$^+$. $^1$H NMR (400 MHz, CD$_3$OD): δ9.49 (s, 1H), 8.27 (s, 1H), 7.81 (d, J=2.8 Hz, 1H), 7.70 (d, J=2.8 Hz, 1H), 7.64 (t, J=6.0 Hz, 1H), 7.55 (d, J=8.0 Hz, 1H), 7.26 (d, J=8.0 Hz, 1H), 7.18 (d, J=6.0 Hz, 1H), 7.14 (d, J=6.0 Hz, 1H), 2.43 (s, 3H).

Synthetic Route of Compound 54

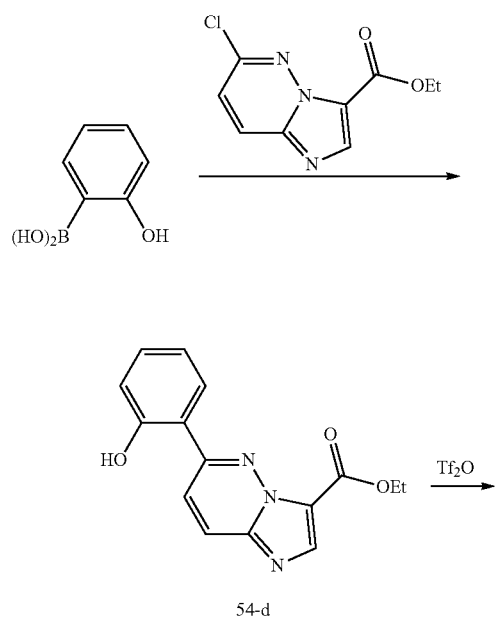

Synthesis of Compound 54-d

Compound 54-d (690 mg, 48.6%) was obtained by using 2-hydroxyphenylboronic acid and ethyl 6-chloroimidazo[1,2-b]pyridazine-3-carboxylate as raw material according to the method for preparing compound 1-e. LC-MS (ESI): m/z=284.0 [M+H]$^+$.

Synthesis of Compound 54-c

Compound 54-c (660 mg, 79%) was obtained by using compound 54-d as raw material according to the method for preparing compound 1-c. LC-MS (ESI): m/z=416 [M+H]$^+$.

Synthesis of Compound 54-a and 54-b

A mixture of compound 54-c (0.415 g, 1.0 mmol), 2-methyl-6-tributylstannylpyridine (0.59 g, 1.5 mmol), PdCl$_2$(PPh$_3$)$_2$ (0.21 g, 0.3 mmol), lithium chloride (0.42 g, 10 mmol) and DMF (20 mL) was stirred under nitrogen atmosphere at 110° C. overnight. The reaction solution was cooled to room temperature and evaporated under reduced pressure. Aqueous sodium hydroxide (2 M, 40 mL) was added to the residue of compound 54-b, and the resulting mixture was stirred at room temperature overnight. The mixture was extracted with ethyl acetate (30 mL×3) and the organic layer was discarded. The aqueous layer was cooled to 0° C. and neutralized pH of 5-6 with hydrochloric acid (6 M), then extracted with ethyl acetate (50 mL×3). The organic phase was washed with saturated brine, dried over anhydrous sodium sulfate and evaporated under reduced pressure to give compound 54-a as a white solid (120 mg, 36.3% for two steps). LC-MS (ESI): m/z=331 [M+H]⁺.

Synthesis of Compound 54

Compound 54 (60 mg, 50%) was obtained by using compound 54-a as raw material according to the method for preparing compound 2. LC-MS (ESI): m/z=330.0 [M+H]⁺. ¹H NMR (400 MHz, CD₃OD): δ8.32 (s, 1H), 8.13 (d, J=8.0 Hz, 1H), 7.88 (s, 1H), 7.72 (m, 4H), 7.45 (d, J=8.0 Hz, 1H), 7.26 (d, J=7.0 Hz, 1H), 7.18 (d, J=7.0 Hz, 1H), 2.30 (s, 3H).

Synthetic Route of Compound 55

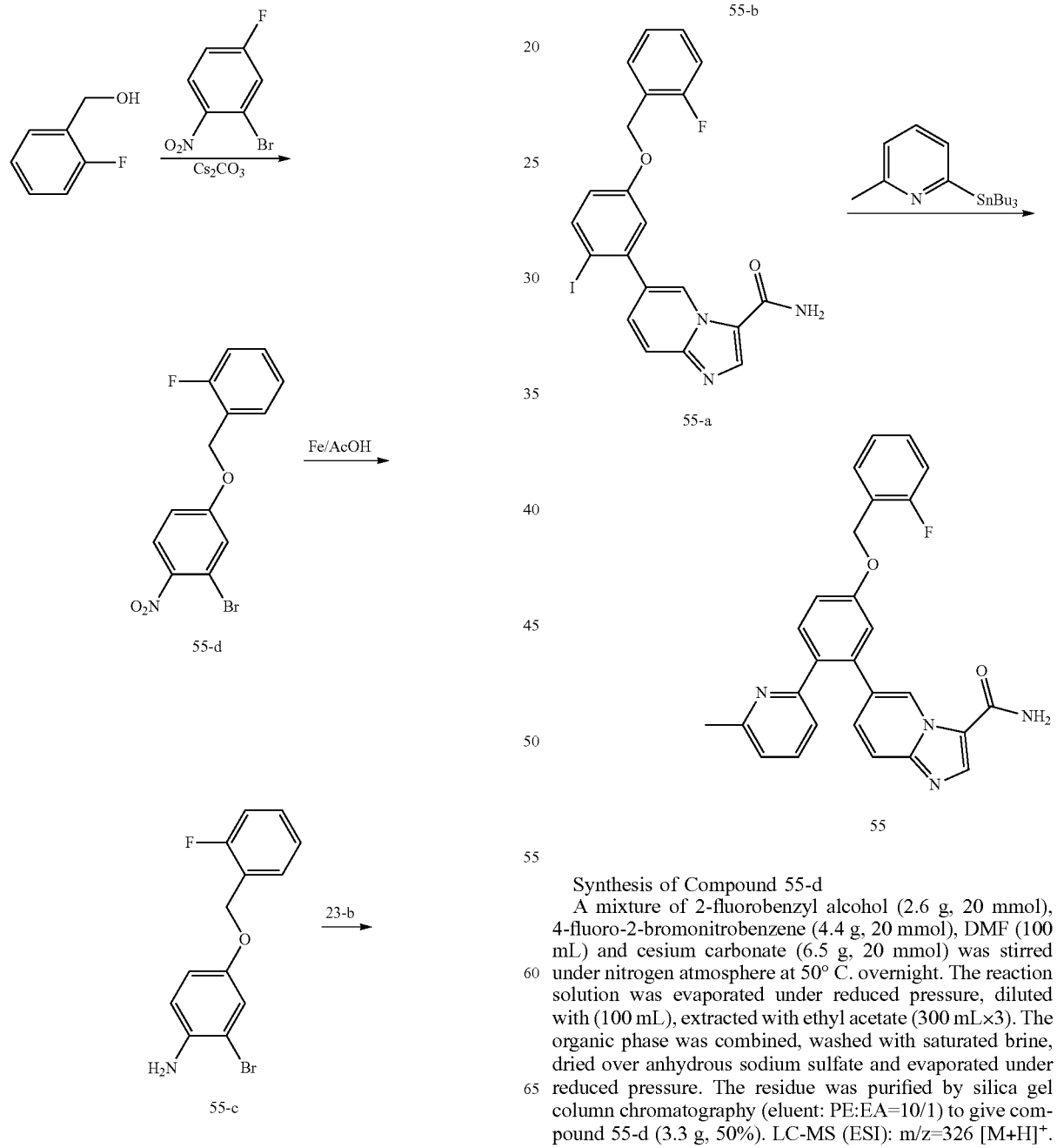

Synthesis of Compound 55-d

A mixture of 2-fluorobenzyl alcohol (2.6 g, 20 mmol), 4-fluoro-2-bromonitrobenzene (4.4 g, 20 mmol), DMF (100 mL) and cesium carbonate (6.5 g, 20 mmol) was stirred under nitrogen atmosphere at 50° C. overnight. The reaction solution was evaporated under reduced pressure, diluted with (100 mL), extracted with ethyl acetate (300 mL×3). The organic phase was combined, washed with saturated brine, dried over anhydrous sodium sulfate and evaporated under reduced pressure. The residue was purified by silica gel column chromatography (eluent: PE:EA=10/1) to give compound 55-d (3.3 g, 50%). LC-MS (ESI): m/z=326 [M+H]⁺.

Synthesis of Compound 55-c

A mixture of compound 55-d (0.65 g, 2.0 mmol), iron powder (1.12 g, 20 mmol), ethanol (100 mL) and acetic acid (20 mL) was stirred under nitrogen atmosphere at room temperature overnight. The reaction solution was evaporated under reduced pressure, diluted with saturated aqueous sodium bicarbonate solution (100 mL) and extracted with ethyl acetate (300 mL×3). The organic phase was combined, washed with saturated brine, dried over anhydrous sodium sulfate and evaporated under reduced pressure to give compound 55-c (0.46 g, 77.2%). LC-MS (ESI): m/z=298 [M+H]$^+$.

Synthesis of Compound 55-b

Compound 55-b (210 mg, 55.8%) was obtained by using compound 55-c and compound 23-b as raw material according to the method for preparing compound 11. LC-MS (ESI): m/z=377 [M+H]$^+$.

Synthesis of Compound 55-a

Compound 55-b (0.19 g, 0.5 mmol) was dissolved in dilute hydrochloric acid (4 N, 6 mL), and a solution of sodium nitrite (0.07 g, 1.0 mmol) in water (2 mL) was slowly added dropwise. The reaction solution was stirred at room temperature for 0.5 hour. Potassium iodide (0.117 g, 1.0 mmol) was added to the reaction solution and the reaction solution was stirred for another 1 hour. The reaction solution was evaporated under reduced pressure, diluted with sodium carbonate (20 mL), extracted with ethyl acetate (50 mL×3). The organic phase was combined, washed with saturated brine, dried over anhydrous sodium sulfate and evaporated under reduced pressure. The residue was purified by silica gel column chromatography to give compound 55-a as a white solid (220 mg, 90%). LC-MS (ESI): m/z=488 [M+H]$^+$.

Synthesis of Compound 55

Compound 55 (86 mg, 19%) was obtained by using compound 55-a as raw material according to the method for preparing compound 25-c. LC-MS (ESI): m/z=453 [M+H]$^+$. $^1$H NMR (400 MHz, CD$_3$OD): δ9.44 (s, 1H), 8.39 (s, 1H), 8.15 (t, J=6.4 Hz, 1H), 7.74 (d, J=6.8 Hz, 2H), 7.70 (d, J=6.8 Hz, 1H), 7.60 (m, 2H), 7.44 (m, 4H), 7.25 (t, J=3.2 Hz, 1H), 7.20 (t, J=3.2 Hz, 1H), 5.37 (s, 2H), 2.76 (s, 3H).

Synthetic Route of Compound 56

Synthesis of Compound 56

Compound 2 (94.8 mg, 0.289 mmol) was dissolved in dry tetrahydrofuran (10 mL), NaH (60% in oil, 7 mg, 0.289 mmol) was slowly added, and the mixture was stirred at room temperature for 1 hour, followed by slow addition of deuterated iodomethane (42 mg, 0.289 mmol). The mixture was stirred for another 2 hrs, then diluted with water (30 mL) and extracted with ethyl acetate (30 mL×2). The organic phase was combined, dried over anhydrous sodium sulfate, filtered and evaporated under reduced pressure. The residue was purified by preparative HPLC to give compound 56 (20 mg) as a white solid. LC-MS (ESI): m/z=346.0 [M+H]$^+$. $^1$H NMR (500 MHz, DMSO-d$_6$): δ 9.41 (s, 1H), 8.40 (s, 1H), 8.25 (s, 1H), 7.68-7.63 (m, 1H), 7.59-7.47 (m, 5H), 7.09 (d, J=7.6 Hz, 1H), 6.96 (dd, J=9.2, 1.8 Hz, 2H), 2.37 (s, 3H).

Synthetic Route of Compound 57

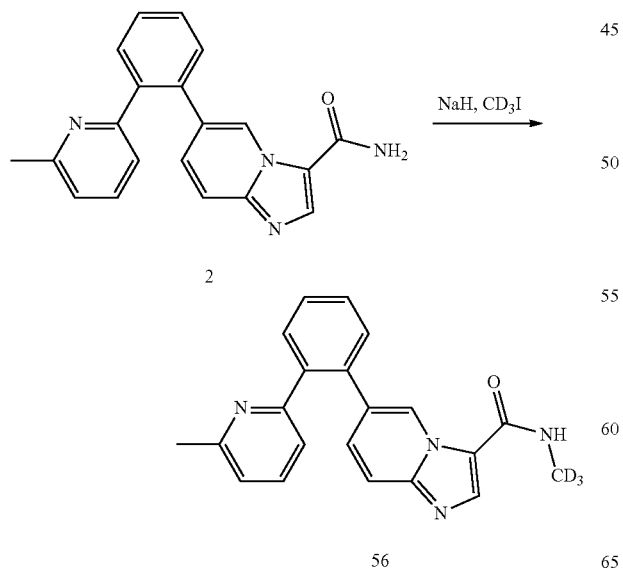

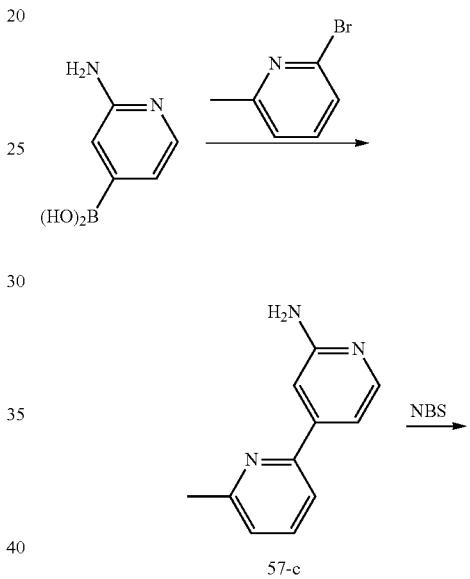

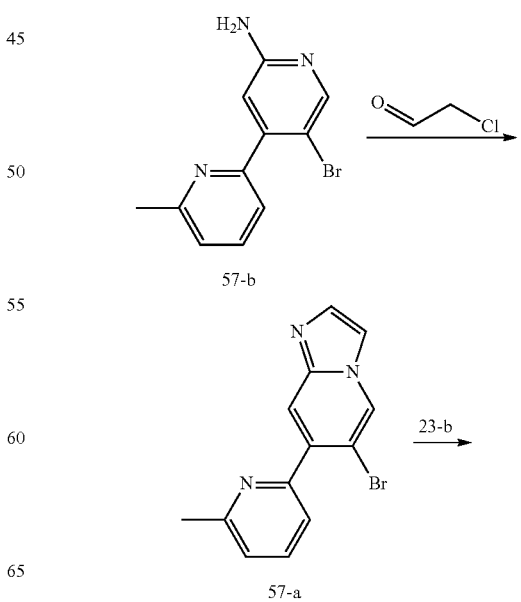

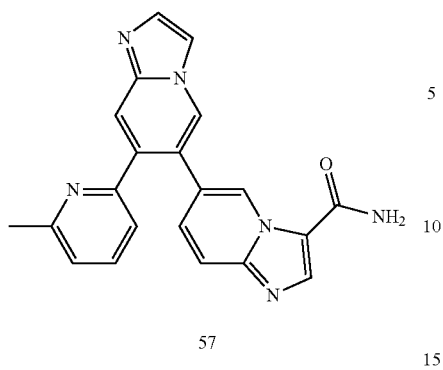

57

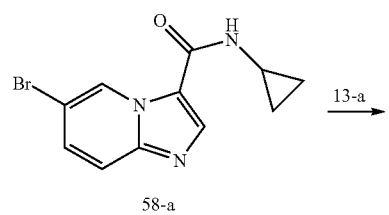

58-a

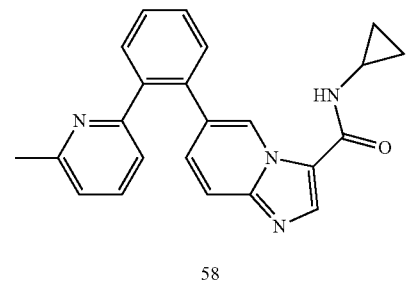

58

Synthesis of Compound 57-c

Compound 57-c (100 mg, 75%) was obtained by using 2-aminopyridine-4-boronic acid and 2-bromo-6-methylpyridine as raw material according to the method for preparing compound 1-e. LC-MS (ESI): m/z=186.1 [M+H]+.

Synthesis of Compound 57-b

Compound 57-c (100 mg, 0.54 mmol) was dissolved in dry acetonitrile (10 mL), followed by addition of N-bromosuccinimide (96.1 mg, 0.54 mmol). The reaction solution was stirred at room temperature for 2 hours, then evaporated under reduced pressure. The residue was purified by silica gel column chromatography (eluent: PE/EA=1/1) to give compound 57-b (90 mg, 63%). LC-MS (ESI): m/z=264.0 [M+H]+. $^1$H NMR (500 MHz, CDCl$_3$): δ 8.25 (s, 1H), 7.67 (t, J=8 Hz, 1H), 7.42 (d, J=8 Hz, 1H), 7.20 (d, J=7.5 Hz, 1H), 6.72 (s, 1H), 4.51 (bs, 1H), 2.63 (s, 3H).

Synthesis of Compound 57-a

Compound 57-b (90 mg, 0.34 mmol) was dissolved in ethanol (10 mL), followed by slow addition of aqueous chloroacetaldehyde solution (6.1 M, 80 μL, 0.51 mmol). The reaction solution was heated to reflux and stirred overnight. The reaction was evaporated under reduced pressure. The residue was purified by silica gel column chromatography (eluent: PE/EA=1/1) to give compound 57-b (90 mg, 91%). LC-MS (ESI): m/z=287.9 [M+H]+.

Synthesis of Compound 57

Compound 57 (30 mg, 26%) was obtained as a white solid by using compound 57-a and compound 23-b as raw material according to the method for preparing compound 11. (ESI): m/z=369.0 [M+H]+. $^1$H NMR (500 MHz, CD$_3$OD): δ9.58 (s, 1H), 8.30 (s, 1H), 8.03 (s, 1H), 7.83 (s, 1H), 7.75 (d, J=1 Hz, 1H), 7.65 (t, J=7.5 Hz, 1H), 7.05 (d, J=9 Hz, 1H), 7.22 (t, J=6.5 Hz, 1H), 7.15 (dd, J$_1$=8.5 Hz, J$_2$=1.5 Hz, 1H), 2.43 (s, 3H).

Synthetic Route of Compound 58

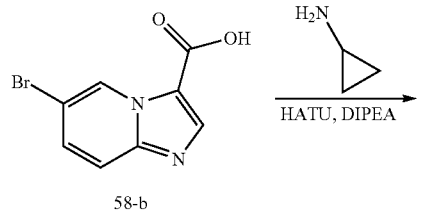

58-b

Synthesis of Compound 58-a

A mixture of commercially available compound 58-b (200 mg, 0.83 mmol), cyclopropylamine (71 mg, 0.086 mL, 1.24 mmol), HATU (631 mg, 1.66 mmol), DIPEA (536 mg, 0.723 mL, 4.15 mmol) and dichloromethane (15 mL) was stirred at room temperature overnight. The reaction solution was diluted with water (20 mL) and extracted with dichloromethane (30 mL). The organic phase was dried over anhydrous sodium sulfate, filtered and evaporated under reduced pressure. The residue was purified by silica gel column chromatography (eluent: dichloromethane/methanol=20/1) to give compound 58-a (187 mg, 80.6%). LC-MS (ESI): m/z=280.0 [M+H]+.

Synthesis of Compound 58

Compound 58 (20 mg, 18%) was obtained by using compound 58-a as raw material according to the method for preparing compound 13. LC-MS (ESI): m/z=369.0 [M+H]+. $^1$H NMR (500 MHz, CDCl$_3$): δ9.64 (s, 1H), 7.96 (s, 1H), 7.69 (d, J=7.1 Hz, 1H), 7.54-7.49 (m, 2H), 7.49-7.43 (m, 1H), 7.38-7.33 (m, 2H), 7.00 (d, J=7.7 Hz, 1H), 6.91 (d, J=9.2 Hz, 1H), 6.86 (d, J=7.7 Hz, 1H), 6.16 (s, 1H), 2.89 (m, 1H), 2.53 (s, 3H), 0.91 (m, 2H), 0.68 (m, 2H).

Synthetic Route of Compound 59

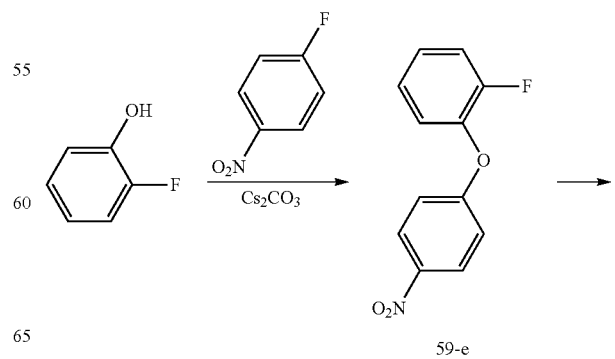

59-e

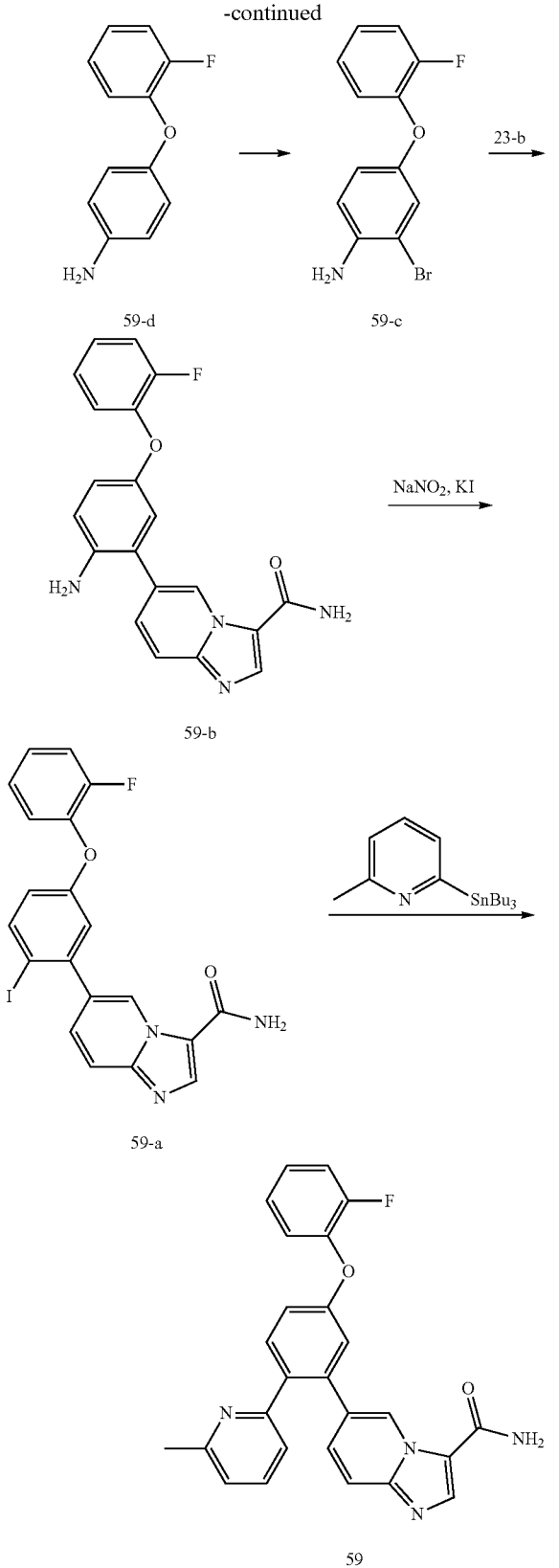

59-d
59-c
59-b
59-a
59

Synthesis of Compound 59-e

Compound 59-e (6.3 g, 67.6%) was obtained by using 2-fluorophenol and 4-fluoronitrobenzene as raw material according to the method for preparing compound 55-d. LC-MS (ESI): m/z=234 [M+H]+.

Synthesis of Compound 59-d

Compound 59-d (3.7 g, 91%) was obtained by using compound 59-e as raw material according to the method for preparing compound 55-c. LC-MS (ESI): m/z=204 [M+H]+.

Synthesis of Compound 59-c

A mixture of compound 59-d (2.8 g, 10 mmol), TBABr$_3$ (5.3 g, 11 mmol) and acetonitrile (50 mL) was stirred at 50° C. overnight, then evaporated under reduced pressure. The residue was purified by silica gel column chromatography (eluent: PE/EA=5/1) to give compound 59-c (2.0 g, 70.7%). LC-MS (ESI): m/z=284.0 [M+H]+.

Synthesis of Compound 59-b

Compound 59-b (960 mg, 53%) was obtained by using compound 59-c and compound 23-b as raw material according to the method for preparing compound 11. LC-MS (ESI): m/z=363 [M+H]+.

Synthesis of Compound 59-a

Compound 59-a (900 mg, 95%) was obtained by using compound 59-b as raw material according to the method for preparing compound 55-a. LC-MS (ESI): m/z=474 [M+H]+.

Synthesis of Compound 59

Compound 59 (46 mg, 23%) was obtained by using compound 59-a as raw material according to the method for preparing compound 25-c. LC-MS (ESI): m/z=439 [M+H]+. $^1$H NMR (400 MHz, CD$_3$OD): δ9.42 (s, 1H), 8.26 (s, 1H), 7.61 (d, J=7.2 Hz, 2H), 7.57 (t, J=6.0 Hz, 1H), 7.50 (d, J=7.2 Hz, 1H), 7.29 (m, 4H), 7.12 (m, 4H), 7.05 (d, J=6.4 Hz, 1H), 2.44 (s, 3H).

Synthetic Route of Compound 60

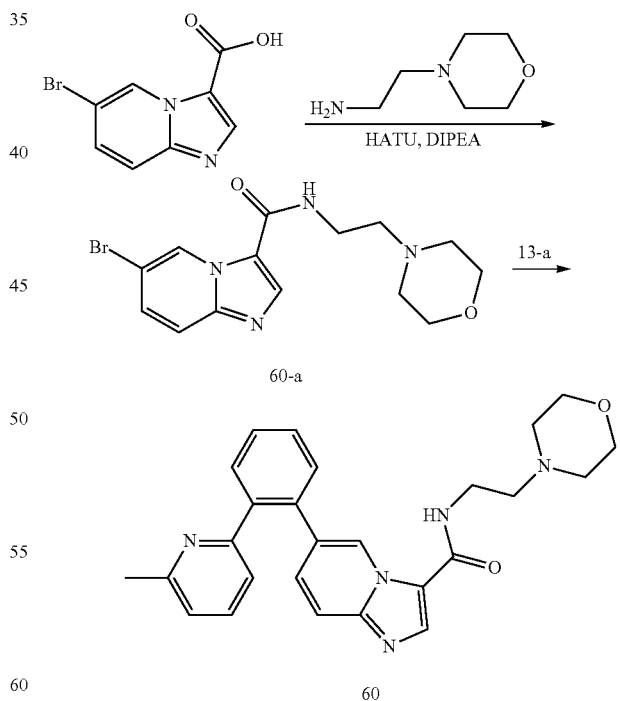

60-a
60

Synthesis of Compound 60-a

Compound 60-a (141 mg, 97%) was obtained by using N-(2-aminoethyl)morpholine as raw material according to the method for preparing compound 58-a. LC-MS (ESI): m/z=355 [M+H]+.

Synthesis of Compound 60

Compound 60 (106 mg, 60%) was obtained by using compound 60-a as raw material according to the method for preparing compound 13. LC-MS (ESI): m/z=442.0 [M+H]+. $^1$H NMR (500 MHz, DMSO-d$_6$): δ 9.39 (s, 1H), 8.44 (m, 1H), 8.28 (s, 1H), 7.66-7.64 (m, 1H), 7.59-7.46 (m, 5H), 7.09 (d, J=7.6 Hz, 1H), 7.00-6.93 (m, 2H), 3.57 (m, 4H), 3.39 (m, 2H), 2.49-2.43 (m, 6H), 2.38 (s, 3H).

Synthetic Route of Compound 61

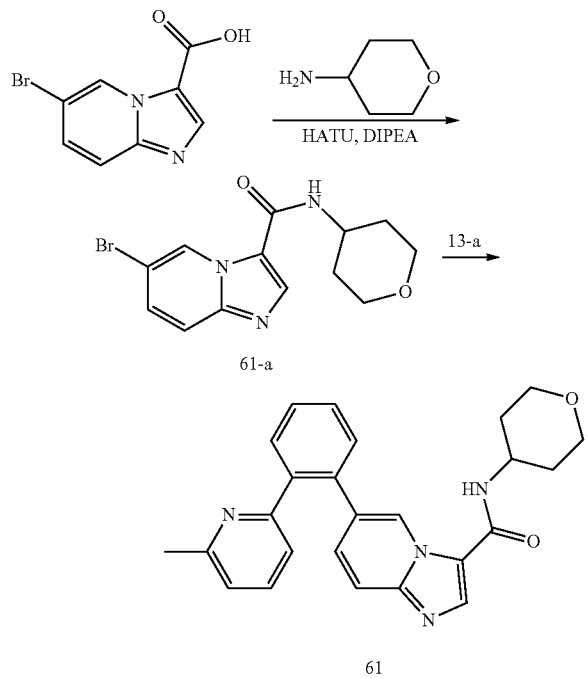

Synthesis of Compound 61-a

Compound 61-a (135 mg, 100%) was obtained by using 4-aminotetrahydropyran as raw material according to the method for preparing compound 58-a. LC-MS (ESI): m/z=325.9 [M+H]+.

Synthesis of Compound 61

Compound 61 (50 mg, 29%) was obtained by using compound 61-a as raw material according to the method for preparing compound 13. LC-MS (ESI): m/z=413.0 [M+H]+. $^1$H NMR (500 MHz, DMSO-d$_6$): δ 9.40 (s, 1H), 8.34 (s, 1H), 8.30 (d, J=7.7 Hz, 1H), 7.66-7.64 (m, 1H), 7.61-7.46 (m, 5H), 7.09 (d, J=7.6 Hz, 1H), 6.98-6.96 (m, 2H), 4.07-3.96 (m, 1H), 3.93-3.86 (m, 2H), 3.42-3.38 (m, 2H), 2.37 (s, 3H), 1.81-1.78 (m, 2H), 1.62-1.54 (m, 2H).

Synthetic Route of Compound 62

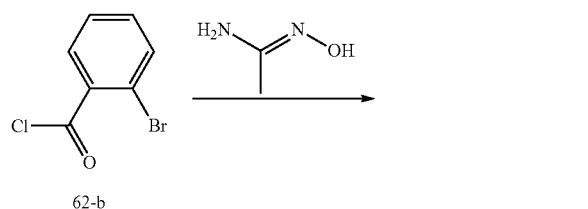

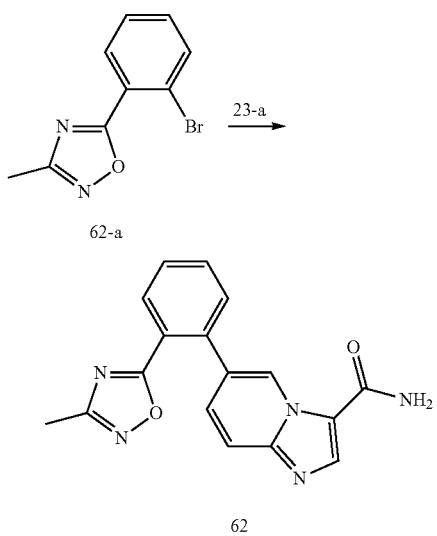

Synthesis of Compound 62-a

A mixture of commercially available compound 62-b (878 mg, 4 mmol), N-hydroxyacetimidamide (300 mg, 4 mmol) and pyridine (15 mL) was stirred at reflux overnight. The reaction solution was cooled to room temperature, evaporated under reduced pressure, diluted with water (20 mL) and extracted with dichloromethane (30 mL×2). The organic phase was combined, dried over anhydrous sodium sulfate, filtered and evaporated under reduced pressure. The residue was purified by silica gel column chromatography (eluent: PE/EA=10/1) to give compound 62-a (540 mg, 56.6%). LC-MS (ESI): m/z=239.0 [M+H]+.

Synthesis of Compound 62

Compound 62 (12 mg, 9%) was obtained by using compound 62-a and compound 23-b as raw material according to the method for preparing compound 11. LC-MS (ESI): m/z=320.0 [M+H]+. $^1$H NMR (500 MHz, CDCl$_3$) δ 9.54 (s, 1H), 8.18-8.05 (m, 2H), 7.69-7.63 (m, 2H), 7.59 (m, 1H), 7.54 (dd, J=7.6, 0.9 Hz, 1H), 7.22 (dd, J=9.2, 1.8 Hz, 1H), 5.78 (s, 2H), 2.35 (s, 3H).

Synthetic Route of Compound 63

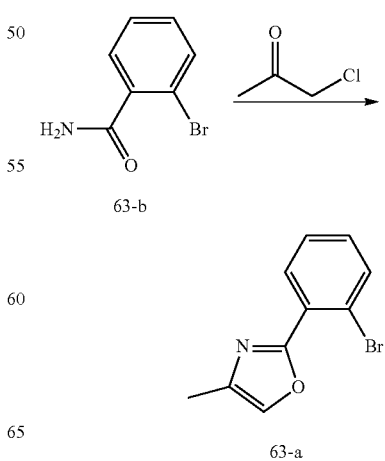

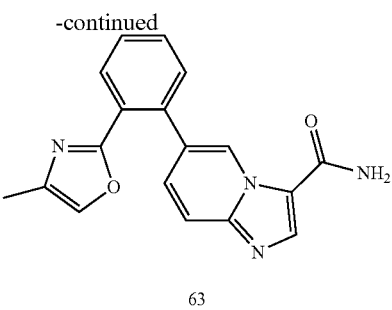

Synthesis of Compound 63-a

2-Bromobenzamide (300 mg, 1.5 mmol), chloroacetone (208 mg, 0.179 mL 2.25 mmol) and n-butanol (8 mL) were added to a 30 mL microwave tube. The microwave tube was sealed, and placed in a microwave reactor at 140° C. for 2 hours. The reaction solution evaporated under reduced pressure. The residue was purified by silica gel column chromatography (eluent: PE/EA=10/1) to give compound 63-a (200 mg, 56%). LC-MS (ESI): m/z=239.9 [M+H]$^+$.

Synthesis of Compound 63

Compound 63 (75 mg, 28%) was obtained as a white solid by using compound 63-a and compound 23-b as raw material according to the method for preparing compound 11. LC-MS (ESI): m/z=319.0 [M+H]$^+$. $^1$H NMR (400 MHz, DMSO-d$_6$) δ 9.45 (s, 1H), 8.37 (s, 1H), 7.98 (dd, J=7.5, 1.5 Hz, 2H), 7.74-7.52 (m, 5H), 7.41 (m, 1H), 7.20 (dd, J=9.3, 1.8 Hz, 1H), 2.04 (d, J=1.1 Hz, 3H).

Comparative embodiment 1: Synthetic route of comparative compound C-1

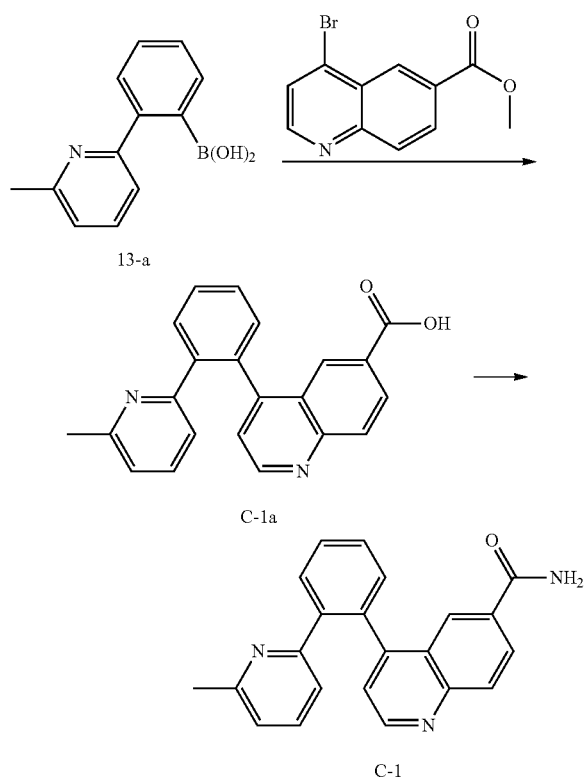

Synthesis of Compound C-1a

Compound C-1a (30 mg, 44%) was obtained by using methyl 4-bromoquinoline-6-carboxylate as raw material according to the method for preparing compound 14-a. LC-MS (ESI): m/z=341.0 [M+H]$^+$.

Synthesis of Compound C-1

Compound C-1 (5 mg, 17%) was obtained by using compound 14-a as raw material according to the method for preparing compound 14. LC-MS (ESI): m/z=340.0 [M+H]$^+$. $^1$H NMR (400 MHz, CD$_3$OD): δ8.85 (d, J=4.4 Hz, 1H), 8.03-8.14 (m, 3H), 7.77-7.80 (m, 1H), 7.67-7.75 (m, 2H), 7.56-7.58 (m, 1H), 7.45 (d, J=4.4 Hz, 1H), 7.36 (t, J=8 Hz, 1H), 6.98 (d, J=7.6 Hz, 1H), 6.92 (d, J=7.6 Hz, 1H), 2.21 (s, 3H).

Effect Embodiment 1 Evaluation of IC$_{50}$ of Inhibitory Activity Toward ALK5 Enzyme 1. Preparation of kinase buffer: 40 mM Tris (pH 7.5), 20 mM MgCl$_2$, 0.10% BSA, 1 mM DTT.

2. Preparation of the compound: the final concentration of the compound was 10 μM, and the compound was prepared to a 100-fold concentration, i.e, 1 mM. 100 μL compound of the 100-fold concentration was added to the second well of a 384-well plate, and 60 μL of 100% DMSO was added to other wells. 30 μL compound in the second well was transferred to the third well, and the compound was 3-fold diluted in sequence to give 10 different concentrations. 50 nL compound was transferred to a reaction plate by echo.

3. Kinase reaction: the kinase was added to 1× kinase buffer to prepare 2× kinase solution. The final concentration of kinase solution was 25 nM of ALK5. Peptide TGFbR1 (purchased from Signal Chem, catalog number T36-58) and ATP were added to 1× kinase buffer to prepare 2× substrate solution. The final concentration of substrate solution was 0.1 mg/mL of polypeptide TGFbR1 and 7 μM of ATP. 2.5 μL of 2× kinase solution was added to a 384-well reaction plate (containing 50 nL compound dissolved in 100% DMSO), 1× kinase buffer was added to the negative control well. The reaction plated was incubated at room temperature for 10 minutes. 2.5 μL of 2× substrate solution was added to the 384-well reaction plate. The 384-well plate was covered with a lid and incubate at 30° C. for 1 hour. ADP-Glo reagent (purchased from Promege, catalog number v9102) was equilibrated to room temperature. 5 μL of ADP-Glo reagent was transferred to the reaction well of the 384-well plate to terminate the reaction.

4. Determination of reaction results: 10 μL of kinase detection reagent was added to each reaction well, the 384-well plate was shaken for 1 minute, and allowed to stand for 30 minutes at room temperature. The luminescence value of the sample was read by Synegy.

5. Curve Fitting: the data of the luminescence reading was copied from the Synegy program. The value of the luminescence reading was converted to % inhibition by formula (% inhibition=(max−sample RLU)/(max−min)×100, wherein, "min" refers to control fluorescence reading of reaction of no enzyme; "max" refers to the fluorescence reading of the sample with DMSO added as a control. The data was imported into MS Excel and curve fitting was performed using GraphPad Prism. IC$_{50}$ values was calculated.

TABLE 1

| IC$_{50}$ of the activity of the compound toward ALK5 | | | |
|---|---|---|---|
| Compound | ALK5 IC$_{50}$ (nM) | Compound | ALK5 IC$_{50}$ (nM) |
| SB431542 | 108 | C-1 | >10000 |
| 1 | 192 | 2 | 16.5 |

TABLE 1-continued

| Compound | ALK5 IC$_{50}$ (nM) | Compound | ALK5 IC$_{50}$ (nM) |
|---|---|---|---|
| 3 | 27 | 4 | 5703 |
| 5 | 243 | 6 | 82 |
| 7 | 85 | 8 | 45 |
| 9 | 16 | 10 | 35 |
| 11 | 145 | 12 | 45 |
| 13 | 337 | 14 | 53 |
| 15 | 360 | 16 | 1300 |
| 17 | >10000 | 18 | 4738 |
| 19 | >10000 | 20 | 535 |
| 21 | 72 | 22 | 560 |
| 23 | 110 | 24 | 45 |
| 25 | 73 | 26 | 38 |
| 27 | 193 | 28 | 674 |
| 29 | 38 | 30 | 2926 |
| 31 | 126 | 32 | 339 |
| 33 | 221 | 34 | 581 |
| 35 | 579 | 37 | 63 |
| 38 | 18 | 39 | 196 |
| 40 | 12 | 41 | 649 |
| 42 | 144 | 43 | 15 |
| 44 | 322 | 45 | 15 |
| 46 | 16 | 47 | 126 |
| 48 | 237 | 49 | 102 |
| 50 | 13 | 51 | 48 |
| 52 | 415 | 53 | 6.9 |
| 54 | 98 | 55 | 13 |
| 56 | 19 | 57 | 56 |
| 58 | 46 | 59 | 39 |
| 60 | 64 | 61 | 114 |
| 63 | 74 | / | / |

Wherein, SB431542 (CAS No.: 301836-41-9) is a known ALK5 inhibitor having following structure:

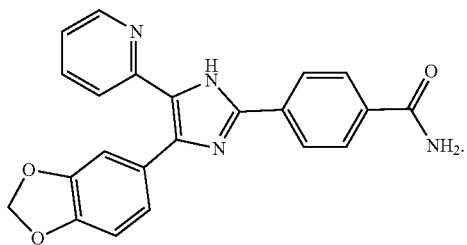

SB431542

It can be confirmed from the above results of the assay that the compound of the present invention has a significant inhibitory effect toward ALK5.

It is to be understood that the foregoing description of the preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A nitrogenous aromatic heterocyclic compound represented by formula I or a pharmaceutically acceptable salt thereof:

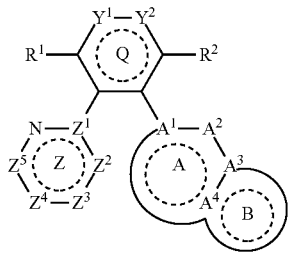

I wherein, ring Z is a pyridine ring or a 5 membered heteroaromatic ring having at least one N;

ring Q is a benzene ring;

ring A is a substituted or unsubstituted benzene ring or a substituted or unsubstituted pyridine ring;

ring B is a substituted or unsubstituted 5-6 membered heteroaromatic ring; in the definition of ring B, the substituted or unsubstituted 5-6 membered heteroaromatic ring is substituted or unsubstituted imidazole ring, substituted or unsubstituted pyrimidine ring, substituted or unsubstituted pyridazine ring, substituted or unsubstituted pyrazine ring, substituted or unsubstituted triazole ring or substituted or unsubstituted furan ring;

$Z^1$ is N or C;

$Z^2$ is S, O, N or $CR^{2'}$;

$Z^3$ is S, N or $CR^{3'}$;

$Z^4$ is N, $NR^{a3}$ or $CR^{4'}$;

$Z^5$ is $CR^{5'}$ or a single bond;

when $Z^1$ is N, $Z^5$ is a single bond;

when $Z^2$ is S or O, or $Z^3$ is S, or $Z^4$ is $NR^{a3}$, $Z^1$ is C and $Z^5$ is a single bond;

when $Z^2$ is S or O, $Z^3$ is N or $CR^{3'}$, $Z^4$ is N or $CR^{4'}$, $Z^3$ and $Z^4$ are not N simultaneously;

when $Z^3$ is S, $Z^2$ is N or $CR^{2'}$, $Z^4$ is N or $CR^{4'}$, $Z^2$ and $Z^4$ are not N simultaneously;

$Y^1$ is $CR^4$;

$Y^2$ is $CR^5$;

$A^1$ is C; each of $A^3$ and $A^4$ is independently N or C, $A^2$ is N, $CR^{a4}$, $CR^{10}$ or $CR^{13}$, $R^{13}$ is halogen, deuterium or cyano;

each of $R^1$ and $R^2$ is independently hydrogen, deuterium, halogen, cyano, nitro, substituted or unsubstituted $C_{1-6}$ alkyl, $C_{2-8}$ alkenyl, $C_{2-8}$ alkynyl, $C_{3-8}$ cycloalkyl, 3-10 membered heterocyclyl, or $—R^9$, the substituent in the substituted $C_{1-6}$ alkyl is selected from the group consisting of deuterium, halogen, $C_{3-8}$ cycloalkyl, 3-10 membered heterocyclyl and $R^{10}$, when there are more substituents than one, the substituents are the same or different; $R^9$ is $—OR^{b1}$, $—NR^{b2}R^{b3}$, $—SR^{b4}$, $—C(O)OR^{b5}$, $—C(O)NR^{b6}R^{b7}$, $—C(O)N(R^{b8})OR^{b9}$, $—C(O)R^{b10}$, $—S(O)R^{b11}$, $—S(O)OR^{b12}$, $—S(O)_2R^{b13}$, $—S(O)_2OR^{b14}$, $—OC(O)R^{b15}$, $—OC(O)OR^{b16}$, $—OC(O)NR^{b17}R^{b18}$, $—N(R^{b19})C(O)R^{b20}$, $—N(R^{b21})C(O)OR^{b22}$, $—N(R^{b23})C(O)NR^{b24}R^{b25}$, $—N(R^{b26})S(O)_2R^{b27}$, $—N(R^{b28})S(O)_2NR^{b29}R^{b30}$, $—P(O)(OR^{b31})(NR^{b32}R^{b33})$ or $—OP(O)(OR^{b34})_2$; or, $R^{b2}$ and $R^{b3}$, $R^{b6}$ and $R^{b7}$, $R^{b17}$ and $R^{b18}$, $R^{b24}$ and $R^{b25}$, $R^{b29}$ and $R^{b30}$, $R^{b32}$ and $R^{b33}$ together with the N to which they are attached form a substituted or unsubstituted 3-10 membered heterocyclyl, the substituent in the substituted heterocyclyl is one or more than one $R^{a6}$, when there are more substituents than one, the substituents are the same or different; the substituted or unsubstituted 3-10 membered heterocyclyl refers to be a substituted or unsubstituted 3-10 membered heterocyclyl having 1-5 heteroatoms selected from the group consisting of O, N and S;

$R^4$ is independently hydrogen, deuterium, halogen, cyano, nitro, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-8}$ cycloalkyl, substituted or unsubstituted $C_{3-8}$ cycloalkenyl, substituted or unsubstituted 3-10 membered heterocyclyl, substituted or unsubstituted aryl, substituted or unsubstituted heteroaryl or —$R^{100}$; the substituent in the substituted $C_{1-6}$ alkyl is selected from the group consisting of deuterium, halogen, $C_{3-8}$ cycloalkyl, $C_{3-8}$ cycloalkyl substituted by 1 to 3 $R^{101}$ and/or $R^{121}$, $C_{3-8}$ cycloalkenyl, $C_{3-8}$ cycloalkenyl substituted by 1 to 3 $R^{102}$ and/or $R^{122}$, 3-10 membered heterocyclyl, 3-10 membered heterocyclyl substituted by 1 to 3 $R^{103}$ and/or $R^{123}$, aryl, aryl substituted by 1 to 3 $R^{104}$ and/or $R^{124}$, heteroaryl, heteroaryl substituted by 1 to 3 $R^{105}$ and/or $R^{125}$, $R^{106}$ and $R^{126}$; the substituent in the substituted $C_{2-8}$ alkenyl, the substituted $C_{2-8}$ alkynyl, the substituted $C_{3-8}$ cycloalkyl, the substituted $C_{3-8}$ cycloalkenyl, the substituted 3-10 membered heterocyclyl, the substituted aryl or the substituted heteroaryl is selected from the group consisting of $R^{107}$ and $R^{127}$, when there are more substituents than one, the substituents are the same or different;

$R^5$ is hydrogen, deuterium, halogen, cyano, nitro, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-8}$ cycloalkyl, substituted or unsubstituted $C_{3-8}$ cycloalkenyl, substituted or unsubstituted 3-10 membered heterocyclyl, substituted or unsubstituted aryl, substituted or unsubstituted heteroaryl or —$R^{100}$; the substituent in the substituted $C_{1-6}$ alkyl is selected from the group consisting of deuterium, halogen, $C_{3-8}$ cycloalkyl, $C_{3-8}$ cycloalkyl substituted by 1 to 3 $R^{101}$ and/or $R^{121}$, $C_{3-8}$ cycloalkenyl, $C_{3-8}$ cycloalkenyl substituted by 1 to 3 $R^{102}$ and/or $R^{122}$, 3-10 membered heterocyclyl, 3-10 membered heterocyclyl substituted by 1 to 3 $R^{103}$ and/or $R^{123}$, aryl, aryl substituted by 1 to 3 $R^{104}$ and/or $R^{124}$, heteroaryl, heteroaryl substituted by 1 to 3 $R^{105}$ and/or $R^{125}$, and $R^{126}$; the substituent in the substituted $C_{2-8}$ alkenyl, the substituted $C_{2-8}$ alkynyl, the substituted $C_{3-8}$ cycloalkyl, the substituted $C_{3-8}$ cycloalkenyl, the substituted 3-10 membered heterocyclyl, the substituted aryl or the substituted heteroaryl is selected from the group consisting of $R^{107}$ and $R^{127}$, when there are more substituents than one, the substituents are the same or different;

each of $R^{2'}$, $R^{3'}$, $R^{4'}$ and $R^{5'}$ is independently hydrogen, deuterium, halogen, cyano, nitro, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-8}$ cycloalkyl, substituted or unsubstituted $C_{3-8}$ cycloalkenyl, substituted or unsubstituted 3-10 membered heterocyclyl, substituted or unsubstituted aryl, substituted or unsubstituted heteroaryl, and —$R^{11}$; the substituent in the substituted $C_{1-6}$ alkyl is selected from the group consisting of deuterium, halogen, $C_{3-8}$ cycloalkyl, $C_{3-8}$ cycloalkyl substituted by 1 to 3 $R^{109}$ and/or $R^{129}$, $C_{3-8}$ cycloalkenyl, $C_{3-8}$ cycloalkenyl substituted by 1 to 3 $R^{1010}$ or $R^{1210}$, 3-10 membered heterocyclyl, 3-10 membered heterocyclyl substituted by 1 to 3 $R^{1011}$ and/or $R^{1211}$, aryl, aryl substituted by 1 to 3 $R^{1012}$ and/or $R^{1212}$, heteroaryl, heteroaryl substituted by 1 to 3 $R^{1013}$ and/or $R^{1213}$, $R^{1014}$ and $R^{1214}$; the substituent in the substituted $C_{2-8}$ alkenyl, the substituted $C_{2-8}$ alkynyl, the substituted $C_{3-8}$ cycloalkyl, the substituted $C_{3-8}$ cycloalkenyl, the substituted 3-10 membered heterocyclyl, the substituted aryl or the substituted heteroaryl is selected from the group consisting of $R^{1015}$ and $R^{1215}$;

each of $R^{a3}$, $R^{a4}$, $R^{a6}$, $R^{b1-b34}$ and $R^{c1-c38}$ is independently hydrogen, $C_{1-4}$ acyl, substituted or unsubstituted $C_{1-6}$ alkyl, substituted or unsubstituted $C_{6-10}$ aryl, substituted or unsubstituted heteroaryl, substituted or unsubstituted $C_{3-8}$ cycloalkyl, substituted or unsubstituted $C_{3-8}$ cycloalkenyl or substituted or unsubstituted 3-10 membered heterocyclyl; the substituent in the substituted $C_{1-6}$ alkyl, the substituted $C_{6-10}$ aryl, the substituted heteroaryl, the substituted $C_{3-8}$ cycloalkyl, the substituted $C_{3-8}$ cycloalkenyl or the substituted 3-10 membered heterocyclyl is selected from the group consisting of halogen, deuterium, cyano, oxo, $C_{1-6}$ alkyl, $C_{1-6}$ alkyl substituted by halogen, aryl, aryl substituted by halogen, heteroaryl, $C_{3-8}$ cycloalkyl, $C_{3-8}$ cycloalkenyl, 3-10 membered heterocyclyl, —$OR^{d1}$, —$NR^{d2}R^{d3}$, —$SR^{d4}$, —$C(O)OR^{d5}$, —$C(O)NR^{d6}R^{d7}$, —$C(O)N(R^{d8})OR^{d9}$, —$C(O)R^{d10}$, —$S(O)R^{d11}$, —$S(O)OR^{d12}$, —$S(O)NR^{d13}R^{d14}$, —$S(O)_2R^{d15}$, —$S(O)_2OR^{d16}$, —$S(O)_2NR^{d17}R^{d18}$, —$OC(O)R^{d19}$, —$OC(O)OR^{d20}$, —$OC(O)NR^{d21}R^{d22}$, —$N(R^{d23})C(O)R^{d24}$, —$N(R^{d25})C(O)OR^{d26}$, —$N(R^{d27})C(O)NR^{d28}R^{d29}$, —$N(R^{d30})S(O)_2R^{d31}$, $N(R^{d32})C(=NR^{d33})NR^{d34}$ and —$OP(O)(OR^{d35})_2$; each of $R^{d1-d35}$ is independently hydrogen, substituted or unsubstituted $C_{1-6}$ alkyl or substituted or unsubstituted $C_{3-8}$ cycloalkyl; the substituent in the substituted $C_{1-6}$ alkyl or the substituted $C_{3-8}$ cycloalkyl is selected from the group consisting of halogen, deuterium, cyano, oxo, $C_{1-6}$ alkyl and $C_{1-6}$ alkyl substituted by halogen; or, $R^{d2}$ and $R^{d3}$, $R^{d6}$ and $R^{d7}$, $R^{d13}$ and $R^{d14}$, $R^{d17}$ and $R^{d18}$, $R^{d21}$ and $R^{d22}$ or $R^{d28}$ and $R^{d29}$ together with the N to which they are attached form a substituted or unsubstituted 3-10 membered heterocyclyl, the substituent in the substituted 3-10 membered heterocyclyl is $R^{1216}$;

in the definition of ring A, the substituent in the substituted benzene ring or the pyridine ring is selected from the group consisting of deuterium, halogen, cyano, nitro, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-8}$ cycloalkyl, substituted or unsubstituted $C_{3-8}$ cycloalkenyl, substituted or unsubstituted 3-10 membered heterocyclyl, substituted or unsubstituted aryl, substituted or unsubstituted heteroaryl and —$R^{1016}$; the substituent in the substituted $C_{1-6}$ alkyl is selected from the group consisting of deuterium, halogen, $C_{3-8}$ cycloalkyl, $C_{3-8}$ cycloalkyl substituted by 1 to 3 $R^{1017}$ and/or $R^{1217}$, $C_{3-8}$ cycloalkenyl, $C_{3-8}$ cycloalkenyl substituted by 1 to 3 $R^{1018}$ and/or $R^{1218}$, 3-10 membered heterocyclyl, 3-10 membered heterocyclyl substituted by 1 to 3 $R^{1019}$ and/or $R^{1219}$, aryl, aryl substituted by 1 to 3 $R^{1020}$ and/or $R^{1220}$, heteroaryl, heteroaryl substituted by 1 to 3 $R^{1021}$ and/or $R^{1221}$, $R^{1022}$ and $R^{1222}$; the substituent in the substituted $C_{2-8}$ alkenyl, the substituted $C_{2-8}$ alkynyl, the substituted $C_{3-8}$ cycloalkyl, the substituted $C_{3-8}$ cycloalkenyl, the substituted 3-10 membered heterocyclyl, the substituted aryl or the substituted heteroaryl is selected from the group consisting of $R^{1023}$ and $R^{1223}$;

in the definition of ring B, the substituent in the substituted imidazole ring is selected from the group consisting of oxo, cyano, methyl, ethyl, n-propyl, isopropyl, n-butyl, isobutyl, tert-butyl, isopentyl, neopentyl, 2-methylpentyl, 3-methylpentyl, 2,2-dimethylbutyl or 2,3-dimethylbutyl, substituted $C_{1-6}$ alkyl, heteroaryl and $R^{1016}$; the substituent in the substituted $C_{1-6}$ alkyl is selected from the group consisting of deuterium, halogen, $C_{3-8}$ cycloalkyl, $C_{3-8}$ cycloalkyl substituted by 1 to 3 $R^{1017}$ and/or $R^{1217}$, $C_{3-8}$ cycloalkenyl, $C_{3-8}$ cycloalkenyl substituted by 1 to 3 $R^{1018}$ and/or $R^{1218}$, 3-10 membered heterocyclyl, 3-10 membered heterocyclyl substituted by 1 to 3 $R^{1019}$ and/or $R^{1219}$, aryl, aryl substituted by 1 to 3 $R^{1020}$ and/or $R^{1220}$;

in the definition of ring B, the substituent in the substituted imidazole ring, substituted is selected from the group consisting of oxo, cyano, methyl, ethyl, n-propyl, isopropyl, n-butyl, isobutyl, tert-butyl, isopentyl, neopentyl, n-hexyl, 2-methylpentyl, 3-methylpentyl, 2,2-dimethylbutyl or 2,3-dimethylbutyl, substituted $C_{1-6}$ alkyl, heteroaryl and $R^{1016}$; the substituent in the substituted $C_{1-6}$ alkyl is selected from the group consisting of deuterium, halogen, $C_{3-8}$ cycloalkyl, $C_{3-8}$ cycloalkyl substituted by 1 to 3 $R^{1017}$ and/or $R^{1217}$, $C_{3-8}$ cycloalkenyl, $C_{3-8}$ cycloalkenyl substituted by 1 to 3 $R^{1018}$ and/or $R^{1218}$, 3-10 membered heterocyclyl, 3-10 membered heterocyclyl substituted by 1 to 3 $R^{1019}$ and/or $R^{1219}$, aryl, aryl substituted by 1 to 3 $R^{1020}$ and/or $R^{1220}$, heteroaryl, heteroaryl substituted by 1 to 3 $R^{1021}$ and/or $R^{1221}$;

in the definition of the substituent in ring B, $R^{1016}$ is —$NR^{c2}R^{c3}$, —$C(O)OR^{c5}$, —$C(O)NR^{c6}R^{c7}$, —$C(O)N(R^{c8})OR^9$ or —$S(O)NR^{c13}R^{c14}$, wherein each of $R^{c2}$, $R^{c3}$, $R^{c5}$, $R^{c6}$, $R^{c7}$, $R^{c8}$, $R^9$, $R^{c13}$ and $R^{c14}$ is independently hydrogen, $C_{1-4}$ acyl, substituted or unsubstituted $C_{1-6}$ alkyl, $C_{3-8}$ cycloalkyl or 3-10 membered heterocyclyl; the substituent in the substituted $C_{1-6}$ alkyl is selected from the group consisting of deuterium and 3-10 membered heterocyclyl, when there are more substituents than one, the substituents are the same or different;

each of $R^{10}$ to $R^{1023}$ and $R^{11}$ is independently —$OR^{c1}$, —$NR^{c2}R^{c3}$, —$SR^{c4}$, —$C(O)OR^{c5}$, —$C(O)NR^{c6}R^{c7}$, —$C(O)N(R^{c8})OR^{c9}$, —$C(O)R^{c10}$, —$C(NH)NR^{c2}R^{c3}$, —$S(O)R^{c11}$, —$S(O)OR^{c12}$, —$S(O)NR^{c13}R^{c14}$, —$S(O)_2 R^{c15}$, —$S(O)_2OR^{c16}$, —$S(O)_2NR^{c17}R^{c18}$, —$OC(O)R^{c19}$, —$OC(O)OR^{c20}$, —$OC(O)NR^{c21}R^{c22}$, —$N(R^{c23})C(O)R^{c24}$, —$N(R^{c25})C(O)OR^{c26}$, —$N(R^{c27})C(O)NR^{c28}R^{c29}$, —$N(R^{c30})S(O)_2R^{c31}$, —$N(R^{c32})S(O)_2 NR^{c33}R^{c34}$, —$P(O)(OR^{c35})(NR^{c36}R^{c37})$ or —$OP(O)(OR^{c38})_2$; or, $R^{c2}$ and $R^{c3}$, $R^{c6}$ and $R^{c7}$, $R^{c13}$ and $R^{c14}$, $R^{c17}$ and $R^{c18}$, $R^{c21}$ and $R^{c22}$, $R^{c28}$ and $R^{c29}$, $R^{c33}$ and $R^{c34}$, or $R^{c36}$ and $R^{c37}$ together with the N to which they are attached form a substituted or unsubstituted 3-10 membered heterocyclyl, the substituent in the substituted 3-10 membered heterocyclyl is one or more than one $R^{a6}$; when there are more substituents than one, the substituents are the same or different; the substituted or unsubstituted 3-10 membered heterocyclyl refers to be a substituted or unsubstituted 3-10 membered heterocyclyl having 1-5 heteroatoms selected from the group consisting of O, N and S;

each of $R^{121}$ to $R^{1223}$ is independently halogen, deuterium, cyano, oxo, $C_{1-6}$ alkyl or $C_{1-6}$ alkyl substituted by halogen;

when $Z^3$ is S, $Z^2$ is $CR^{2'}$, $Z^4$ is $CR^{4'}$, and ring Q is benzene ring, $R^{4'}$ is not —$NR^{c2}R^{c3}$ or —$N(R^{c23})C(O)R^{c24}$;

when ring Q is benzene ring, $R^2$ is not —$CH(CO_2H)OC(CH_3)_3$;

when ring Q is benzene ring, and ring Z is tetrazole ring, ring B is not substituted by —$CF_3$ or the moiety

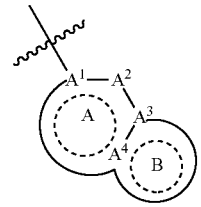

is not

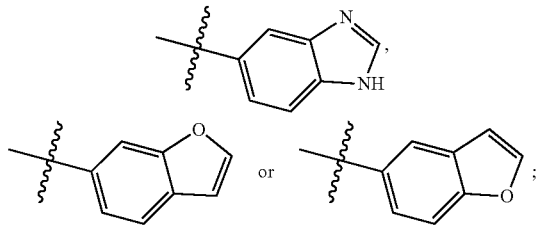

when $Z^2$ is O, $Z^4$ is N, ring Q is benzene ring, and ring A is a 5-membered heteroaromatic ring, ring A is not substituted by —$NR^{c2}R^{c3}$;

when $Z^1$ is N, $Z^2$ is $CR^{2'}$, $Z^3$ is $CR^{3'}$, $Z^4$ is $CR^{4'}$, and ring Q is benzene ring, the moiety

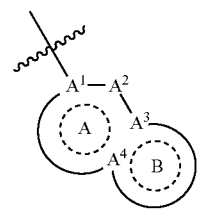

is not

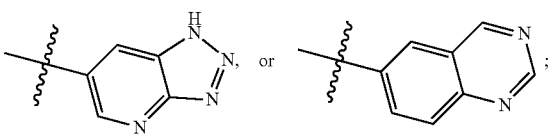 [SMILES: *c1cnc2nn[nH]c2c1 ; *c1ccc2ncncc2c1]

when $Z^2$ is S, $Z^3$ is $CR^{3'}$, $Z^4$ is $CR^{4'}$, ring Q is benzene ring, and ring B is a 6-membered nitrogenous heteroaromatic ring, ring B is not substituted by —$NR^{c2}R^{c3}$.

2. The nitrogenous aromatic heterocyclic compound represented by formula I or the pharmaceutically acceptable salt thereof as defined in claim 1, wherein, the 3-10 membered heterocyclyl, the 3-10 membered heterocyclyl contained in the substituted or unsubstituted 3-10 membered heterocyclyl and the 3-10 membered heterocyclyl contained in the 3-10 membered heterocyclyl substituted by 1 to 3 $R^{10x1}$ and/or $R^{12x1}$ are each independently a 3-10 membered heterocyclyl having 1-4 heteroatoms independently selected from the group consisting of N, O and S; x1 is 3, 11 or 19;

and/or, the aryl, the aryl contained in the substituted or unsubstituted aryl and the aryl contained in the aryl substituted by 1 to 3 $R^{10x2}$ and/or $R^{12x2}$ are each independently $C_6$-$C_{10}$ aryl; x2 is 4, 12 or 20;

and/or, the heteroaryl, the heteroaryl contained in the substituted or unsubstituted heteroaryl and the heteroaryl contained in the heteroaryl substituted by 1 to 3 $R^{10x3}$ and/or $R^{12x3}$ are each independently a $C_1$-$C_{10}$ heteroaryl having 1-4 heteroatoms selected from the group consisting of N, O and S; x3 is 5, 13 or 21;

and/or, the halogen is F, $C_1$, Br or I;

and/or, the $C_{1-4}$ acyl is formyl, acetyl, propionyl or butyryl;

and/or, the $C_{1-6}$ alkyl contained in the substituted or unsubstituted $C_{1-6}$ alkyl and the $C_{1-6}$ alkyl are each independently methyl, ethyl, n-propyl, isopropyl, n-butyl, isobutyl, tert-butyl, n-pentyl, isopentyl, neopentyl, n-hexyl, 2-methylpentyl, 3-methylpentyl, 2,2-dimethylbutyl or 2,3-dimethylbutyl;

and/or, the $C_{3-8}$ cycloalkyl, the $C_{3-8}$ cycloalkyl contained in the substituted or unsubstituted $C_{3-8}$ cycloalkyl, and the $C_{3-8}$ cycloalkyl contained in the $C_{3-8}$ cycloalkyl substituted by 1 to 3 $R^{10x4}$ and/or $R^{12x4}$ are independently cyclopropyl, cyclobutyl, cyclopentyl or cyclohexyl; x4 is 1, 9, or 17;

and/or, the $C_{2-8}$ alkenyl and the $C_{2-8}$ alkenyl contained in the substituted or unsubstituted $C_{2-8}$ alkenyl are each independently $C_2$-$C_4$ alkenyl;

and/or, the $C_{2-8}$ alkynyl and the $C_{2-8}$ alkynyl contained in the substituted or unsubstituted $C_{2-8}$ alkynyl are each independently $C_2$-$C_4$ alkynyl;

and/or, the $C_{3-8}$ cycloalkenyl and the $C_{3-8}$ cycloalkenyl contained in the substituted or unsubstituted $C_{3-8}$ cycloalkenyl are each independently cyclopropenyl, cyclobutenyl, cyclopentenyl, and cyclohexenyl, cycloheptenyl, 1,3-cyclohexadienyl or 1,4-cyclohexadienyl; x5 is 2, 10 or 18.

3. The nitrogenous aromatic heterocyclic compound represented by formula I or the pharmaceutically acceptable salt thereof as defined in claim 1, wherein, the $C_{2-8}$ alkenyl and the $C_{2-8}$ alkenyl contained in the substituted or unsubstituted $C_{2-8}$ alkenyl are each independently vinyl, allyl, propenyl, 1-butenyl, 2-butenyl or 2-methylpropenyl;

and/or, the $C_{2-8}$ alkynyl and the $C_{2-8}$ alkynyl contained in the substituted or unsubstituted $C_{2-8}$ alkynyl are each independently ethynyl, propynyl, 1-butynyl, 2-butynyl or 3-methylpropynyl.

4. The nitrogenous aromatic heterocyclic compound represented by formula I or the pharmaceutically acceptable salt thereof as defined in claim 1, wherein, in the definition of ring Z, the 5 membered heteroaromatic ring having at least one N is a 5 membered heteroaromatic ring having 1-3 heteroatoms wherein the heteroatom is N, or selected from the group consisting of N and O, the group consisting of N and S, or the group consisting of N, O and S.

5. The nitrogenous aromatic heterocyclic compound represented by formula I or the pharmaceutically acceptable salt thereof as defined in claim 1, wherein, in the moiety

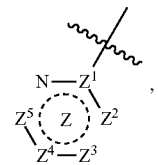

$Z^1$ is N or C; $Z^2$ is S, O, N or $CR^{2'}$; $R^{2'}$ is H or halogen; $Z^3$ is S, N or $CR^{3'}$, $R^{3'}$ is H; $Z^4$ is N, $NR^{a3}$ or $CR^{4'}$, $R^{a3}$ is hydrogen or $C_{1-6}$ alkyl, $R^{4'}$ is hydrogen, $C_{1-6}$ alkyl or halogen; $Z^5$ is $CR^{5'}$ or a single bond, $R^{5'}$ is hydrogen, substituted or unsubstituted $C_{1-6}$ alkyl or —$R^{11}$, wherein the substituent in the substituted $C_{1-6}$ alkyl is selected from the group consisting of deuterium and halogen; $R^{11}$ is —$OR^{c1}$, $R^{c1}$ is $C_{1-6}$ alkyl;

and/or, in the moiety

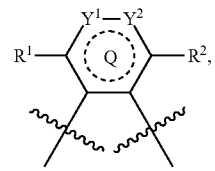

$Y^1$ is $CR^4$; $R^4$ is hydrogen or halogen; $Y^2$ is $CR^5$, $R^5$ is hydrogen, halogen, cyano or —$R^{100}$; —$R^{100}$ is —$OR^{c1}$, —$C(O)OR^{c5}$, —$C(O)NR^{c6}R^{c7}$ or —$C(O)R^{c10}$, $R^{c1}$ is substituted or unsubstituted $C_{1-6}$ alkyl, or substituted or unsubstituted $C_{6-10}$ aryl; $R^{c5}$ is $C_{1-6}$ alkyl; $R^{c6}$ and $R^{c7}$ are hydrogen; $R^{c10}$ is $C_{1-6}$ alkyl; the substituent in the substituted $C_{1-6}$ alkyl is selected from the group consisting of aryl or aryl substituted by halogen; the substituent in the substituted $C_{6-10}$ is one or more than one halogen.

6. The nitrogenous aromatic heterocyclic compound represented by formula I or the pharmaceutically acceptable salt thereof as defined in claim 1, wherein, in the definition of ring Z, the 5 membered heteroaromatic ring having at least one N is pyrazole ring, thiazole ring, oxazole ring or 1,2,4-oxadiazole ring.

7. The nitrogenous aromatic heterocyclic compound represented by formula I or the pharmaceutically acceptable salt thereof as defined in claim 1, wherein, the moiety

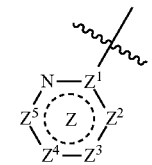

is

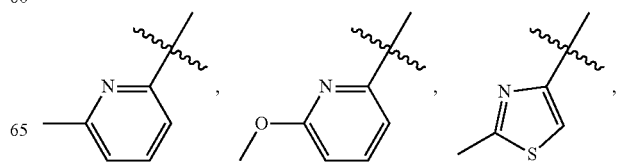

117
-continued
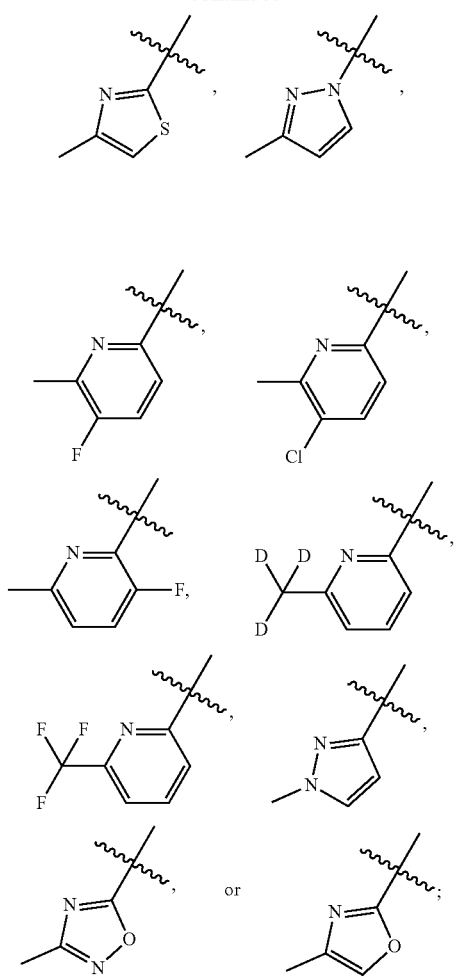
and/or, the moiety
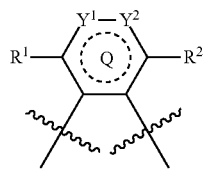
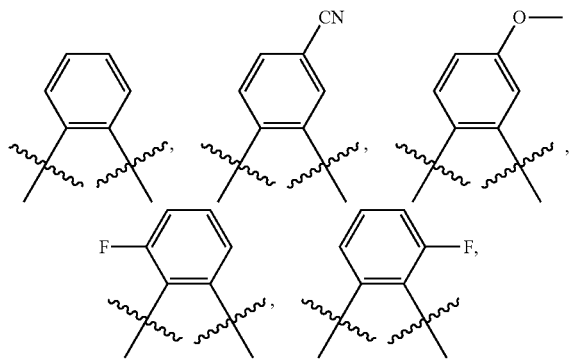
118
-continued
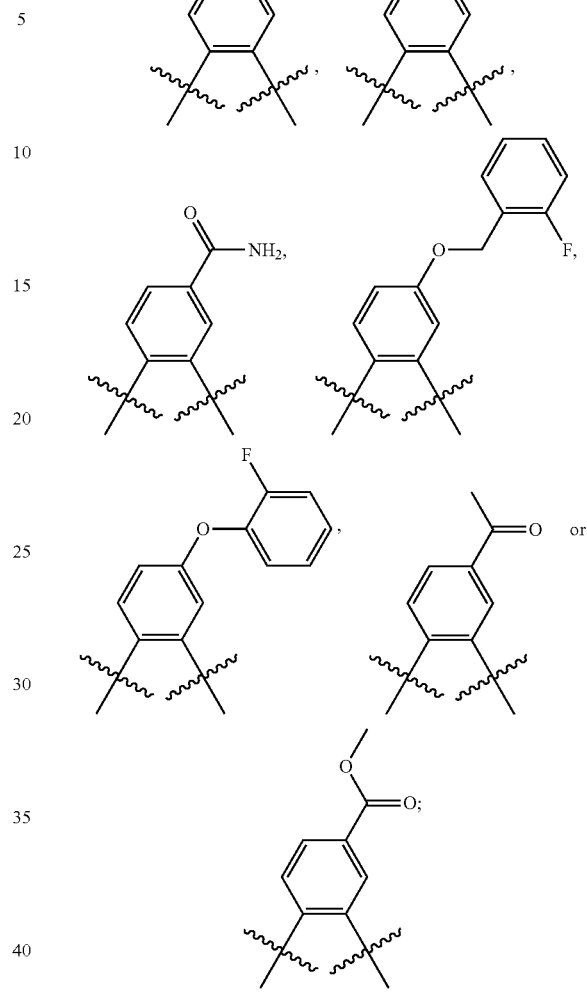
and/or, in the definition of ring B, the substituted 5-6 membered heteroaromatic ring is
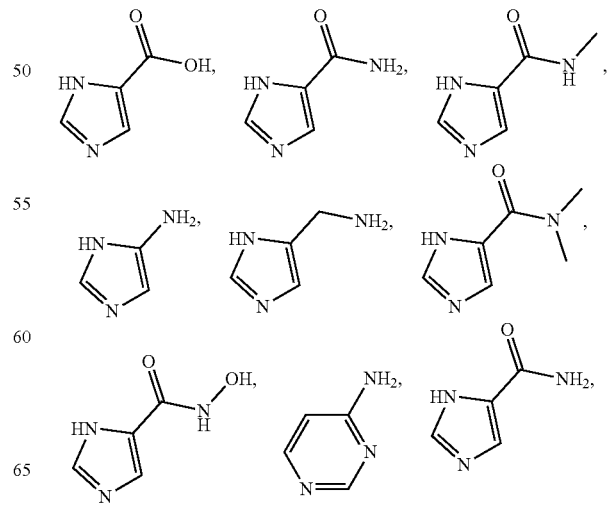

-continued
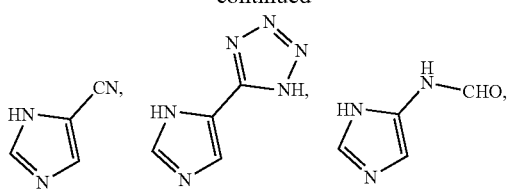
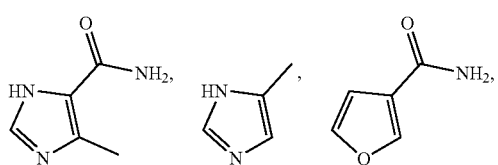
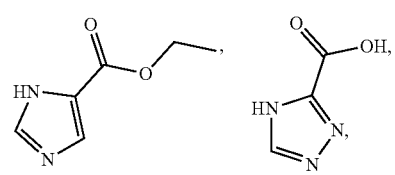
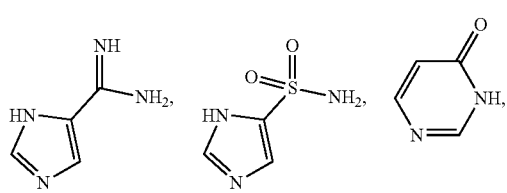
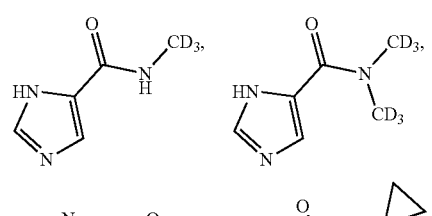
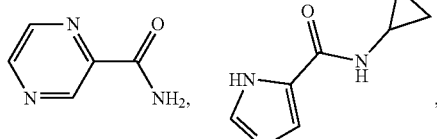
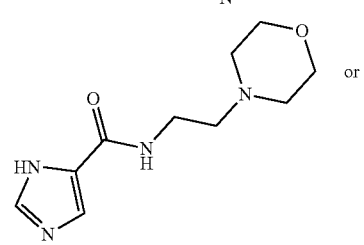
or
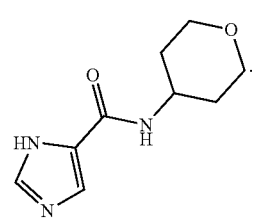
8. The nitrogenous aromatic heterocyclic compound represented by formula I or the pharmaceutically acceptable salt thereof as defined in claim 1, wherein,
the moiety
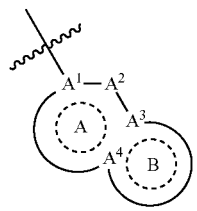
is
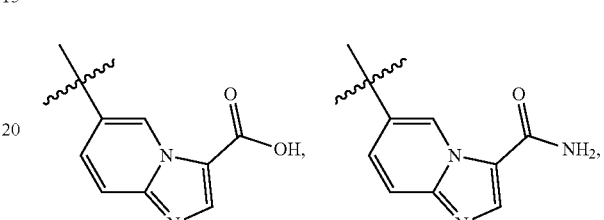
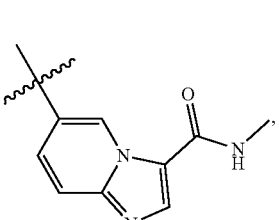
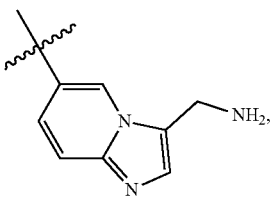
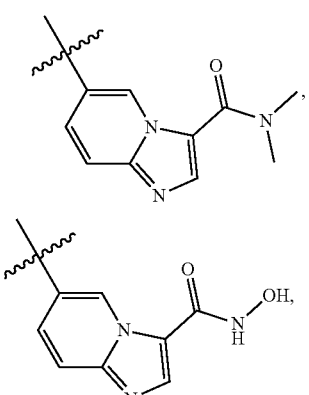
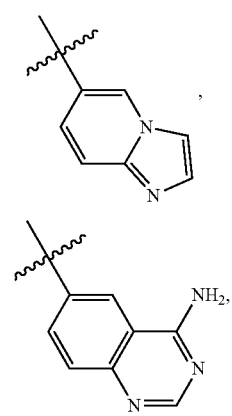
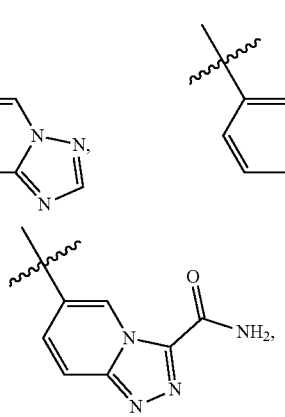

-continued
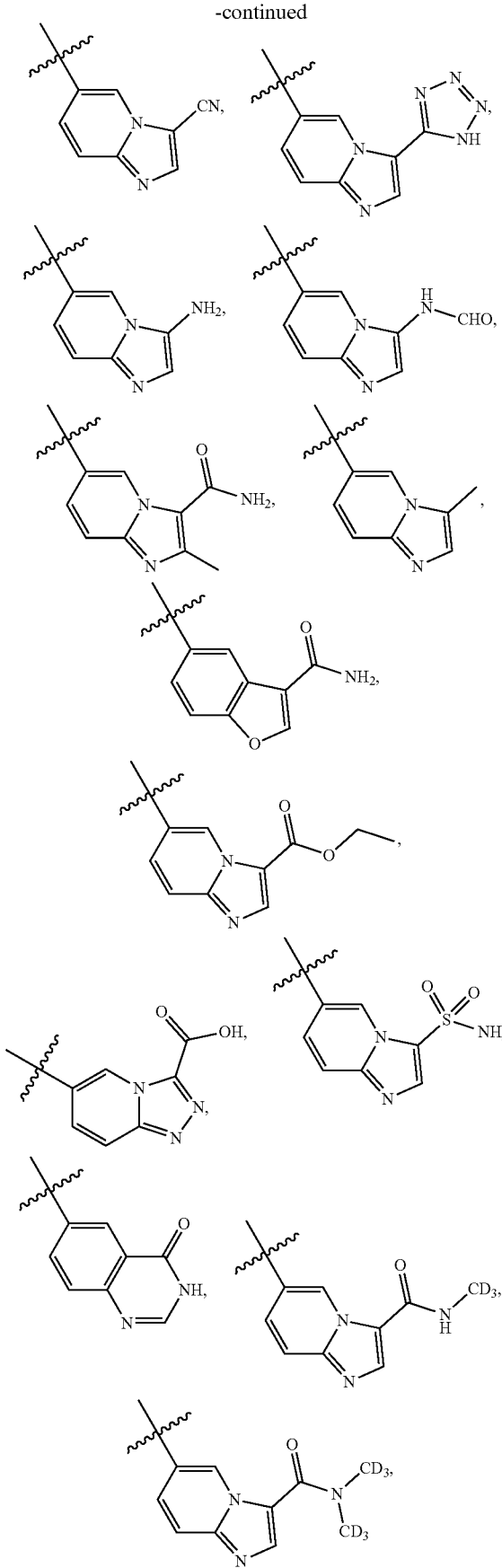
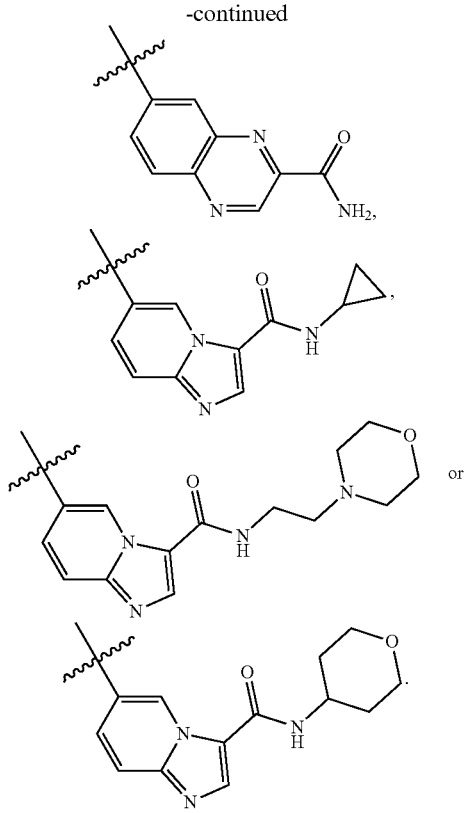
9. A nitrogenous aromatic heterocyclic compound or a pharmaceutically acceptable salt thereof selected from the group consisting of
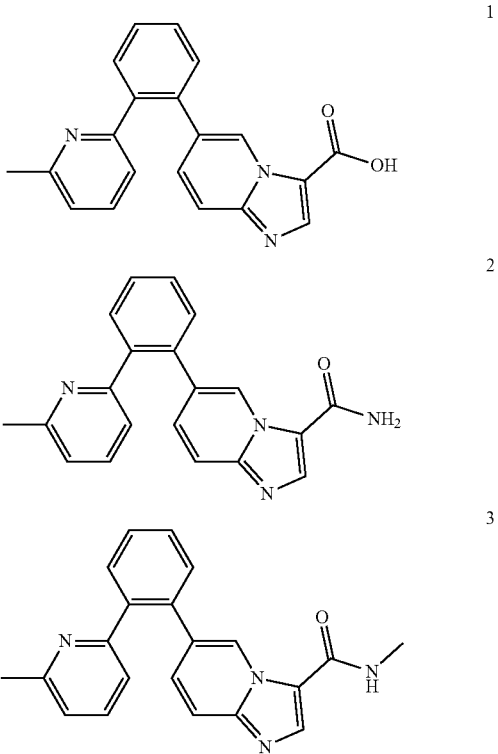

123
-continued
4
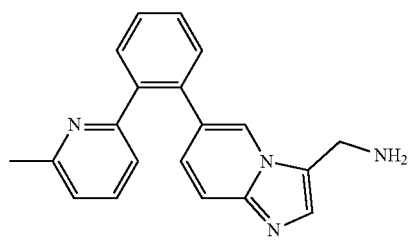
5
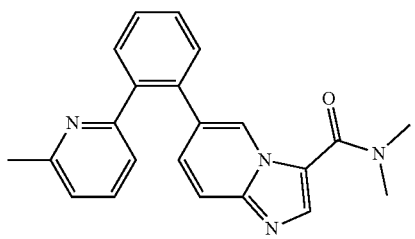
6
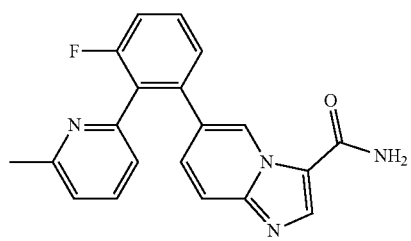
7
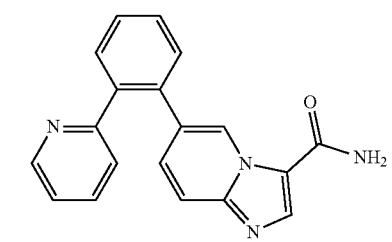
8
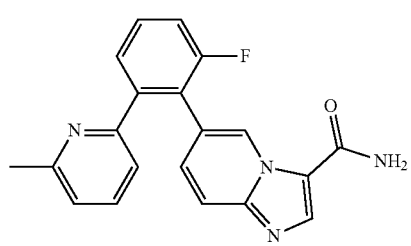
9
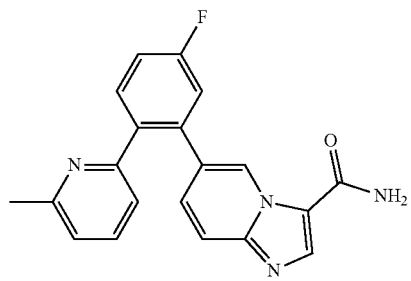
124
-continued
10
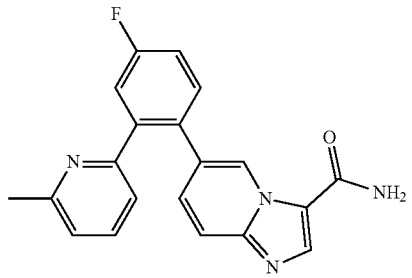
11
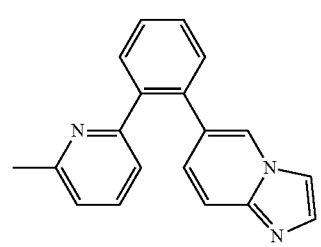
12
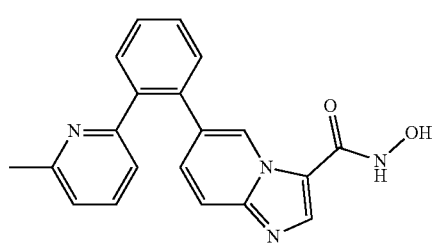
13
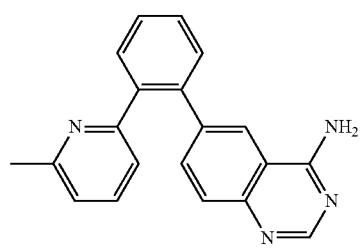
14
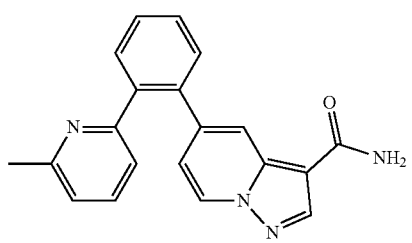
15
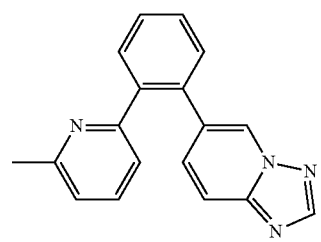

16
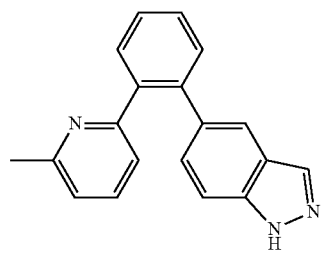
17
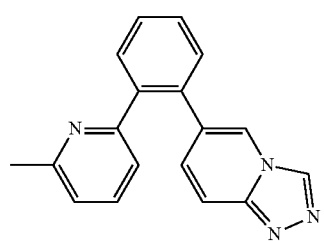
18
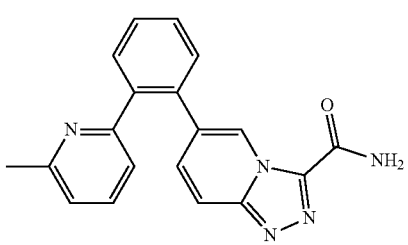
19
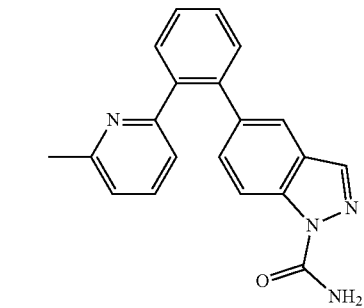
20
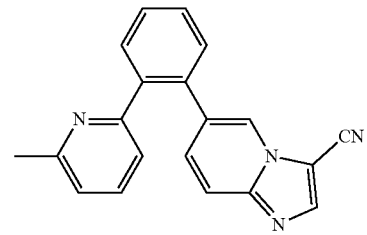
21
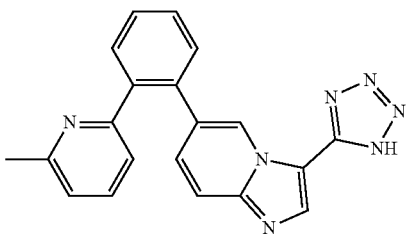
22
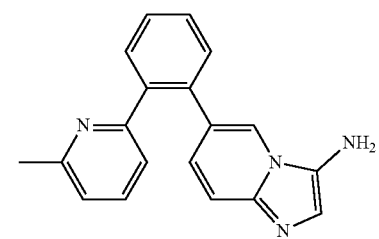
23
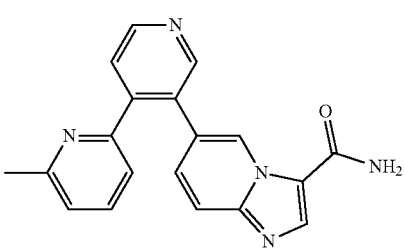
24
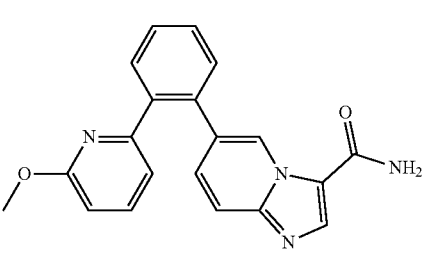
25
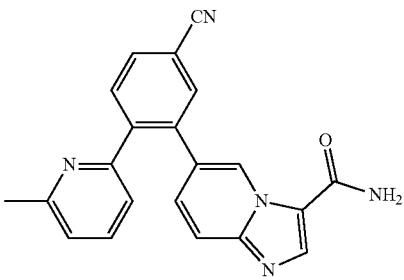
26
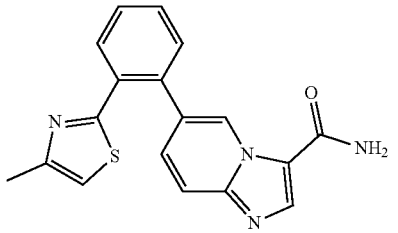
27
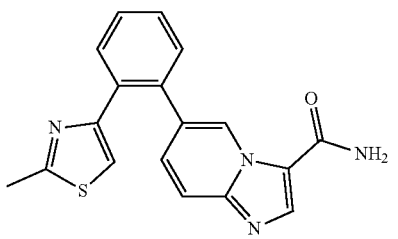

| 28 | 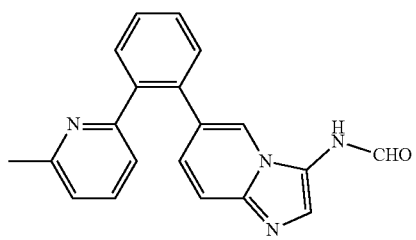 | 1-a | 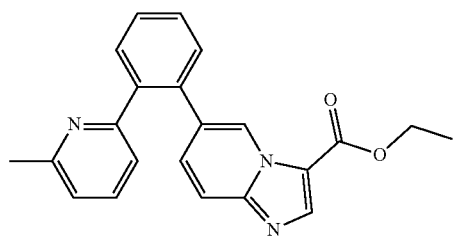 |
| 29 | 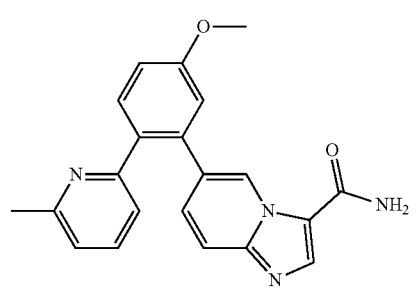 | 14-a1 | 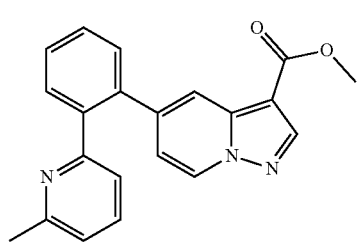 |
| 30 | 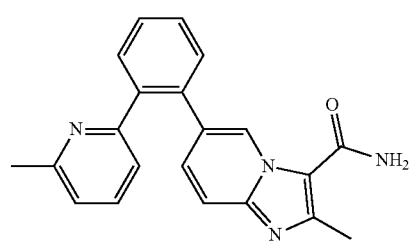 | 14-a | 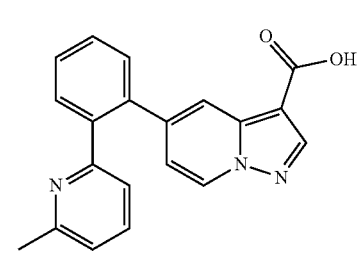 |
| 31 | 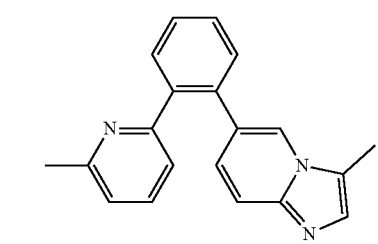 | 18-a | 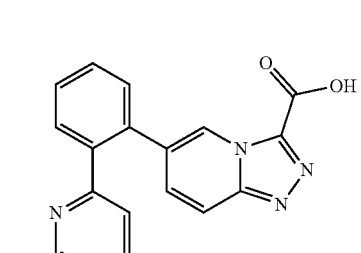 |
| 32 | 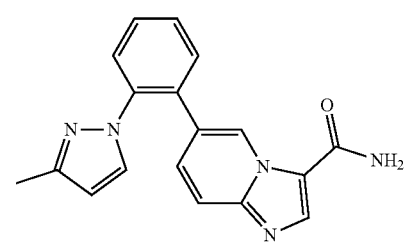 | 34 | 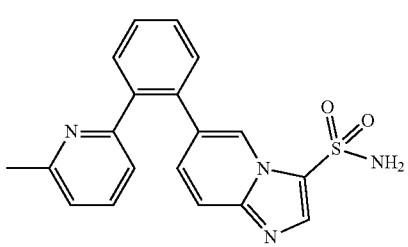 |
| 33 | 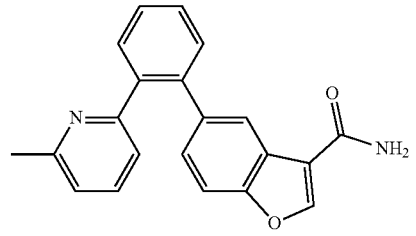 | 35 | 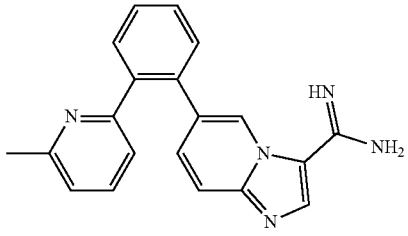 |

36
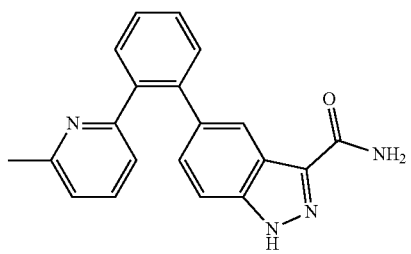
37
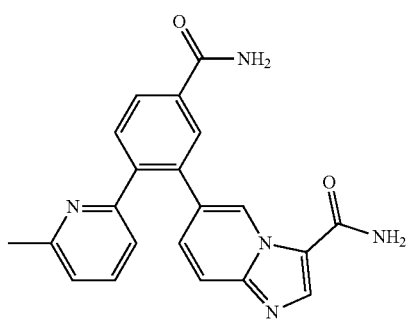
38
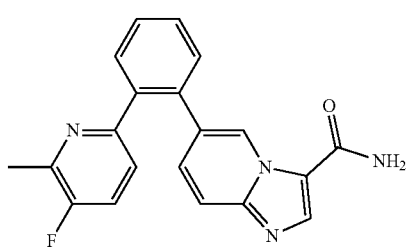
39
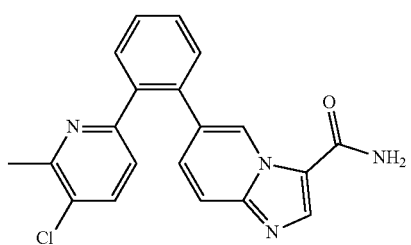
40
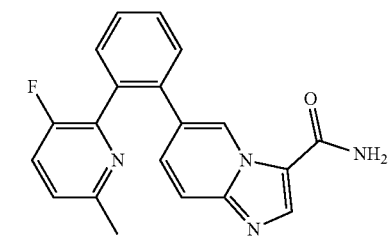
41
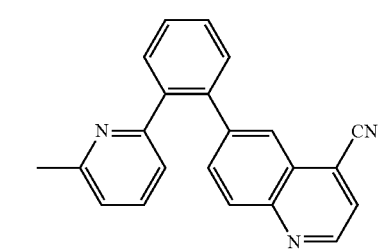
42
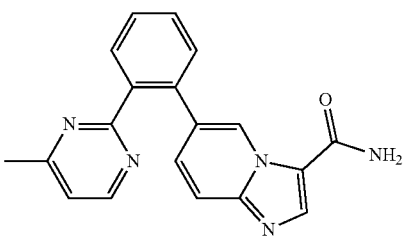
43
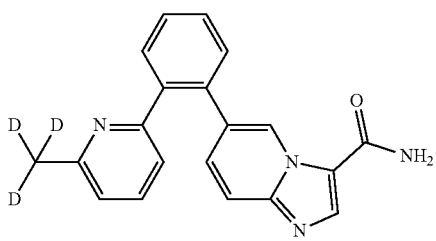
44
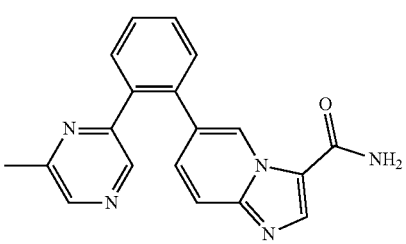
45
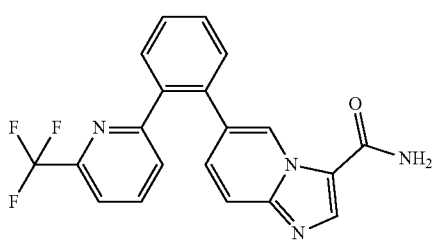
46
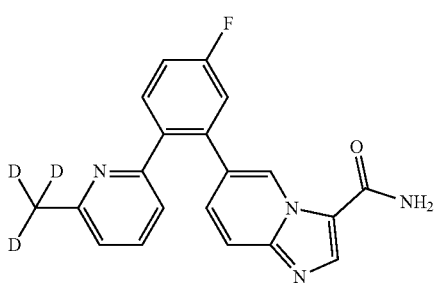
47
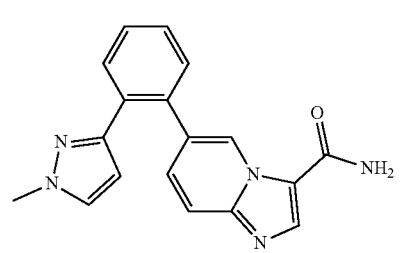

48 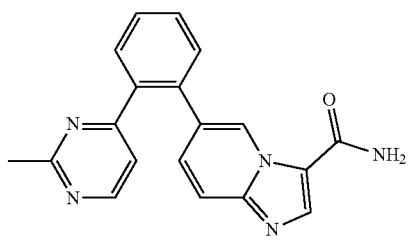
54 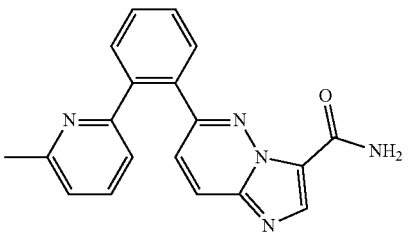
49 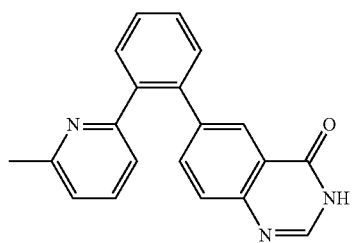
55 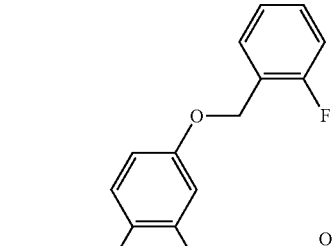
50 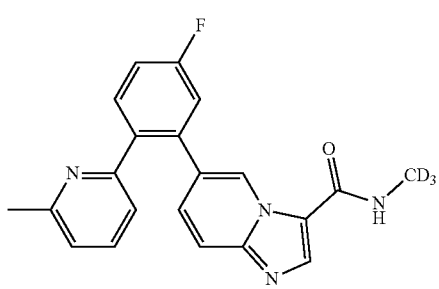
51 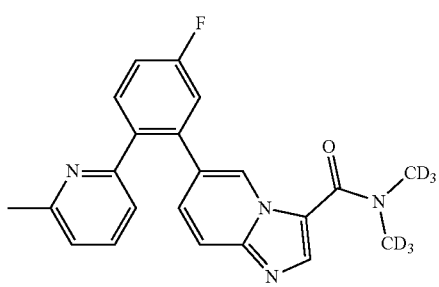
56 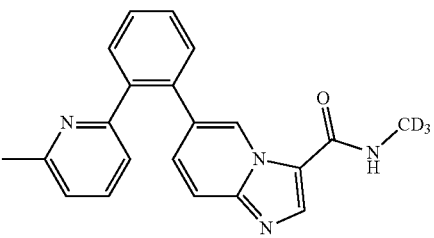
52 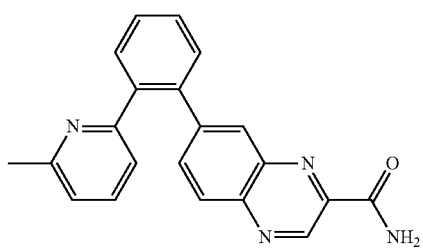
57 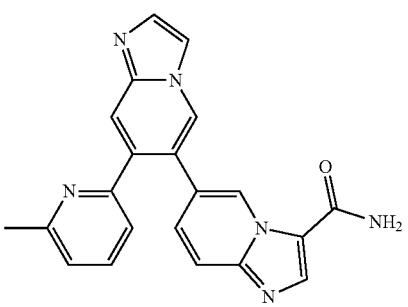
53 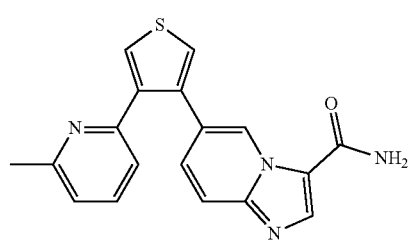
58 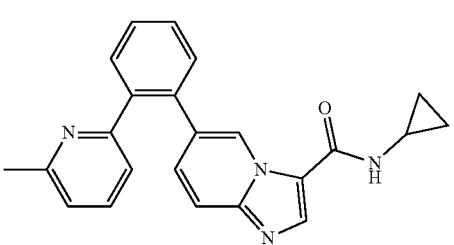

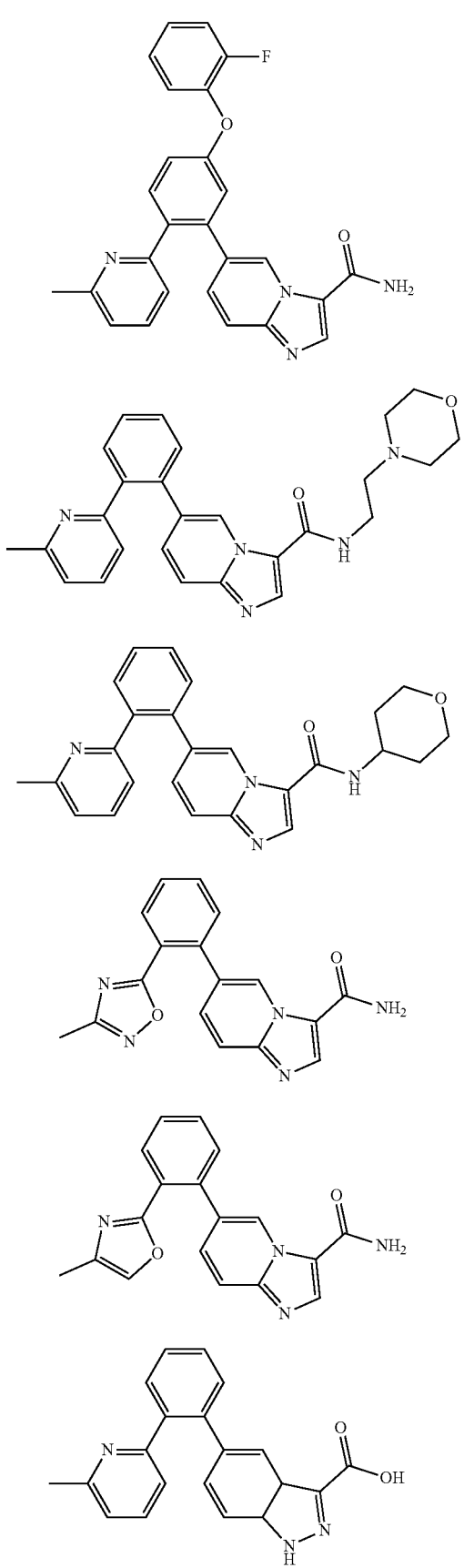
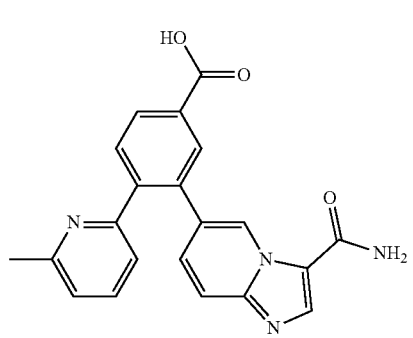
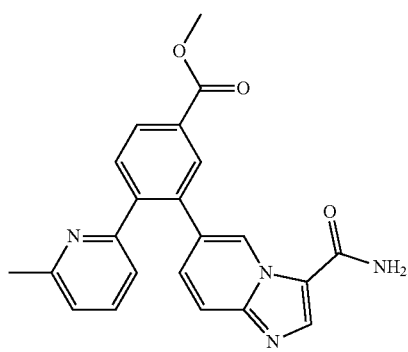
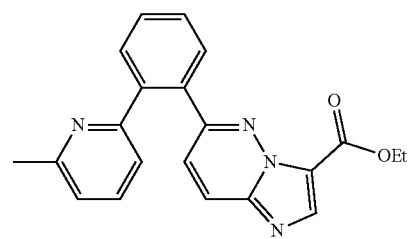
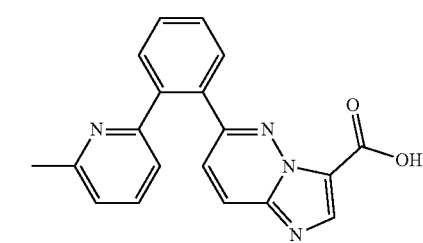
10. A process for preparing the nitrogenous aromatic heterocyclic compound represented by formula I as defined in claim 1, which is process 1 or process 2;
the process 1 comprises conducting a coupling reaction of a compound represented by formula I-1 with a compound represented by formula I-2 as shown below;

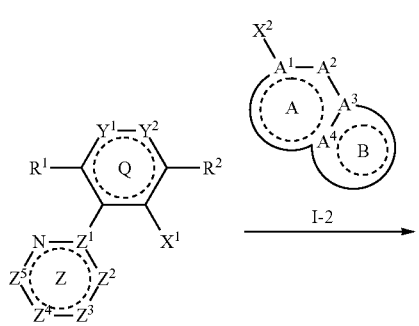

I-1

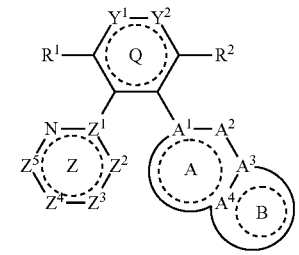

I wherein $X^1$ is $C_1$, Br, I or —$OSO_2CF_3$, $X^2$ is —$BF_3K$ or —$B(OR^{35})_2$;

or, $X^2$ is $C_1$, Br, I or —$OSO_2CF_3$, $X^1$ is —$BF_3K$ or —$B(OR^{35})_2$;

wherein $R^{35}$ is hydrogen or $C_1$-$C_6$ alkyl, or two $OR^{35}$ together with the boron atom to which they are attached form

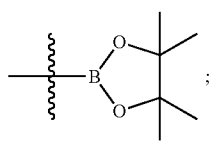 [SMILES: *B1OC(C)(C)C(C)(C)O1]

the process 2 comprises conducting a coupling reaction of a compound represented by formula II-1 with a compound represented by formula II-2 as shown below;

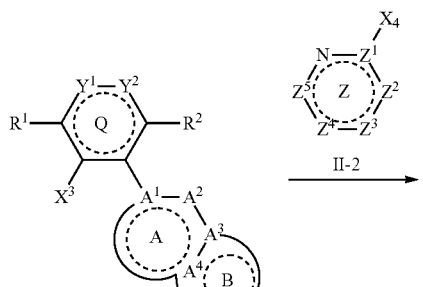

II-1

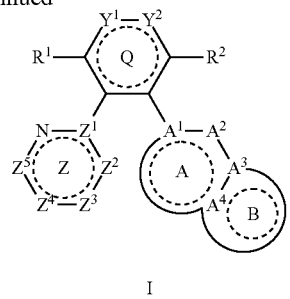

I wherein, $X^3$ is $C_1$, Br, I or —$OSO_2CF_3$; $X^4$ is $SnBu_3$;

or $X^4$ is $C_1$, Br, I or —$OSO_2CF_3$; $X^3$ is $SnBu_3$;

$R^1, R^2, Z^1, Z^2, Z^3, Z^4, Z^5, Y^1, Y^2, A^1, A^2, A^3, A^4$, ring Z, ring Q, ring A and ring B are defined as claim 1.

11. A method for treating an ALK5 mediated disease in a subject in need thereof, comprising administering a pharmaceutically effective amount of the nitrogenous aromatic heterocyclic compound represented by formula I or the pharmaceutically acceptable salt thereof as defined in claim 1.

12. The method as defined in claim 11, wherein, the ALK5 mediated disease is selected from the group consisting of cancer, organ fibrosis, viral infection, chronic nephritis, acute nephritis, diabetic nephropathy, osteoporosis, arthritis, wound healing, ulceration, corneal trauma, heart valve stenosis, congestive cardiac necrosis, neurologic impairment, Alzheimer's syndrome, peritoneal or subcutaneous adhesions, atherosclerosis and tumor metastasis.

13. The method as defined in claim 12, wherein, the cancer is selected from the group consisting of colon cancer, pancreatic cancer, breast cancer, prostate cancer, lung cancer, brain cancer, ovarian cancer, cervical cancer, testicular cancer, kidney cancer, head or neck cancer, bone cancer, skin cancer, rectal cancer, liver cancer, colon cancer, esophagus cancer, stomach cancer, pancreatic cancer, thyroid cancer, bladder cancer, lymphoma, leukemia and melanoma; and/or, the organ fibrosis is selected from the group consisting of renal fibrosis, liver fibrosis and pulmonary fibrosis.

14. A pharmaceutical composition comprising a nitrogenous aromatic heterocyclic compound represented by formula I and the pharmaceutically acceptable salt thereof as defined in claim 1, and a pharmaceutically acceptable carrier.

* * * * *